United States Patent [19]

Cohen et al.

[11] Patent Number: 5,739,107
[45] Date of Patent: Apr. 14, 1998

[54] MORPHOGEN TREATMENT OF GASTROINTESTINAL ULCERS

[75] Inventors: Charles M. Cohen, Medway; Marc F. Charette, Needham; Thangavel Kuberasampath, Medway; David C. Rueger, Hopkinton; Hermann Oppermann, Medway, all of Mass.; Roy H. L. Pang, Etna, N.H.; Engin Ozkaynak, Milford; John E. Smart, Weston, both of Mass.

[73] Assignee: Creative BioMolecules, Inc., Hopkinton, Mass.

[21] Appl. No.: 462,623

[22] Filed: Jun. 5, 1995

Related U.S. Application Data

[63] Continuation of Ser. No. 174,605, Dec. 28, 1993, abandoned, which is a continuation of Ser. No. 945,286, Sep. 15, 1992, abandoned, which is a continuation-in-part of Ser. No. 938,336, Aug. 28, 1992, abandoned, Ser. No. 753,059, Aug. 30, 1991, abandoned, and Ser. No. 752,764, Aug. 30, 1991, abandoned, which is a continuation-in-part of Ser. No. 667,274, Mar. 11, 1991, abandoned, said Ser. No. 753,059, is a continuation-in-part of Ser. No. 667,274.

[51] Int. Cl.$^6$ .......................... A61K 38/18; C07K 14/51
[52] U.S. Cl. ............................................ 514/12; 530/350
[58] Field of Search ........................ 514/2, 12; 530/350, 530/399

[56] References Cited

U.S. PATENT DOCUMENTS

| | | | |
|---|---|---|---|
| 4,806,523 | 2/1989 | Bentz et al. | 514/2 |
| 4,877,864 | 10/1989 | Wang et al. | 514/12 |
| 4,919,939 | 4/1990 | Baker | 424/493 |
| 4,968,590 | 11/1990 | Kuberasampath et al. | 530/326 |
| 4,971,952 | 11/1990 | Bentz et al. | 514/12 |
| 4,975,526 | 12/1990 | Kuberasampath et al. | 530/350 |
| 4,983,581 | 1/1991 | Antoniades et al. | 514/12 |
| 5,008,240 | 4/1991 | Bentz et al. | 514/2 |
| 5,011,691 | 4/1991 | Oppermann et al. | 424/423 |
| 5,013,649 | 5/1991 | Wang et al. | 435/25 |
| 5,043,329 | 8/1991 | Lichtenberger | 514/78 |
| 5,091,513 | 2/1992 | Huston et al. | 530/387.3 |
| 5,102,870 | 4/1992 | Florine et al. | 514/12 |
| 5,106,626 | 4/1992 | Parsons et al. | 424/423 |
| 5,108,753 | 4/1992 | Kuberasampath et al. | 424/422 |
| 5,108,989 | 4/1992 | Amento et al. | 514/12 |
| 5,110,795 | 5/1992 | Hahn | 514/17 |
| 5,118,791 | 6/1992 | Burnier et al. | 530/326 |
| 5,135,915 | 8/1992 | Czarniecki et al. | 514/21 |
| 5,141,905 | 8/1992 | Rosen et al. | 435/69.1 |
| 5,234,908 | 8/1993 | Szabo et al. | 514/12 |

FOREIGN PATENT DOCUMENTS

| | | |
|---|---|---|
| 0148155 | 7/1985 | European Pat. Off. |
| 0269408 | 6/1988 | European Pat. Off. |
| 0416578 | 3/1991 | European Pat. Off. |
| 84/01106 | 3/1984 | WIPO |
| 88/00205 | 1/1988 | WIPO |
| 89/09787 | 10/1989 | WIPO |
| 89/09788 | 10/1989 | WIPO |
| 89/10409 | 11/1989 | WIPO |
| 90/00900 | 2/1990 | WIPO |
| 90/01941 | 3/1990 | WIPO |
| 90/03733 | 4/1990 | WIPO |
| 90/10018 | 9/1990 | WIPO |
| 91/05802 | 5/1991 | WIPO |
| 91/18558 | 12/1991 | WIPO |
| 92/07073 | 4/1992 | WIPO |
| 92/09301 | 6/1992 | WIPO |
| 92/15323 | 9/1992 | WIPO |
| 93/04692 | 3/1993 | WIPO |

OTHER PUBLICATIONS

Szabo et al. (1977), "Pathogenesis of Duodenal Ulcer, Gastric Hyperacidity Caused by Propionitrile and Cyteamine in Rats," Res. Comm. Chem. Pathol. Pharmacol., 16:311–323.

Onderdonk et al. (1979), "Bacteriological Studies of Experimental Ulcerative Colitis," Am. J. Clin. Nutr., 32:258–265.

Clark et al. (1985), "Coregulation of Collagenase and Collagenase Inhibitor Production by Phorbol Myristate Acetate in Human Skin Fibroblasts", Arch. Bio. Chem. Biophys., 241:36–44.

Onderdonk (1985), "Experimental Models for Ulcerative Colitis," Dig. Diseases Sci., 30:40S–44S.

Pihan et al. (1985), "Biliary and Pancreatic Secretions Influence Experimental Duodenal Ulcer Without Affecting Gastric Secretion in the Rat," Dig. Diseases Sci., 30:240–246.

Forage et al. (1986), "Cloning and Sequence Analysis of cDNA Species Coding for the Two Subunits of Inhibin from Bovine Follicular Fluid," Proc. Natl. Acad. Sci. USA 83:3091–3095.

Massagué (1987), "The TGF-β Family of Growth and Differentiation Factors," Cell 49:437–438.

Cheifetz et al. (1988), "A Surface Component on GH3 Pituitary Cells That Recognizes Transforming Growth Factor-B, Activin, and Inhibin," J. Biol. Chem. 263, (No. 33) 17725–17728.

George et al. (1988), "Current Methods in Sequence Comparison and Analysis" Macromolecular Sequencing and Synthesis Selected Methods and Applications, Ch. 12, 127–149.

(List continued on next page.)

Primary Examiner—James Ketter
Assistant Examiner—Robert Schwartzman
Attorney, Agent, or Firm—Testa, Hurwitz & Thibeault, LLP

[57] ABSTRACT

Disclosed are methods and compositions for maintaining the integrity of the gastrointestinal tract luminal lining in a mammal, including (1) limiting epithelial cell proliferation, (2) inhibiting ulcerative lesion formation, (3) inhibiting inflammation normally associated with ulcerative diseases, and (4) stimulating the repair of ulcerative lesions and the regeneration of the luminal tissue. The methods and compositions include a therapeutically effective amount of a morphogen as defined herein.

24 Claims, 5 Drawing Sheets

OTHER PUBLICATIONS

Heath et al. (1988), "Regulatory Factors of Embryonic Stem Cells," *J. Cell Sci. Supp.* 10:257–266.

Krummel et al. (1988), "Transforming Growth Factor Beta (TGF–B) Induces Fibrosis in a Fetal Wound Model," *Journal of Pediatric Surgery* 23:647–652.

Pepinsky et al. (1988), "Proteolytic Processing of Mullerian Inhibiting Substance Produces a Transforming Growth Factor–β–like Fragment," *J. Biol. Chem.* 263:18961–18964.

Postlethwaite et al. (1988), "Modulation of Fibroblast Functions by Interleukin 1: Increased Steady–State Accumulation of Type I Procollagen Messenger RNAs and Stimulation of Other Functions but Not Chemotaxis by Human Recombinant Interleukin 1α and β", *J. Cell Biol.*, 103:311–318.

Sugino et al. (1988), "Identification of a Specific Receptor for Erythroid Differentiation Factor on Follicular Granulosa Cell," *J. Biol. Chem.* 263:(No. 30); 15249–15252.

Williams (1988), "The Role of Diffusible Molecules in Regulating the Cellular Differentiation of *Dictyostelium discoideum*," *Development* 103:1–16.

Postlethwaite et al. (1989), "Stimulation of Glycosaminoglycan Synthesis in Cultured Human Dermal Fibroblasts by Interleukin 1", *J. Clin. Invest.*, 83:629–636.

Sporn et al. (1989), "Transforming Growth Factor–β," *JAMA* 262:7; 938–941.

Wahl et al. (1989), "Inflammatory and Immunomodulatory Roles of TGF–β," *Immunol. Today* 10:258–261.

Border et al. (1990), "Suppression of Experimental Glomerulonephritis by Antiserum Against Transforming Growth Factor B1," *Nature* 346:371–374.

Coffman et al. (1990), "Xotch, the Xenopus Homolog of *Drosophila notch*," *Science* 249:1438–1441.

Gennaro (1990) *Remington's Pharmaceutical Sciences* (Mack Pubs., N.Y.).

Gray et al. (1990), "Requirement for Activin A and Transforming Growth Factor–B1 Pro–Regions in Homodimer Assembly," *Science* 247:1328–1330.

Lefer et al. (1990), "Mediation of Cardioprotection by Transforming Growth Factor–B," *Science* 249:61–64.

Okayasu et al. (1990), "A Novel Method in the Induction of Reliable Experimental Acute and Chronic Ulcerative Colitis in Mices," *Gastroenterology*, 98:694–702.

Okuda et al. (1990), "Elevated Expression of Transforming Growth Factor–B and Proteoglycan Production in Experimental Glomerulonephritis, Possible Role in Expansion of the Mesangial Extracellular Matrix," *J. Clin. Invest.* 86:453–462.

Sonis et al. (1990), "An Animal Model for Mucositis Induced by Cancer Chemotherapy," *Oral Surg. Oral Med. Oral Pathol.* 69:437–443.

Van Den Eijnden–Van Raaij et al. (1990), "Activin–Like Factor from a *Xenopus laevis* Cell Line Responsible for Mesoderm Induction," *Nature* 345:732–734.

Caplan (1991), "Mesenchymal Stem Cells," *J. Orthop. Res.* 9:641–650.

Castilla et al. (1991), "Transforming Growth Factors B1 and α in Chronic Liver Disease," *The New England Journal of Medicine* 324:933–939.

Fava et al. (1991), "Transforming Growth Factor β1 (TGF–β1) Induced Neutrophil Recruitment to Synovial Tissues: Implications for TGF–β–driven Synovial Inflammation and Hyperplasia," *J. Exp. Med.*, 173:1121–1132.

Fausto et al. (1991), "Effects of TGF–βs in the Liver: Cell Proliferation an Fibrogenesis," 157 *Ciba Found. Symp.* 165–174.

Gallagher (1991), "Oral Mucous Membrane Reactions to Drugs and Chemicals," *Curr. Opn. in Dent.*, 1:777–782.

Khalil et al. (1991), "Increased Production and Immunohistochemical Localization of Transforming Growth Factor–B in Idiopathic Pulmonary Fibrosis," *Am. J. Respir. Cell Mol. Biol.* 5:155–162.

Kuruvilla et al. (1991), "Protective Effect of Transforming Growth Factor B1 on Experimental Autoimmune Diseases in Mice," *Proc. Natl. Acad. Sci. USA* 88:2918–2921.

Whitby et al. (1991), "Immunohistochemical Localization of Growth Factors in Fetal Wound Healing," *Development Biology* 147:207–215.

Border et al. (1992), "Transforming Growth Factor–β in Disease: The Dark Side of Tissue Repair," *J. Clin. Invest.* 90:1–7.

Wahl (1992), "Transforming Growth Factor Beta (TGF–β) in Inflammation: A Cause and A Cure," *J. Clin. Immun.* 12:61–74.

Estevez et al. (1993), "The daf–4 Gene Encodes a Bone Morphogenetic Protein Receptor Controlling C. Elegans Dauer Larva Development," *Nature* 365:644–649.

Perides et al. (1993), "Osteogenic Protein–1 Regulates L1 and Neural Cell Adhesion Molecule Gene Expression in Neural Cells," *J. Biol. Chem.* 268:197–25205.

Wahl et al. (1993), "Reversal of Acute and Chronic Synovial Inflammation by Anti–Transforming Growth Factor β," *J. Exp. Med.* 177:225–230.

Wall et al. (1993), "Biosynthesis and In Vivo Localization of the Decapentaplegic–Vg–Related Protein, DVR–6 (Bone Morphogenetic Protein–6)," *J. Cell Biol.* 120(2):493–502.

Kinglsey (1994), "The TGF–B Superfamily: New Members, New Receptors, and New Genetic Tests of Function in Different Organisms," *Genes & Development* 8:133–146.

Koenig et al. (1994), "Characterization and Cloning of a Receptor for BMP–2 and BMP–4 From NIH 3T3 Cells," *Mol. Cell Biol.* 14:5961–5974.

Perides et al. (1994), "Regulation of Neural Cell Adhesion Molecule and L1 by the Transforming Growth Factor–β Superfamily," *J. Biol. Chem.* 269:765–770.

Sanderson et al. (1995), "Hepatic Expression of Mature Transforming Growth Factor β1 in Transgenic Mice Results in Multiple Tissue Lesions," *Proc. Natl. Acad. Sci. USA* 92:2572–2576.

Sampath et al. (1983), "Homology of Bone–Inductive Proteins From Human, Monkey, Bovine, and Rat Extracellular Matrix," *Proc. Natl. Acad. Sci. USA* 80:6591–6595.

Mason (1985), "Complementary DNA Sequences of Ovarian Follicular Fluid Inhibin Show Precursor Structure and Homology with Transforming Growth Factor–B," *Nature* 318:659–663.

Cate et al. (1986), "Isolation of the Bovine and Human Genes for Mullerian Inhibiting Substance and Expression of the Human Gene in Animal Cells," *Cell* 45:685–698.

Chomcyzaski et al. (1987), "Single–Step Method of RNA Isolation by Acid Guanidinium Thiocyanate–Phenol–Chloroform Extraction", *Anal. Biochem.*, 162:156–159.

Miller et al. (1987), "Phenotypic Modulation of the Swarm Rat Chondrosarcoma Induced by Morphogenetic Bone Matrix," *Cancer Research* 42:3589–3594.

Padgett et al. (1987), "A Transcript from a Drosophila Pattern Gene Predicts a Protein Homologous to the Transforming Growth Factor–B Family," *Nature* 325:81–84.

Weeks et al. (1987), "Maternal mRNA Localized to the Vegetal Hemisphere Xenopus Eggs Codes for a Growth Factor Related to TGF–B," *Cell* 51:861–867.

Freston (1988), "The Pathophysiological and Pharmacological Basis of Peptic Ulcer Therapy," *Toxicol. Pathol.* vol. 16, 2:260–266.

Rosen et al.; Wozney et al.; Wang et al. (1988) *Calcified Tissue International* 42 (Suppl.): A35 (Abstr. No. 136); A37 (Abstr. No. 146 and 147).

Wang et al. (1988), "Purification and Characterization of Other Distinct Bone–Inducing Factors," *Proc. Natl. Acad. Sci. USA* 85:9484–9488.

Wozney et al. (1988), "Novel Regulators of Bone Formation: Molecular Clones and Activities," *Science* 242:1528–1533.

Lyons (1989), "VGR–1, A Mammalian Gene Related to Xenopus VG–1, is a member of the Transforming Growth Factor Beta Gene Superfamily", *Proc. Nat. Acad. Sciences* 86: 4554–4558.

Lyons et al. (1989), "Patterns of Expression of Murine VGR–1 and BMP–2a RNA Suggest That Transforming Growth Factor–B–Like Genes Coordinately Regulate Aspects of Embryonic Development," *Genes & Development* 3:1657–1668.

Mason et al. (1989), "Activin B: Precursor Sequences, Genomic Structure and in Vitro Activities," *Molecular Endocrinology* 3 (No. 9):1352–1358.

Rosen et al. (1989), "Purification and Molecular Cloning of a Novel Group of BMPs and Localization of BMP mRNA in Developing Bone," 20 *Conn. Tissue Res.* 313–319.

Vukicevic et al. (1989), "Stimulation of the Expression of Osteogenic and Chondrogenic Phenotypes in vitro by Osteogenin," *Proc. Nat'l. Acad. Sci. USA* 86:8793–8797.

Wozney (1989), "Bone Morphogenetic Proteins," *Progress in Growth Factor Research* 1:267–280.

Behringer et al. (1990), "Abnormal Sexual Development in Transgenic Mice Chronically Expressing Mullerian Inhibiting Substance," *Nature* 345:167–170.

Celeste et al. (1990), "Identification of Transforming Growth Factor Beta Family Members Present in Bone–Inductive Protein Purified from Bovine Bone," *Proc. Nat. Acad. Sciences* 87:9843–9847.

Green et al. (1990), "Graded Changes in Dose of a Xenopus Activin A Homologue Elicit Stepwise Transitions in Embryonic Cell Fate," *Nature* 347:391–394.

Katagiri et al. (1990), "The Non–Osteogenic Mouse Pluripotent Cell Line, C3H10T1/2, Is Induced to Differentiate Into Osteoblastic Cells By Recombinant Human Bone Morphogenetic Protein–2," *Biochem. Biophys. Res. Comm.* 172:1; 295–299.

Lee (1990), "Identification of a Novel Member (GDF–1) of the Transforming Growth Factor–B Superfamily," *Molecular Endocrinology* 4 (No. 7):1034–1040.

Ozkaynak et al. (1990), "OP–1 cDNA Encodes an Osteogenic Protein in the TGF–B Family," *EMBO J.* 9 (No. 7):2085–2093.

Panganiban et al. (1990), "Biochemical Characterization of the *Drosophila dpp* Protein, a Member of the Transforming Growth Factor B Family of Growth Factors," *Molecular and Cellular Biology* 10, (No. 6) 2669–2677.

Rosen et al.; Celeste et al. (1990), *J. Cell. Biochem.*; Supplement 14E 33 (Abstr. No. 0–004); 54 (Abstr. No. 0–105).

Sampath et al. (1990), "Bovine Osteogenic Protein Is Composed of Dimers of OP–1 and BMP–2A, Two Members of the Transforming Growth Factor–B Superfamily," *J. Biol. Chem.* 265:13198–13205.

Schubert et al. (1990), "Activin is a Nerve Cell Survival Molecule," *Nature* 344:868–870.

Smith et al. (1990), "Identification of a Potent Xenopus Mesoderm Inducing Factor as a Homologue of Activin A," *Nature* 345:729–731.

Sokol et al. (1990), "A Mouse Macrophage Factor Induces Head Structures and Organizes a Body Axis in Xenopus," *Science* 249:561–563.

Wang et al. (1990), "Recombinant Human Bone Morphogenetic Protein Induces Bone Formation," *Proc. Natl. Acad. Sci. USA* 87:2220–2224.

Wozney et al. (1990), "Growth Factors Influencing Bone Development," *J. Cell Sci.* Suppl. 13:149–156.

Yannas (1990), "Biologically Active Analogues of the Extracellular Matrix: Artificial Skin and Nerves," *Angew. Chem. Int. Ed. Engl.* 29:20–35.

Chen et al. (1991), "Bone Morphogenetic Protein–2b Stimulation of Growth and Osteogenic Phenotypes in Rat Osteoblast–like Cells: Comparison with TGF–$\beta$," *J. Bone Min. Res.* 6:1387–1393.

D'Allessandro et al. (1991), *J. Cell Biochem.* Suppl. 15F (Abstr. No. 105).

Israel et al. (1991), Abstract Q–111 *J. Cell. Biochem. Suppl.*

Lee (1991), "Expression of Growth/Differentiation Factor 1 in the Nervous System: Conservation of a Bicistronic Structure," *Proc. Natl. Acad. Sci. USA,* 88:4250–4254.

Ozkaynak et al. (1991), "Murine Osteogenic Protein (OP–1): High Levels of mRNA in Kidney," *Biochem. Biophys. Res. Comm.* 179:116–123.

Takuwa et al. (1991), "Bone Morphogenetic Protein–2 Stimulates Alkaline Phosphatase Activity and Collagen Synthesis In Cultured Osteoblastic Cells, MC3T3–E1," *Biochem. Biophys. Res. Comm.* 174:1; 96–101.

Wharton et al. (1991), "Drosophila 60A Gene, Another Transforming Growth Factor $\beta$ Family Member, is Closely Related to Human Bone Morphogenetic Proteins," *Proc. Natl. Acad. Sci. USA* 88:9214–9218.

Yamaguchi et al. (1991), "Recombinant Human Bone Morphogenetic Protein–2 Stimulates Osteoblastic Maturation and Inhibits Myogenic Differentiation in Vitro," *J. Cell. Biol.* 113:681–687.

Israel et al. (1992), "Expression and Characterization of Bone Morphogenetic Protein–2 in Chinese Hamster Ovary Cells," *Growth Factors* 7:139–150.

Lefer et al. (1992), "Anti–Ischaemic and Endothelial Protective Actions of Recombinant Human Osteogenic Protein (hOP–1)," *J. Mol. Cell. Cardiol.* 24:585–593.

Rogers et al. (1992), "Bone Morphogenetic Proteins–2 and –4 are Involved in the Retinoic Acid–Induced Differentiation of Embryonal Carcinoma Cells," *Mol. Biol. Cell* 3:2; 189–196.

Rosen et al., Celeste et al., Wozney et al. (1992), *J. Cell Biochem.* Suppl. 16F (Abstr. Nos. W513, W502 and W026).

Thies et al. (1992), "Recombinant Human Bone Morphogenetic Protein–2 Induces Osteoblastic Differentiation in W–20–17 Stromal Cells," *Endocrinology* 139:3; 1318–1324.

Wozney (1992), "The Bone Morphogenetic Protein Family and Osteogenesis," *Mol. Reprod. & Dev.* 32:160–167.

Alper (1993), "Ulcers as an Infectious Disease," *Science* 260:159–160.

Basler et al. (1993). "Control of Cell Pattern in the Neural Tube: Regulation of Cell Differentiation by Dorsalin–1, a Novel TGFβ Family Member." *Cell* 73:687–702.

Padgett et al. (1993). "Human BMP Sequences Can Confer Normal Dorsal–Ventral Patterning in the Drosophila Embryo." *Proc. Natl. Acad. Sci. USA* 90:2905–2909.

Sampath et al. (1993). "Drosophila Transforming Growth Factor B Superfamily Proteins Induce Endochondral Bone Formation in Mammals." Proc. Natl. Acad. Sci. USA 90:6004–6008.

Storm et al. (1994). "Limb Alterations in Brachypodism Mice Due To Mutations in a New Member of the TGF–β–Superfamily." *Nature* 368 639–643.

Vukicevic et al. (1994). "Localization of Osteogenic Protein–1 (Bone Morphogenetic Protein–7) During Human Embryonic Development: High Affinity Binding to Basement Membranes." *Biochem. and Biophys. Res. Communications* 198:693–700.

MORPHOGEN TREATMENT OF GASTROINTESTINAL ULCERS

REFERENCE TO RELATED APPLICATIONS

This is a continuation of U.S. Ser. No. 08/174,605, filed on Dec. 28, 1993, abandoned, which is a continuation of U.S. Ser. No. 07/945,286, filed on Sep. 15, 1992, abandoned, which is a continuation-in-part of each of U.S. Ser. No. 07/938,336, filed Aug. 28, 1992, abandoned, U.S. Ser. No. 07/752,764, filed Aug. 30, 1991, abandoned, and U.S. Ser. No. 07/753,059, filed Aug. 30, 1991, abandoned, each of the latter two being a continuation-in-part of U.S. Ser. No. 07/667,274, filed Mar. 11, 1991, abandoned.

FIELD OF THE INVENTION

The invention relates generally to the treatment of gastrointestinal (GI) disorders. In particular, the invention relates to the treatment of ulcerative diseases within the gastrointestinal tract of a mammal.

BACKGROUND OF THE INVENTION

The luminal lining of the mammalian gastrointestinal tract (GI tract), which extends from the mouth cavity to the rectum, includes a protective layer of continually proliferating basal epithelial cells overlying a mucosal layer. Together, the basal epithelium and mucosa create the protective "gastrointestinal barrier." Disruption of this barrier results in lesions that can become infected and/or expose underlying tissue to the corrosive effect of gastric juices. Gastrointestinal ulcerations can cause oral mucositis, gastric ulcers, necrotizing enterocolitis, regional ileitis, ulcerative colitis, regional enteritis (Crohn's disease), proctitis, and other forms of inflammatory bowel disease (IBD).

Ulcerative oral mucositis is a serious and dose-limiting toxic side effect of many forms of cancer therapies, including chemotherapy and radiation therapy. Oral mucositis accounts for significant pain and discomfort for these patients, and ranges in severity from redness and swelling to frank ulcerative lesions. Chemotherapeutic agents and radiation can kill or damage the epithelial cells lining the oral cavity. Such damage includes the inhibitory effect that chemotherapeutic agents may have on mitoses of the rapidly dividing cells of the oral basal epithelium. The severity of damage is related to the type and dose of chemotherapeutic agent(s) and concomitant therapy such as radiotherapy. Further, ulceration is hastened if sources of chronic irritation such as defective dental restorations, fractured teeth or ill-fitting dental prostheses are present. Oral mucositis most often affects the nonkeratinized mucosa of the cheeks, lips, soft palate, ventral surface of the tongue and floor of the mouth, approximately one to two weeks after cancer therapy. The lesions often become secondarily infected and become much harder to heal. The disruption in the oral mucosa results in a systemic portal of entry for the numerous microorganisms found in the mouth. Consequently, the oral cavity is the most frequently identifiable source of sepsis in the granulocytopenic cancer patient. Of primary concern are those patients undergoing: chemotherapy for cancer such as leukemia, breast cancer or as an adjuvant to tumor removal; radiotherapy for head and neck cancer; and combined chemotherapy and radiotherapy for bone marrow transplants.

One source of oral mucositis can result from xerostomia, or chronic mouth dryness, which typically results from diminished or arrested salivary secretion or asialism. Salivary gland dysfunction or atrophy may result from tissue senescence in aged individuals, or from an organic disorder. Most frequently, xerostomia is an undesired side effect of a clinical or pharmaceutical therapy. Normally, saliva moistens the oral mucosal membrane, allowing for the dissolution and limited absorption of exogenous substances introduced into the oral cavity. In xerostomaic individuals irritating exogenous substances, including foods and medications, remain exposed to the mucosa and can cause inflammation and ulceration. A description of xerostomia-causing medications is described in Gallager, et al. (1991) Current Opinion in Dentistry 1:777–782.

Current therapy for mucositis is limited to either local or systemic palliation or topical antibacterial therapy. At present there is no effective treatment for mucositis. Therapy typically is limited to pain medications and treatment of secondary infection. In particular, recommendations have included treatment with topical anesthetics such as xylocaine, benzocaine and cocaine, treatment with solutions which coat the ulcerative lesions with a polysaccharide gel and use of antiseptic solutions such as Chlorhexadine. While all these treatments do provide some relief, none are directed to the actual healing of oral mucositis, which entails directly healing the mucosal epithelium cells.

Recently, certain local-acting growth factors, such as TGF-α have been shown to have some effect on ulcerative mucositis lesions at low concentrations, but less effect at higher concentrations (see U.S. Pat. No. 5,102870, issued Apr. 7, 1992 to Florine et al.) The biphasic effect exhibited by such factors may limit their clinical utility. There remains a need for a therapy that inhibits ulcerative mucositis lesion formation and significantly enhances healing of lesions following their formation.

Gastrointestinal ulcer disease, in particular, peptic ulcers, affect 5–15% of the United States population. Peptic ulcers include gastric ulcers, which occur as lesions in the wall of the stomach, and duodenal ulcers, which are deep lesions that occur in the wall of the duodenum, i.e., the upper portion of the small intestine. Another ulcer disease, particularly worrisome to pediatricians, occurs in the premature infants. This condition, known as necrotizing enterocolitis, affects 10–15% of newborns having a birth weight of under 1.5 kg and results in severe ulceration of the small intestine, which frequently requires surgery. Gastric ulcers can result from an imbalance in factors which maintain the natural gasatrointestinal barrier, including factors which neutralize corrosive gastric juices, such as the mucous bicarbonate, and other factors which protect the body from luminal damaging agents. Although current antiulcer therapeutics, including antisecretory products such as cimetidine and ranitidine, appear to be effective in healing duodenal ulcers, it is generally believed that they are effective because they reduce normal gastric acid secretion. While the reduction in acidity aids in the closure of the ulcer, it also interferes with normal digestion. Accordingly, a high percentage of ulcers healed with current therapies recur within one year of therapy. The high rate of ulcer recurrence is thought to be at least partially attributable to the reduced number of mucus-producing cells in the scar tissue which is left at the site of the healed ulcer, rendering the area more vulnerable to rupture when the gastointestinal acidity returns to normal.

PCT Application No. PCT/U.S. 89/03467 discloses the use of an acid-resistant local-acting fibroblast growth factor to treat GI ulcers. U.S. Pat. No. 5,043,329 discloses the use of phospholipids to treat ulcers of the gastrointestinal tract.

Severe ulceration of the gastrointestinal mucosa also can spontaneously occur in the lower bowel (distal ileum and colon) in a spectrum of clinical disorders called inflammatory bowel disease (IBD). The two major diseases in this classification are ulcerative colitis and regional enteritis (Crohn's Disease) which are associated with severe mucosal ulceration (frequently penetrating the wall of the bowel and forming strictures and fistulas), severe mucosal and submucosal inflammation and edema, and fibrosis. Other forms of IBD include regional ileitis and proctitis. Clinically, patients with fulminant IBD can be severely ill with massive diarrhea, blood loss, dehydration, weight loss and fever. The prognosis of the disease is not good and frequently requires resection of the diseased tissue.

It is an object of this invention to provide methods and compositions for maintaining the integrity of the gastrointestinal luminal lining in a mammal. Another object is to provide methods and compositions for regenerating basal epithelium and mucosa in ulcerated gastrointestinal tract barrier tissue, including the oral mucosa. Another object of the invention is to provide tissue protective methods and compositions that allow extension or enhancement of a chemical or radiotherapy. Another object is to provide methods and compositions capable of limiting the proliferation of epithelial cells, particularly the basal epithelial cels of the gastrointestinal tract. Still another object is to provide methods and compositions for substantially inhibiting inflammation normally associated with ulcerative diseases. Another object is to provide methods and compositions for protecting mucosal tissue from the tissue desctructive effects associated with xerostomia. Yet another object is to provide methods and compositions for the treatment of oral mucositis, peptic ulcers, ulcerative colitis, regional enteritis, necrotizing enterocolitis, proctitis and other ulcerative diseases of the gastrointestinal tract.

These and other objects and features of the invention will be apparent from the description, drawings, and claims which follow.

SUMMARY OF THE INVENTION

It now has been discovered that morphogenic proteins ("morphogen"), as defined herein, are useful as therapeutic methods and compositions for protecting the luminal lining of the gastrointestinal tract from ulceration, particularly in individuals at risk for ulcer formation. Specifically, the morphogens decribed herein can limit the proliferation of epithelial cells, inhibit the inflammation normally associated with ulcerative disease, inhibit scar tissue formation, and induce repair and regeneration of the ulcerated tissue.

In one aspect, the invention features compositions and therapeutic treatment methods that comprise the step of administering to a mammal a therapeutically effective amount of a morphogenic protein ("morphogen"), as defined herein, upon injury to all or a portion of the GI tract luminal lining, or in anticipation of such injury, for a time and at a concentration sufficient to maintain the integrity of the GI tract luminal lining, including repairing ulcerated tissue, and/or inhibiting damage thereto.

In another aspect, the invention features compositions and therapeutic treatment methods for maintaining the integrity of the GI tract luminal lining in a mammal which include administering to the mammal, upon injury to all or a portion of the GI tract luminal lining, or in anticipation of such injury, a compound that stimulates in vivo a therapeutically effective concentration of an endogenous morphogen within the body of the mammal sufficient to maintain the integrity of the luminal lining, including regenerating ulcerated tissue and/or inhibiting damage thereto. These compounds are referred to herein as morphogen-stimulating agents, and are understood to include substances which, when administered to a mammal, act on cells in tissue(s) or organ(s) that normally are responsible for, or capable of, producing a morphogen and/or secreting a morphogen, and which cause the endogenous level of the morphogen to be altered. The agent may act, for example, by stimulating expression and/or secretion of an endogenous morphogen.

As used herein, "gastrointestinal tract" means the entire gastrointestinal tract of a mammal, from the mouth to the rectum, inclusive, including the mouth cavity, esophagus, stomach, upper and lower intestines, and colon. As used herein, "ulcer" refers to an open lesion or break of the integrity of the epithelial lining of the gastrointestinal tract, resulting in erosion of the underlying mucosa. "Maintaining the integrity of the luminal lining" means providing an effective morphogen concentration to the cells of the gasatrointestinal tract luminal lining, the concentration being sufficient to substantially inhibit lesion formation in the basal epithelium of the gastrointestinal barrier, including stimulating the regeneration of damaged tissue and/or inhibiting additional damage thereto. "Protecting" mucosal tissue means providing a therapeutically effective morphogen concentration to the cells of the gastrointestinal tract luminal lining sufficient to inhibit the tissue damage associated with tissue ulceration, including stimulating regeneration of damaged tissue and/or inhibiting additional damage thereto. "Symptom-alleviating cofactor" refers to one or more pharmaceuticals which may be administered together with the therapeutic agents of this invention and which alleviate or mitigate one or more of the symptoms typically associated with periodontal tissue loss. Exemplary cofactors include antibiotics, antiseptics, anti-viral and anti-fungal agents, non-steroidal antiinflammatory agents, anesthetics and analgesics, and antisecretory agents.

In preferred embodiments of the invention, the mammal is a human and ulcers treatable according to the invention include those found in the ileum which cause regional ileitis, those found in the colon which cause ulcerative colitis, regional enteritis (Crohn's disease), proctitis and other forms of inflammatory bowel disease (IBD), gastric ulcers such as those found in the stomach, small intestines, duodenum and esophagus; and ulcers found in the mouth. The compositions and methods described herein are particularly useful in treating mucositis lesions caused by chemotherapy or radiation therapy.

Because the morphogens described herein inhibit ulceration of the oral mucosa that typically results from cancer therapies, in another aspect, the invention provides cancer treatment methods and compositions that significantly reduce or inhibit the onset of oral mucositis in a patient. In addition, the morphogens described herein may be used in conjunction with existing chemical or radiation therapies to enhance their efficacy. Cancer chemical and radiation therapies currently in use often are limited in dose or duration by the onset of severe oral mucositis and/or the sepsis which often follows lesion formation. The morphogens described herein can inhibit lesion formation and, accordingly, their administration to a patient as part of a cancer therapy may allow significant enhancement of current therapy doses and/or treatment times.

The morphogens described herein can limit cell proliferation in a proliferating epithelial cell population, thereby protecting these cells from the cytotoxic effects of chemotherapeutic and radiotherapeutic treatments. Accordingly, in another aspect, the invention provides methods and compositions for limiting the mitogenic activity of epithelial cells.

This activity of the morphogens also has application for other diseases associated with proliferating epithelial cells, including psoriasis and other such skin tissue disorders. In addition, this activity of morphogens also may be useful to limit hair loss typically associated with cancer therapies.

The morphogens described also herein inhibit inflammation. Accordingly, in another aspect, the invention provides methods and compositions for inhibiting the inflammation associated with ulcerative disease.

The morphogens described herein also stimulate tissue morphogenesis at a site of tissue damage, inhibiting scar tissue formation at a lesion site. Accordingly, another aspect of the invention includes methods and compositions for inhibiting scar tissue formation at a lesion site.

In another aspect of the invention, the morphogens described herein are useful in protecting the mucosal membrane from the tissue destructive effects associated with xerostomia. The xerostomaic condition may be induced by a clinical therapy, including a cancer therapy, medication, diet or result from tissue senescence or an organic disorder of the salivary glands.

In one preferred embodiment, the morphogen or morphogen-stimulating agent is administered directly to the individual by topical administration, e.g., by coating the desired surface to be treated with the morphogen or morphogen-stimulating agent. For example, the therapeutic agent may be provided to the desired site by consuming a formulation containing the therapeutic agent in association with a compound capable of coating or adhering to the luminal lining surface. Such compounds include pectin-containing or sucralfate solutions such as are used in commericially available antacid preparations such as "MILK OF MAGNESIA" and "KAOPECTATE." For oral mucositis treatments, the agent may be provided in an oral rinse similar to a mouth wash that is swished around the mouth to coat the affected tissue, or disposed in a slow-dissolving lozenge or troche. Alternatively, the therapeutic agent may be provided to the site by physically applying or painting a formulation containing the morphogen or morphogen-stimulating agent to the site. Compositions for topical administration also may include a liquid adhesive to adhere the morphogen or morphogen-stimulating agent to the tissue surface. Useful adhesives include "ZILACTIN," as is used in "ORABASE," hydroxypropylcellulose, and fibrinogen/thrombin solutions. Another potentially useful adhesive is the bioadhesive described in U.S. Pat. No. 5,197,973, the disclosure of which is incorporated herein by reference. The liquid adhesive may be painted onto the tissue surface, or formulated into an aerosol that is sprayed onto the affected tissue. For treatment of the lower bowel, the therapeutic agent also may be provided rectally, e.g., by suppository, foam, liquid ointment or cream, particularly for the treatment of ulcerations of the ileum and colon. In another embodiment of the invention, the morphogen or morphogen-stimulating agent is provided systemically, e.g., by parenteral administration.

In any treatment method of the invention, "administration of morphogen" refers to the administration of the morphogen, either alone or in combination with other molecules. For example, the mature form of the morphogen may be provided in association with its precursor "pro" domain, which is known to enhance the solubility of the protein in physiological solutions. Other useful molecules known to enhance protein solubility include casein and other milk components, as well as various serum proteins. Additional useful molecules which may be associated with the morphogen or morphogen-stimulating agent include tissue targeting molecules capable of directing the morphogen or morphogen-stimulating agent to epithelial mucosa tissue. Tissue targeting molecules envisioned to be useful in the treatment protocols of this invention include antibodies, antibody fragments or other binding proteins which interact specifically with surface molecules on GI barrier tissue cells. Non-steroidal anti-inflammatory agents which typically are targeted to inflamed tissue also may be used.

Still another useful tissue targeting molecule may comprise part or all of the morphogen precursor "pro" domain. Under naturally occurring conditions, the endogenous morphogens described herein may be synthesized in other tissues and transported to target tissue after secretion from the synthesizing tissue. For example, while the protein has been shown to be active in bone tissue, the primary source of OP-1 synthesis appears to be the tissue of the urogenic system (e.g., renal and bladder tissue), with secondary expression levels occurring in the brain, heart and lungs (see below.) Moreover, the protein has been identified in serum, saliva and various milk forms. In addition, the secreted form of the protein comprises the mature dimer in association with the pro domain of the intact morphogen sequence. Accordingly, the associated morphogen pro domains may act to target specific morphogens to different tissues in vivo.

Associated tissue targeting or solubility-enhancing molecules also may be covalently linked to the morphogen using standard chemical means, including acid-labile linkages, which likely will be preferentially cleaved in the acidic environment of the GI tract.

Finally, the morphogens or morphogen-stimulating agents provided herein also may be administered in combination with other molecules ("cofactors"), known to be beneficial in ulcer treatments, particularly cofactors capable of mitigating or alleviating symptoms typically associated with ulcerated tissue damage and/or loss. Examples of such cofactors include, analgesics/anesthetics such as xylocaine, and benzocaine; antiseptics such as chlorohexidine; antibacterial, anti-viral and anti-fungal agents, including aminoglycosides, macrolides, penicillins, and cephalosporins; and antacids or antisecretory agents such as cimetidine or ramitidine.

Among the morphogens useful in this invention are proteins originally identified as osteogenic proteins, such as the OP-1, OP-2 and CBMP2 proteins, as well as amino acid sequence-related proteins such as DPP (from Drosophila), Vgl (from Xenopus), Vgr-1 (from mouse, see U.S. 5,011, 691 to Oppermann et al.), GDF-1 (from mouse, see Lee (1991) PNAS 88:4250–4254), all of which are presented in Table II and Seq. ID Nos.5–14), and the recently identified 60A protein (from Drosophila, Seq. ID No. 24, see Wharton et al. (1991) PNAS 88:9214–9218.) The members of this family, which include members of the TGF-β super-family of proteins, share substantial amino acid sequence homology in their C-terminal regions. The proteins are translated as a precursor, having an N-terminal signal peptide sequence, typically less than about 30 residues, followed by a "pro" domain that is cleaved to yield the mature sequence. The "pro" form of the protein includes the pro domain and the mature domain, and forms a soluble species that appears to be the primary form secreted from cultured mammalian cells. The signal peptide is cleaved rapidly upon translation, at a cleavage site that can be predicted in a given sequence using the method of Von Heijne ((1986) *Nucleic Acids Research* 14:4683–4691.) Table I, below, describes the various morphogens identified to date, including their nomenclature as used herein, their Seq. ID references, and publication sources for the amino acid sequences for the full length proteins not included in the Seq. Listing. The disclosure of these publications is incorporated herein by reference.

TABLE I

| | |
|---|---|
| "OP-1" | Refers generically to the group of morphogenically active proteins expressed from part or all of a DNA sequence encoding OP-1 protein, including allelic and species variants thereof, e.g., human OP-1 ("hOP-1", Seq. ID No. 5, mature protein amino acid sequence), or mouse OP-1 ("mOP-1", Seq. ID No. 6, mature protein amino acid sequence.) The conserved seven cysteine skeleton is defined by residues 38 to 139 of Seq. ID. Nos. 5 and 6. The cDNA sequences and the amino acids encoding the full length proteins are provided in Seq. Id Nos. 16 and 17 (hOP1) and Seq. ID Nos. 18 and 19 (mOP1.) The mature proteins are defined by residues 293–431 (hOP1) and 292–430 (mOP1). The "pro" regions of the proteins, cleaved to yield the mature, morphogenically active proteins are defined essentially by residues 30–292 (hOP1) and residues 30–291 (mOP1). |
| "OP-2" | refers generically to the group of active proteins expressed from part or all of a DNA sequence encoding OP-2 protein, including allelic and species variants thereof, e.g., human OP-2 ("hOP-2", Seq. ID No. 7, mature protein amino acid sequence) or mouse OP-2 ("mOP-2", Seq. ID No. 8, mature protein amino acid sequence). The conserved seven cysteine skeleton is defined by residues 38 to 139 of Seq. ID Nos. 7 and 8. The cDNA sequences and the amino acids encoding the full length proteins are provided in Seq. ID Nos. 20 and 21 (hOP2) and Seq. ID Nos. 22 and 23 (mOP2.) The mature proteins are defined essentially by residues 264–402 (hOP2) and 261–399 (mOP2). The "pro" regions of the proteins, cleaved to yield the mature, morphogenically active proteins likely are defined essentially by residues 18–263 (hOP2) and residues 18–260 (mOP2). (Another cleavage site also occurs 21 residues upstream for hOP-2 protein.) |
| "CBMP2" | refers generically to the morphogenically active proteins expressed from a DNA sequence encoding the CBMP2 proteins, including allelic and species variants thereof, e.g., human CBMP2A ("CBMP2A (fx)", Seq ID No. 9) or human CBMP2B DNA ("CBMP2B (fx)", Seq. ID No. 10). The amino acid sequence for the full length proteins, referred to in the literature as BMP2A and BMP2B, or BMP2 and BMP4, appear in Wozney, et al. (1988) Science 242:1528–1534. The pro domain for BMP2 (BMP2A) likely includes residues 25–248 or 25–282; the mature protein, residues 249–396 or 283–396. The pro domain for BMP4 (BMP2B) likely includes residues 25–256 or 25–292; the mature protein, residues 257–408 or 293–408. |
| "DPP (fx)" | refers to protein sequences encoded by the Drosophila DPP gene and defining the conserved seven cysteine skeleton (Seq. ID No. 11). The amino acid sequence for the full length protein appears in Padgett, et al (1987) Nature 325: 81–84. The pro domain likely extends from the signal peptide cleavage site to residue 456; the mature protein likely is defined by residues 457–588. |

TABLE I-continued

| | |
|---|---|
| "Vgl (fx)" | refers to protein sequences encoded by the Xenopus Vgl gene and defining the conserved seven cysteine skeleton (Seq. ID No. 12). The amino acid sequence for the full length protein appears in Weeks (1987) Cell 51: 861–867. The pro domain likely extends from the signal peptide cleavage site to residue 246; the mature protein likely is defined by residues 247–360. |
| "Vgr-1 (fx)" | refers to protein sequences encoded by the murine Vgr-1 gene and defining the conserved seven cysteine skeleton (Seq. ID No. 13). The amino acid sequence for the full length protein appears in Lyons, et al, (1989) PNAS 86: 4554–4558. The pro domain likely extends from the signal peptide cleavage site to residue 299; the mature protein likely is defined by residues 300–438. |
| "GDF-1 (fx)" | refers to protein sequences encoded by the human GDF-1 gene and defining the conserved seven cysteine skeleton (Seq. ID No. 14). The cDNA and encoded amino sequence for the full length protein is provided in Seq. ID. No. 32. The pro domain likely extends from the signal peptide cleavage site to residue 214; the mature protein likely is defined by residues 215–372. |
| "60A" | refers generically to the morphogenically active proteins expressed from part or all of a DNA sequence (from the Drosophila 60A gene) encoding the 60A proteins (see Seq. ID No. 24 wherein the cDNA and encoded amino acid sequence for the full length protein is provided). "60A (fx)" refers to the protein sequences defining the conserved seven cysteine skeleton (residues 354 to 455 of Seq. ID No. 24.) The pro domain likely extends from the signal peptide cleavage site to residue 324; the mature protein likely is defined by residues 325–455. |
| "BMP3 (fx)" | refers to protein sequences encoded by the human BMP3 gene and defining the conserved seven cysteine skeleton (Seq. ID No. 26). The amino acid sequence for the full length protein appears in Wozney et al. (1988) Science 242: 1528–1534. The pro domain likely extends from the signal peptide cleavage site to residue 290; the mature protein likely is defined by residues 291–472. |
| "BMP5 (fx)" | refers to protein sequences encoded by the human BMP5 gene and defining the conserved seven cysteine skeleton (Seq. ID No. 27). The amino acid sequence for the full length protein appears in Celeste, et al. (1991) PNAS 87: 9843–9847. The pro domain likely extends from the signal peptide cleavage site to residue 316; the mature protein likely is defined by residues 317–454. |
| "BMP6 (fx)" | refers to protein sequences encoded by the human BMP6 gene and defining the conserved seven cysteine skeleton (Seq. ID No. 28). The amino acid sequence for the full length protein appears in Celeste, et al. (1990) PNAS 87: 9843–5847. The pro domain likely extends from the signal peptide cleavage site to residue 374; the mature sequence likely includes residues 375–513. |

The OP-2 proteins have an additional cysteine residue in this region (e.g., see residue 41 of Seq. ID Nos. 7 and 8), in addition to the conserved cysteine skeleton in common with the other proteins in this family. The GDF-1 protein has a four amino acid insert within the conserved skeleton (residues 44–47 of Seq. ID No. 14) but this insert likely does not interfere with the relationship of the cysteines in the folded structure. In addition, the CBMP2 proteins are missing one amino acid residue within the cysteine skeleton.

The morphogens are inactive when reduced, but are active as oxidized homodimers and when oxidized in combination with other morphogens of this invention. Thus, as defined herein, a morphogen is a dimeric protein comprising a pair of polypeptide chains, wherein each polypeptide chain comprises at least the C-terminal six cysteine skeleton defined by residues 43–139 of Seq. ID No. 5, including functionally equivalent arrangements of these cysteines (e.g., amino acid insertions or deletions which alter the linear arrangement of the cysteines in the sequence but not their relationship in the folded structure), such that, when the polypeptide chains are folded, the dimeric protein species comprising the pair of polypeptide chains has the appropriate three-dimensional structure, including the appropriate intra- or inter-chain disulfide bonds such that the protein is capable of acting as a morphogen as defined herein. Specifically, the morphogens generally are capable of all of the following biological functions in a morphogenically permissive environment: stimulating proliferation of progenitor cells; stimulating the differentiation of progenitor cells; stimulating the proliferation of differentiated cells; and supporting the growth and maintenance of differentiated cells, including the "redifferentiation" of transformed cells. In addition, it is also anticipated that these morphogens are capable of inducing redifferentiation of committed cells under appropriate environmental conditions.

In one preferred aspect, the morphogens of this invention comprise one of two species of generic amino acid sequences: Generic Sequence 1 (Seq- ID No. 1) or Generic Sequence 2 (Seq. ID No. 2); where each Xaa indicates one of the 20 naturally-occurring L-isomer, α-amino acids or a derivative thereof. Generic Sequence 1 comprises the conserved six cysteine skeleton and Generic Sequence 2 comprises the conserved six cysteine skeleton plus the additional cysteine identified in OP-2 (see residue 36, Seq. ID No. 2). In another preferred aspect, these sequences further comprise the following additional sequence at their N-terminus:

```
Cys  Xaa  Xaa  Xaa  Xaa   (Seq. ID No. 15)
 1              5
```

Preferred amino acid sequences within the foregoing generic sequences include: Generic Sequence 3 (Seq. ID No. 3), Generic Sequence 4 (Seq. ID No. 4), Generic Sequence 5 (Seq. ID No. 30) and Generic Sequence 6 (Seq. ID No. 31), listed below. These Generic Sequences accommodate the homologies shared among the various preferred members of this morphogen family identified in Table II, as well as the amino acid sequence variation among them. Specifically, Generic Sequences 3 and 4 are composite amino acid sequences of the following proteins presented in Table II and identified in Seq. ID Nos. 5–14: human OP-1 (hOP-1, Seq. ID Nos. 5 and 16–17), mouse OP-1 (mOP-1, Seq. ID Nos. 6 and 18–19), human and mouse OP-2 (Seq. ID Nos. 7, 8, and 20–22), CBMP2A (Seq. ID No. 9), CBMP2B (Seq. ID No. 10), DPP (from Drosophila, Seq. ID No. 11), Vgl. (from Xenopus, Seq. ID No. 12), Vgr-1 (from mouse, Seq. ID No. 13), and GDF-1 (from mouse, Seq. ID No. 14.) The generic sequences include both the amino acid identity shared by the sequences in Table II, as well as alternative residues for the variable positions within the sequence. Note that these generic sequences allow for an additional cysteine at position 41 or 46 in Generic Sequences 3 or 4, respectively, providing an appropriate cysteine skeleton where inter- or intramolecular disulfide bonds can form, and contain certain critical amino acids which influence the tertiary structure of the proteins.

Generic Sequence 3 (SEQ ID NO. 3)

```
         Leu  Tyr  Val  Xaa  Phe
          1              5
Xaa Xaa Xaa Gly Trp Xaa Xaa Trp Xaa
                    10
   Xaa Ala Pro Xaa Gly Xaa Xaa Ala
   15                 20
   Xaa Tyr Cys Xaa Gly Xaa Cys Xaa
                25                30
      Xaa Pro Xaa Xaa Xaa Xaa Xaa
                    35
   Xaa Xaa Xaa Asn His Ala Xaa Xaa
            40                  45
   Xaa Xaa Leu Xaa Xaa Xaa Xaa Xaa
                    50
   Xaa Xaa Xaa Xaa Xaa Xaa Xaa Cys
        55                      60
   Cys Xaa Pro Xaa Xaa Xaa Xaa Xaa
                    65
      Xaa Xaa Xaa Leu Xaa Xaa Xaa
         70                 75
   Xaa Xaa Xaa Xaa Val Xaa Leu Xaa
                    80
   Xaa Xaa Xaa Xaa Met Xaa Val Xaa
   85                      90
            Xaa Cys Gly Cys Xaa
                       95
``` wherein each Xaa is independently selected from a group of one or more specified amino acids defined as follows: "Res." means "residue" and Xaa at res.4=(Ser, Asp or Glu); Xaa at res.6=(Arg, Gln, Ser or Lys); Xaa at res.7=(Asp or Glu); Xaa at res.8=(Leu or Val); Xaa at res.11=(Gln, Leu, Asp, His or Asn); Xaa at res.12=(Asp, Arg or Asn); Xaa at res.14=(Ile or Val); Xaa at res.15=(Ile or Val); Xaa at res.18=(Glu, Gln, Leu, Lys, Pro or Arg); Xaa at res.20=(Tyr or Phe); Xaa at res.21=(Ala, Ser, Asp, Met, His, Leu or Gln); Xaa at res.23=(Tyr, Asn or Phe); Xaa at res.26=(Glu, His, Tyr, Asp or Gln); Xaa at res.28=(Glu, Lys, Asp or Gln); Xaa at res.30=(Ala, Set, Pro or Gln); Xaa at res.31=(Phe, Leu or Tyr); Xaa at res.33=(Leu or Val); Xaa at res.34=(Asn, Asp, Ala or Thr); Xaa at res.35=(Ser, Asp, Glu, Leu or Ala); Xaa at res.36=(Tyr, Cys, His, Ser or Ile); Xaa at res.37=(Met, Phe, Gly or Leu); Xaa at res.38=(Ash or Ser); Xaa at res.39=(Ala, Ser or Gly); Xaa at res.40=(Thr, Leu or Ser); Xaa at res.44=(Ile or Val); Xaa at res.45=(Val or Leu); Xaa at res.46=(Gln or Arg); Xaa at res.47=(Thr, Ala or Ser); Xaa at res.49=(Val or Met); Xaa at res.50=(His or Asn); Xaa at res.51=(Phe, Leu, Asn, Ser, Ala or Val); Xaa at res.52=(Ile, Met, Asn, Ala or Val); Xaa at res.53=(Asn, Lys, Ala or Glu); Xaa at res.54=(Pro or Ser); Xaa at res.55=(Glu, Asp, Asn, or Gly); Xaa at res.56=(Thr, Ala, Val, Lys, Asp, Tyr, Ser or Ala); Xaa at res.57=(Val, Ala or Ile); Xaa at res.58=(Pro or Asp); Xaa at res.59=(Lys or Leu); Xaa at res.60=(Pro or Ala); Xaa at res.63=(Ala or Val); Xaa at res.65=(Thr or Ala); Xaa at res.66=(Gln, Lys, Arg or Glu); Xaa at res.67=(Leu, Met or Val); Xaa at res.68=(Asn, Ser or Asp); Xaa at res.69=(Ala, Pro or Ser); Xaa at res.70=(Ile, Thr or Val); Xaa at res.71=(Ser or Ala); Xaa at res.72=(Val or Met); Xaa at res.74=(Tyr or Phe); Xaa at res.75=(Phe, Tyr or Leu); Xaa at res.76=(Asp or Asn); Xaa at res.77=(Asp, Glu, Asn or Ser); Xaa at res.78=(Ser, Gln, Asn or Tyr); Xaa at res.79=(Ser, Asn, Asp or Glu); Xaa at res.80=(Asn, Thr or Lys); Xaa at res.82=(Ile or Val); Xaa at res.84=(Lys or Arg); Xaa at res.85=(Lys, Asn, Gln or His); Xaa at res.86=(Tyr or His); Xaa at res.87=(Arg, Gln or Glu); Xaa at res.88=(Asn, Glu or Asp); Xaa at res.90=(Val, Thr or Ala); Xaa at res.92=(Arg, Lys, Val, Asp or Glu); Xaa at res.93=(Ala, Gly or Glu); and Xaa at res.97=(His or Arg);

Generic Sequence 4 (SEQ ID NO: 4)

Cys Xaa Xaa Xaa Xaa Leu Tyr Val Xaa Phe
1           5                        10
Xaa Xaa Xaa Gly Trp Xaa Xaa Trp Xaa
              15
Xaa Ala Pro Xaa Gly Xaa Xaa Ala
20                 25
Xaa Tyr Cys Xaa Gly Xaa Cys Xaa
          30                      35
Xaa Pro Xaa Xaa Xaa Xaa Xaa
                40
Xaa Xaa Xaa Asn His Ala Xaa Xaa
        45              50
Xaa Xaa Leu Xaa Xaa Xaa Xaa Xaa
               55
Xaa Xaa Xaa Xaa Xaa Xaa Xaa Cys
60                              65
Cys Xaa Pro Xaa Xaa Xaa Xaa Xaa
              70
Xaa Xaa Xaa Leu Xaa Xaa Xaa
75                    80
Xaa Xaa Xaa Xaa Val Xaa Leu Xaa
            85
Xaa Xaa Xaa Xaa Met Xaa Val Xaa
90                      95
Xaa Cys Gly Cys Xaa
100 wherein each Xaa is independently selected from a group of one or more specified amino acids as defined by the following: "Res." means "residue" and Xaa at res.2=(Lys or Arg); Xaa at res.3=(Lys or Arg); Xaa at res.4=(His or Arg); Xaa at res.5=(Glu, Ser, His, Gly, Arg or Pro); Xaa at res.9=(Ser, Asp or Glu); Xaa at res.11=(Arg, Gln, Ser or Lys); Xaa at res.12=(Asp or Glu); Xaa at res.13=(Leu or Val); Xaa at res.16=(Gln, Leu, Asp, His or Asn); Xaa at res.17=(Asp, Arg, or Asn); Xaa at res.19=(Ile or Val); Xaa at res.20=(Ile or Val); Xaa at res.23=(Glu, Gln, Leu, Lys, Pro or Arg); Xaa at res.25=(Tyr or Phe); Xaa at res.26=(Ala, Ser, Asp, Met, His, Leu, or Gln); Xaa at res.28=(Tyr, Asn or Phe); Xaa at res.31=(Glu, His, Tyr, Asp or Gln); Xaa at res.33=Glu, Lys, Asp or Gln); Xaa at res.35=(Ala, Ser or Pro); Xaa at res.36=(Phe, Leu or Tyr); Xaa at res.38=(Leu or Val); Xaa at res.39=(Asn, Asp, Ala or Thr); Xaa at res.40=(Ser, Asp, Glu, Leu or Ala); Xaa at res.41=(Tyr, Cys, His, Set or Ile); Xaa at res.42=(Met, Phe, Gly or Leu); Xaa at res.44=(Ala, Ser or Gly); Xaa at res.45=(Thr, Leu or Ser); Xaa at res.49=(Ile or Val); Xaa at res.50=(Val or Leu); Xaa at res.51=(Gln or Arg); Xaa at res.52=(Thr, Ala or Ser); Xaa at res.54=(Val or Met); Xaa at res.55=(His or Asn); Xaa at res.56=(Phe, Leu, Asn, Ser, Ala or Val); Xaa at res.57=(Ile, Met, Asn, Ala or Val); Xaa at res.58=(Asn, Lys, Ala or Glu); Xaa at res.59=(Pro or Ser); Xaa at res.60=(Glu, Asp, or Gly); Xaa at res.61=(Thr, Ala, Val, Lys, Asp, Tyr, Set or Ala); Xaa at res.62=(Val, Ala or Ile); Xaa at res.63=(Pro or Asp); Xaa at res.64=(Lys or Leu); Xaa at res.65=(Pro or Ala); Xaa at res.68=(Ala or Val); Xaa at res.70=(Thr or Ala); Xaa at res.71=(Gln, Lys, Arg or Glu); Xaa at res.72=(Leu, Met or Val); Xaa at res.73=(Asn, Ser or Asp); Xaa at res.74=(Ala, Pro or Ser); Xaa at res.75=(Ile, Thr or Val); Xaa at res.76=(Ser or Ala); Xaa at res.77=(Val or Met); Xaa at res.79=(Tyr or Phe); Xaa at res.80=(Phe, Tyr or Leu); Xaa at res.81=(Asp or Asn); Xaa at res.82=(Asp, Glu, Asn or Ser); Xaa at res.83=(Ser, Gln, Asn or Tyr); Xaa at res.84=(Ser, Asn, Asp or Glu); Xaa at res.85=(Asn, Thr or Lys); Xaa at res.87=(Ile or Val); Xaa at res.89=(Lys or Arg); Xaa at res.90=(Lys, Ash, Gln or His); Xaa at res.91=(Tyr or His); Xaa at res.92=(Arg, Gln or Glu); Xaa at res.93=(Asn, Glu or Asp); Xaa at res.95=(Val, Thr or Ala); Xaa at res.97=(Arg, Lys, Val, Asp or Glu); Xaa at res.98=(Ala, Gly or Glu); and Xaa at res.102=(His or Arg).

Similarly, Generic Sequence 5 (Seq. ID No. 30) and Generic Sequence 6 (Seq. ID No. 31) accommodate the homologies shared among all the morphogen protein family members identified in Table II. Specifically, Generic Sequences 5 and 6 are composite amino acid sequences of human OP-1 (hOP-1, Seq. ID Nos. 5 and 16–17), mouse OP-1 (mOP-1, Seq. ID Nos. 6 and 18–19), human and mouse OP-2 (Seq. ID Nos. 7, 8, and 20–22), CBMP2A (Seq. ID No. 9), CBMP2B (Seq. ID No. 10), DPP (from Drosophila, Seq. ID No. 11), Vgl, (from Xenopus, Seq. ID No. 12), Vgr-1 (from mouse, Seq. ID No. 13), and GDF-1 (from mouse, Seq. ID No. 14), human BMP3 (Seq. ID No. 26), human BMP5 (Seq. ID No. 27), human BMP6 (Seq. ID No. 28) and 60(A) (from Drosophila, Seq. ID Nos. 24–25). The generic sequences include both the amino acid identity shared by these sequences in the C-terminal domain, defined by the six and seven cysteine skeletons (Generic Sequences 5 and 6, respectively), as well as alternative residues for the variable positions within the sequence. As for Generic Sequences 3 and 4, Generic Sequences 5 and 6 allow for an additional cysteine at position 41 (Generic Sequence 5) or position 46 (Generic Sequence 6), providing an appropriate cysteine skeleton where inter- or intramolecular disulfide bonds can form, and containing certain critical amino acids which influence the tertiary structure of the proteins.

Generic Sequence 5 (SEQ ID NO: 5)

Leu Xaa Xaa Xaa Phe
1                  5
Xaa Xaa Xaa Gly Trp Xaa Xaa Trp Xaa
              10
Xaa Xaa Pro Xaa Xaa Xaa Xaa Ala
15                 20
Xaa Tyr Cys Xaa Gly Xaa Cys Xaa
          25                      30
Xaa Pro Xaa Xaa Xaa Xaa Xaa
                35
Xaa Xaa Xaa Asn His Ala Xaa Xaa
        40              45
Xaa Xaa Xaa Xaa Xaa Xaa Xaa
               50
Xaa Xaa Xaa Xaa Xaa Xaa Xaa Cys
55                              60
Cys Xaa Pro Xaa Xaa Xaa Xaa Xaa
              65
Xaa Xaa Xaa Leu Xaa Xaa Xaa
70                    75
Xaa Xaa Xaa Xaa Val Xaa Leu Xaa
            80
Xaa Xaa Xaa Xaa Met Xaa Val Xaa
85                      90
Xaa Cys Xaa Cys Xaa
95 wherein each Xaa is independently selected from a group of one or more specified amino acids defined as follows: "Res." means "residue" and Xaa at res.2=(Tyr or Lys); Xaa at res.3=Val or Ile); Xaa at res.4=(Ser, Asp or Glu); Xaa at res.6=(Arg, Gln, Ser, Lys or Ala); Xaa at res.7=(Asp, Glu or Lys); Xaa at res.8=(Leu, Val or Ile); Xaa at res.11=(Gln, Leu, Asp, His, Asn or Ser); Xaa at res.12=(Asp, Arg, Asn or Glu); Xaa at res.14=(Ile or Val); Xaa at res.15=(Ile or Val); Xaa at res.16 (Ala or Ser); Xaa at res.18=(Glu, Gln, Leu, Lys, Pro or Arg); Xaa at res.19=(Gly or Ser); Xaa at res.20=(Tyr or Phe); Xaa at res.21=(Ala, Ser, Asp, Met, His, Gln, Leu or Gly); Xaa at res.23=(Tyr, Asn or Phe); Xaa at res.26=(Glu, His, Tyr, Asp, Gln or Ser); Xaa at res.28=(Glu, Lys, Asp, Gln or Ala); Xaa at res.30=(Ala, Ser, Pro, Gln or Asn); Xaa at res.31=(Phe, Leu or Tyr); Xaa at res.33=(Leu, Val or Met); Xaa at res.34=(Asn, Asp, Ala, Thr or Pro); Xaa at res.35= (Ser, Asp, Glu, Leu, Ala or Lys); Xaa at res.36=(Tyr, Cys, His, Ser or Ile); Xaa at res.37=(Met, Phe, Gly or Leu); Xaa at res.38=(Ash, Ser or Lys); Xaa at res.39=(Ala, Ser, Gly or Pro); Xaa at res.40=(Thr, Leu or Ser); Xaa at res.44=(Ile, Val or Thr); Xaa at res.45=(Val, Leu or Ile); Xaa at res.46=(Gln or Arg); Xaa at res.47=(Thr, Ala or Ser); Xaa at res.48=(Leu or Ile); Xaa at res.49=(Val or Met); Xaa at res.50=(His, Asn or Arg); Xaa at res.51=(Phe, Leu, Asn, Ser, Ala or Val); Xaa at res.52=(Ile, Met, Asn, Ala, Val or Leu); Xaa at res.53=(Asn, Lys, Ala, Glu, Gly or Phe); Xaa at res.54=(Pro, Ser or Val); Xaa at res.55=(Glu, Asp, Asn, Gly, Val or Lys); Xaa at res.56=(Thr, Ala, Val, Lys, Asp, Tyr, Ser, Ala, Pro or His); Xaa at res.57=(Val, Ala or Ile); Xaa at res.58=(Pro or Asp); Xaa at res.59=(Lys, Leu or Glu); Xaa at res.60=(Pro or Ala); Xaa at res.63=(Ala or Val); Xaa at res.65=(Thr, Ala or Glu); Xaa at res.66=(Gln, Lys, Arg or Glu); Xaa at res.67=(Leu, Met or Val); Xaa at res.68=(Asn, Ser, Asp or Gly); Xaa at res.69=(Ala, Pro or Ser); Xaa at res.70=(Ile, Thr, Val or Leu); Xaa at res.71=(Ser, Ala or Pro); Xaa at res.72=(Val, Met or Ile); Xaa at res.74=(Tyr or Phe); Xaa at res.75=(Phe, Tyr, Leu or His); Xaa at res.76=(Asp, Asn or Leu); Xaa at res.77=(Asp, Glu, Asn or Ser); Xaa at res.78=(Ser, Gln, Ash, Tyr or Asp); Xaa at res.79=(Ser, Asn, Asp, Glu or Lys); Xaa at res.80=(Asn, Thr or Lys); Xaa at res.82=(Ile, Val or Asn); Xaa at res.84=(Lys or Arg); Xaa at res.85=(Lys, Asn, Gln, His or Val); Xaa at res.86=(Tyr or His); Xaa at res.87=(Arg, Gln, Glu or Pro); Xaa at res.88=(Asn, Glu or Asp); Xaa at res.90=(Val, Thr, Ala or Ile); Xaa at res.92=(Arg, Lys, Val, Asp or Glu); Xaa at res.93=(Ala, Gly, Glu or Ser); Xaa at res.95=(Gly or Ala) and Xaa at res.97=(His or Arg).

Generic Sequence 6

```
Cys Xaa Xaa Xaa Xaa Leu Xaa Xaa Xaa Phe
 1               5                    10
    Xaa Xaa Xaa Gly Trp Xaa Xaa Trp Xaa
                     15
    Xaa Xaa Pro Xaa Xaa Xaa Xaa Ala
    20                  25
    Xaa Tyr Cys Xaa Gly Xaa Cys Xaa
                30                  35
        Xaa Pro Xaa Xaa Xaa Xaa Xaa
                        40
    Xaa Xaa Xaa Asn His Ala Xaa Xaa
                45                  50
    Xaa Xaa Xaa Xaa Xaa Xaa Xaa Xaa
                    55
    Xaa Xaa Xaa Xaa Xaa Xaa Xaa Cys
    60                          65
    Cys Xaa Pro Xaa Xaa Xaa Xaa Xaa
                    70
        Xaa Xaa Xaa Leu Xaa Xaa Xaa
        75                      80
    Xaa Xaa Xaa Xaa Val Xaa Leu Xaa
                    85
    Xaa Xaa Xaa Xaa Met Xaa Val Xaa
    90                      95
            Xaa Cys Xaa Cys Xaa
                    100
``` wherein each Xaa is independently selected from a group of one or more specified amino acids as defined by the following: "Res." means "residue" and Xaa at res.2=(Lys, Arg, (Lys, Arg, Ala or Gln); Xaa at res.3=(Lys, Arg or Met); Xaa at res.4=(His, Arg or Gln); Xaa at res.5=(Glu, Set, His, Gly, Arg, Pro, Thr, or Tyr); Xaa at res.7=(Tyr or Lys); Xaa at res.8=(Val or Ile); Xaa at res.9=(Ser, Asp or Glu); Xaa at res.11=(Arg, Gln, Set, Lys or Ala); Xaa at res.12=(Asp, Glu, or Lys); Xaa at res.13=(Leu, Val or Ile); Xaa at res.16=(Gln, Leu, Asp, His, Asn or Ser); Xaa at res.17=(Asp, Arg, Asn or Glu); Xaa at res.19=(Ile or Val); Xaa at res.20=(Ile or Val); Xaa at res.21=(Ala or Ser); Xaa at res.23=(Glu, Gln, Leu, Lys, Pro or Arg); Xaa at res.24=(Gly or Ser); Xaa at res.25=(Tyr or Phe); Xaa at res.26=(Ala, Ser, Asp, Met, His, Gln, Leu, or Gly); Xaa at res.28=(Tyr, Asn or Phe); Xaa at res.31=(Glu, His, Tyr, Asp, Gln or Ser); Xaa at res.33=Glu, Lys, Asp, Gln or Ala); Xaa at res.35=(Ala, Ser, Pro, Gln or Asn); Xaa at res.36=(Phe, Leu or Tyr); Xaa at res.38=(Leu, Val or Met); Xaa at res.39=(Asn, Asp, Ala, Thr or Pro); Xaa at res.40=(Ser, Asp, Glu, Leu, Ala or Lys); Xaa at res.41=(Tyr, Cys, His, Set or Ile); Xaa at res.42=(Met, Phe, Gly or Leu); Xaa at res.43=(Asn, Ser or Lys); Xaa at res.44=(Ala, Ser, Gly or Pro); Xaa at res.45=(Thr, Leu or Ser); Xaa at res.49=(Ile, Val or Thr); Xaa at res.50=(Val, Leu or Ile); Xaa at res.51=(Gln or Arg); Xaa at res.52=(Thr, Ala or Ser); Xaa at res.53=(Leu or Ile); Xaa at res.54=(Val or Met); Xaa at res.55=(His, Asn or Arg); Xaa at res.56=(Phe, Leu, Asn, Ser, Ala or Val); Xaa at res.57=(Ile, Met, Ash, Ala, Val or Leu); Xaa at res.58=(Asn, Lye, Ala, Glu, Gly or Phe); Xaa at res.59=(Pro, Ser or Val); Xaa at res.60=(Glu, Asp, Gly, Val or Lys); Xaa at res.61=(Thr, Ala, Val, Lys, Asp, Tyr, Ser, Ala, Pro or His); Xaa at res.62=(Val, Ala or Ile); Xaa at res.63=(Pro or Asp); Xaa at res.64=(Lys, Leu or Glu); Xaa at res.65=(Pro or Ala); Xaa at res.68=(Ala or Val); Xaa at res.70=(Thr, Ala or Glu); Xaa at res.71=(Gln, Lys, Arg or Glu); Xaa at res.72=(Leu, Met or Val); Xaa at res.73=(Asn, Ser, Asp or Gly); Xaa at res.74=(Ala, Pro or Ser); Xaa at res.75=(Ile, Thr, Val or Leu); Xaa at res.76=(Ser, Ala or Pro); Xaa at res.77=(Val, Met or Ile); Xaa at res.79=(Tyr or Phe); Xaa at res.80=(Phe, Tyr, Leu or His); Xaa at res.81=(Asp, Asn or Leu); Xaa at res.82=(Asp, Glu, Asn or Ser); Xaa at res.83=(Ser, Gln, Asn, Tyr or Asp); Xaa at res.84=(Ser, Asn, Asp, Glu or Lys); Xaa at res.85=(Asn, Thr or Lys); Xaa at res.87=(Ile, Val or Asn); Xaa at res.89=(Lys or Arg); Xaa at res.90=(Lys, Asn, Gln, His or Val); Xaa at res.91=(Tyr or His); Xaa at res.92=(Arg, Gln, Glu or Pro); Xaa at res.93=(Asn, Glu or Asp); Xaa at res.95=(Val, Thr, Ala or Ile); Xaa at res.97=(Arg, Lys, Val, Asp or Glu); Xaa at res.98=(Ala, Gly, Glu or Ser); Xaa at res.100=(Gly or Ala); and Xaa at res.102=(His or Arg).

Particularly useful sequences for use as morphogens in this invention include the C-terminal domains, e.g., the C-terminal 96-102 amino acid residues of Vgl, Vgr-1, DPP, OP-1, OP-2, CBMP-2A, CBMP-2B, GDF-1 (see Table II, below, and Seq. ID Nos. 5–14), as well as proteins comprising the C-terminal domains of 60A, BMP3, BMP5 and BMP6 (see Seq. ID Nos. 24–28), all of which include at least the conserved six or seven cysteine skeleton. In addition, biosynthetic constructs designed from the generic sequences, such as COP-1, 3–5, 7, 16, disclosed in U.S. Pat. No. 5,011,691, also are useful. Other sequences include the inhibins/activin proteins (see, for example, U.S. Pat. Nos. 4,968,590 and 5,011,691). Accordingly, other useful sequences are those sharing at least 70% amino acid sequence homology or "similarity", and preferably 80% homology or similarity with any of the sequences above. These are anticipated to include allelic and species variants and mutants, and biosynthetic muteins, as well as novel members of this morphogenic family of proteins. Particularly envisioned in the family of related proteins are those proteins exhibiting morphogenic activity and wherein the amino acid changes from the preferred sequences include conservative changes, e.g., those as defined by Dayoff et al., *Atlas of Protein Sequence and Structure*; vol. 5, Suppl. 3, pp. 345–362, (M. O. Dayoff, ed., Nat'l BioMed. Research Fdn., Washington, D.C. 1979). As used herein, potentially useful sequences are aligned with a known morphogen sequence using the method of Needleman et al. ((1970) *J. Mol. Biol.* 48:443–453) and identities calculated by the Align program (DNAstar, Inc.). "Homology" or "similarity" as used herein includes allowed conservative changes as defined by Dayoff et al.

The currently most preferred protein sequences useful as morphogens in this invention include those having greater than 60% identity, preferably greater than 65% identity, with the amino acid sequence defining the conserved six cysteine skeleton of hOP1 (e.g., residues 43–139 of Seq. ID No. 5). These most preferred sequences include both allelic and species variants of the OP-1 and OP-2 proteins, including the Drosophila 60A protein. Accordingly, in another preferred aspect of the invention, useful morphogens include active proteins comprising species of polypeptide chains having the generic amino acid sequence herein referred to as "OPX", which accommodates the homologies between the various identified species of OP1 and OP2 (Seq. ID No. 29).

The morphogens useful in the methods, composition and devices of this invention include proteins comprising any of the polypeptide chains described above, whether isolated from naturally-occurring sources, or produced by recombinant DNA or other synthetic techniques, and includes allelic and species variants of these proteins, naturally-occurring or biosynthetic mutants thereof, as well as various truncated and fusion constructs. Deletion or addition mutants also are envisioned to be active, including those which may alter the conserved C-terminal cysteine skeleton, provided that the alteration does not functionally disrupt the relationship of these cysteines in the folded structure. Accordingly, such active forms are considered the equivalent of the specifically described constructs disclosed herein. The proteins may include forms having varying glycosylation patterns, varying N-termini, a family of related proteins having regions of amino acid sequence homology, and active truncated or mutated forms of native or biosynthetic proteins, produced by expression of recombinant DNA in host cells.

The morphogenic proteins can be expressed from intact or truncated cDNA or from synthetic DNAs in procaryotic or eucaryotic host cells, and purified, cleaved, refolded, and dimerized to form morphogenically active compositions. Currently preferred host cells include *E. coli* or mammalian cells, such as CHO, COS or BSC cells. A detailed description of the morphogens useful in the methods, compositions and devices of this invention is disclosed in U.S. patent application Ser. Nos. 07/752,764, filed Aug. 30, 1991, and Ser. No. 07/667,274, filed Mar. 11, 1991, both abandoned and continued as pending U.S. patent application Ser. Nos. 08/404,113 and 08/396,684, the disclosures of which are incorporated herein by reference.

Thus, in view of this disclosure, skilled genetic engineers can isolate genes from cDNA or genomic libraries of various different species which encode appropriate amino acid sequences, or construct DNAs from oligonucleotides, and then can express them in various types of host cells, including both procaryotes and eucaryotes, to produce large quantities of active proteins capable of maintaining the integrity of the gastrointestinal tract luminal lining in individuals at risk for ulcer formation.

The foregoing and other objects, features and advantages of the present invention will be made more apparent from the following detailed description of the invention.

BRIEF DESCRIPTION OF THE DRAWINGS

The foregoing and other objects and features of this invention, as well as the invention itself, may be more fully understood from the following description, when read together with the accompanying drawings, in which.

DETAILED DESCRIPTION OF THE INVENTION

Figure 1:
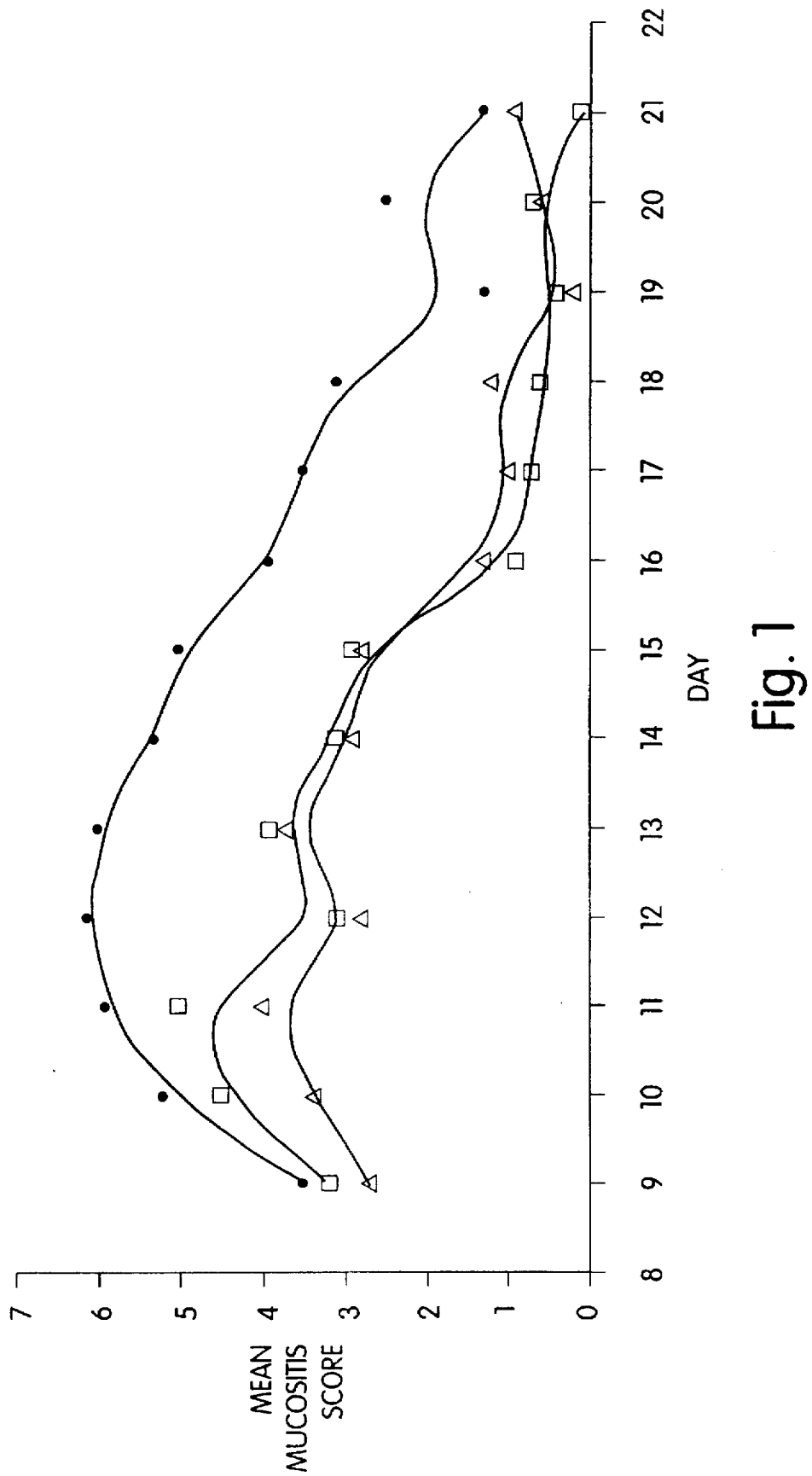
FIG. 1 graphs the effect of a morphogen (e.g., OP-1) and a placebo control on mucositic lesion formation.

It now has been discovered that the proteins described herein are effective agents for maintaining the integrity of the gastrointestinal tract luminal lining in a mammal. As described herein, these proteins ("morphogens") are capable of substantially inhibiting lesion formation in the basal epithelium, as well as stimulating the repair and regeneration the barrier tissue following ulceration. The proteins are capable of inhibiting epithelial cell proliferation and protecting the barrier tissue from damage. The proteins also are capable of inhibiting scar tissue formation that typically follows lesion formation in a mammal. In addition, the morphogens also can inhibit the inflammation normally associated with ulcerative diseases. The proteins may be used to treat ulcerative diseases of the gastrointestinal tract, including oral mucositis, peptic ulcers, ulcerative colitis, proctitis, and regional enteritis. The proteins also may be used to protect and/or treat GI tissue subject to damage in a xerostomaic individual. Finally, the morphogens may be administered as part of a chemical or radiotherapy to inhibit lesion formation in a patient undergoing cancer therapy and enhance the efficacy of the therapy thereby.

Provided below are detailed descriptions of suitable morphogens useful in the methods and compositions of this invention, as well as methods for their administration and application, and numerous, nonlimiting examples which demonstrate (1) the suitability of the morphogens described herein as therapeutic agents for maintaining the integrity of the gastrointestinal tract luminal lining, and (2) provide assays with which to test candidate morphogens and morphogen-stimulating agents for their efficacy. Specifically, the examples demonstrate the ability of morphogens to treat oral mucositis, duodenal ulcers, peptic ulcers, and ulcerative colitis (Examples 2–5), inhibit epithelial cell proliferation (Example 6), inhibit inflammation (Example 7) and inhibit scar tissue formation (Example 8). The Examples also describe methods for identifying morphogen-expressing tissue and screening for candidate morphogen stimulating agents (Examples 1, 2 and 10).

I. Useful Morphogens

As defined herein a protein is morphogenic if it is capable of inducing the developmental cascade of cellular and molecular events that culminate in the formation of new, organ-specific tissue and comprises at least the conserved C-terminal six cysteine skeleton or its functional equivalent (see supra). Details of how the morphogens useful in the method of this invention first were identified, as well as a description on how to make, use and test them for morphogenic activity, are disclosed in U.S. Ser. No. 07/667,274, filed Mar. 11, 1991 and U.S. Ser. No. 07/752,764, filed Aug. 30, 1991, both abandoned and continued as pending U.S. patent application Ser. Nos. 08/404,113 and 08/396,684, the disclosures of which are hereby incorporated by reference. As disclosed therein, the morphogens may be purified from naturally-sourced material or recombinantly produced from procaryotic or eucaryotic host cells, using the genetic sequences disclosed therein. Alternatively, novel morphogenic sequences may be identified following the procedures disclosed therein.

Particularly useful proteins include those which comprise the naturally derived sequences disclosed in Table II. Other useful sequences include 60A, BMP5, BMP6, BMP3, and biosynthetic constructs such as those disclosed in U.S. Pat. No. 5,011,691, the disclosure of which is incorporated herein by reference (e.g., COP-1, COP-3, COP-4, COP-5, COP-7, and COP-16).

Accordingly, the morphogens useful in the methods and compositions of this invention also may be described by morphogenically active proteins having amino acid sequences sharing 70% or, preferably, 80% homology (similarity) with any of the sequences described above, where "homology" is as defined herein above.

The morphogens useful in the method of this invention also can be described by any of the 6 generic sequences described herein (Generic Sequences 1, 2, 3, 4, 5 and 6). Generic sequences 1 and 2 also may include, at their N-terminus, the sequence Cys Xaa Xaa Xaa Xaa  (Seq. ID No. 15)
1             5

Table II, set forth below, compares the amino acid sequences of the active regions of native proteins that have been identified as morphogens, including human OP-1 (hOP-1, Seq. ID Nos. 5 and 16–17), mouse OP-1 (mOP-1, Seq. ID Nos. 6 and 18–19), human and mouse OP-2 (Seq. ID Nos. 7, 8, and 20–23), CBMP2A (Seq. ID No. 9), CBMP2B (Seq. ID No. 10), DPP (from Drosophila, Seq. ID No. 11), Vgl, (from Xenopus, Seq. ID No. 12), Vgr-1 (from mouse, Seq. ID No.13), and GDF-1 (from mouse, Seq. ID No. 14.) The sequences are aligned essentially following the method of Needleman et al. (1970) *J. Mol. Biol.*, 48:443–453, calculated using the Align Program (DNAstar, Inc.) In the table, three dots indicates that the amino acid in that position is the same as the amino acid in hOP-1. Three dashes indicates that no amino acid is present in that position, and are included for purposes of illustrating homologies. For example, amino acid residue 60 of CBMP-2A and CBMP-2B is "missing". Of course, both these amino acid sequences in this region comprise Asn-Ser (residues 58, 59), with CBMP-2A then comprising Lys and Ile, whereas CBMP-2B Comprises Ser and Ile.

TABLE II

| | | | | | | | | |
|---|---|---|---|---|---|---|---|---|
| hOP-1[1] | Cys | Lys | Lys | His | Glu | Leu | Tyr | Val |
| mOP-1[2] | ... | ... | ... | ... | ... | ... | ... | ... |
| hOP-2[3] | ... | Arg | Arg | ... | ... | ... | ... | ... |
| mOP-2[4] | ... | Arg | Arg | ... | ... | ... | ... | ... |
| DPP[5] | ... | Arg | Arg | ... | Ser | ... | ... | ... |
| Vgl[6] | ... | ... | Lys | Arg | His | ... | ... | ... |
| Vgr-1[7] | ... | ... | ... | ... | Gly | ... | ... | ... |
| CBMP-2A[8] | ... | ... | Arg | ... | Pro | ... | ... | ... |
| CBMP-2B[9] | ... | Arg | Arg | ... | Ser | ... | ... | . |
| GDF-1[10] | ... | Arg | Ala | Arg | Arg | ... | ... | ... |
| | 1 | | | | 5 | | | |
| hOP-1 | Ser | Phe | Arg | Asp | Leu | Gly | Trp | Gln | Asp |
| mOP-1 | ... | ... | ... | ... | ... | ... | ... | ... | ... |
| hOP-2 | ... | ... | Gln | ... | ... | ... | ... | Leu | ... |
| mOP-2 | Ser | ... | ... | ... | ... | ... | ... | Leu | ... |
| DPP | Asp | ... | Ser | ... | Val | ... | ... | Asp | ... |
| Vgl | Glu | ... | Lys | ... | Val | ... | ... | ... | Asn |
| Vgr-1 | ... | ... | Gln | ... | Val | ... | ... | ... | ... |
| CBMP-2A | Asp | ... | Ser | ... | Val | ... | ... | Asn | ... |
| CBMP-2B | Asp | ... | Ser | ... | Val | ... | ... | Asn | ... |
| GDF-1 | ... | ... | ... | Glu | Val | ... | ... | His | Arg |
| | | 10 | | | | | | 15 | |
| hOP-1 | Trp | Ile | Ile | Ala | Pro | Glu | Gly | Tyr | Ala |
| mOP-1 | ... | ... | ... | ... | ... | ... | ... | ... | ... |
| hOP-2 | ... | Val | ... | ... | ... | Gln | ... | ... | Ser |
| mOP-2 | ... | Val | ... | ... | ... | Gln | ... | ... | Ser |
| DPP | ... | ... | Val | ... | ... | Leu | ... | ... | Asp |
| Vgl | ... | Val | ... | ... | ... | Gln | ... | ... | Met |
| Vgr-1 | ... | ... | ... | ... | ... | Lys | ... | ... | ... |
| CBMP-2A | ... | ... | Val | ... | ... | Pro | ... | ... | His |
| CBMP-2B | ... | ... | Val | ... | ... | Pro | ... | ... | Gln |
| GDF-1 | ... | Val | ... | ... | ... | Arg | ... | Phe | Leu |
| | | | 20 | | | | | 25 | |
| hOP-1 | Ala | Tyr | Tyr | Cys | Glu | Gly | Glu | Cys | Ala |
| mOP-1 | ... | ... | ... | ... | ... | ... | ... | ... | ... |
| hOP-2 | ... | ... | ... | ... | ... | ... | ... | ... | Ser |
| mOP-2 | ... | ... | ... | ... | ... | ... | ... | ... | ... |
| DPP | ... | ... | ... | ... | His | ... | Lys | ... | Pro |
| Vgl | ... | Asn | ... | ... | Tyr | ... | ... | ... | Pro |
| Vgr-1 | ... | Asn | ... | ... | Asp | ... | ... | ... | Ser |
| CBMP-2A | ... | Phe | ... | ... | His | ... | Glu | ... | Pro |
| CBMP-2B | ... | Phe | ... | ... | His | ... | Asp | ... | Pro |
| GDF-1 | ... | Asn | ... | ... | Gln | ... | Gln | ... | ... |
| | | | | 30 | | | | | 35 |
| hOP-1 | Phe | Pro | Leu | Asn | Ser | Tyr | Met | Asn | Ala |
| mOP-1 | ... | ... | ... | ... | ... | ... | ... | ... | ... |

TABLE II-continued

| | | | | | | | | |
|---|---|---|---|---|---|---|---|---|
| hOP-2 | ... | ... | ... | Asp | ... | Cys | ... | ... | ... |
| mOP-2 | ... | ... | ... | Asp | ... | Cys | ... | ... | ... |
| DPP | ... | ... | ... | Ala | Asp | His | Phe | ... | Ser |
| Vgl | Tyr | ... | ... | Thr | Glu | Ile | Leu | ... | Gly |
| Vgr-1 | ... | ... | ... | ... | Ala | His | ... | ... | ... |
| CBMP-2A | ... | ... | ... | Ala | Asp | His | Leu | ... | Ser |
| CBMP-2B | ... | ... | ... | Ala | Asp | His | Leu | ... | Ser |
| GDF-1 | Leu | ... | Val | Ala | Leu | Ser | Gly | Ser** | ... |
| | | | | | 40 | | | | |
| hOP-1 | Thr | Asn | His | Ala | Ile | Val | Gln | Thr | Leu |
| mOP-1 | ... | ... | ... | ... | ... | ... | ... | ... | ... |
| hOP-2 | ... | ... | ... | ... | ... | Leu | ... | Ser | ... |
| mOP-2 | ... | ... | ... | ... | ... | Leu | ... | Ser | ... |
| DPP | ... | ... | ... | ... | Val | ... | ... | ... | ... |
| Vgl | Ser | ... | ... | ... | ... | Leu | ... | ... | ... |
| Vgr-1 | ... | ... | ... | ... | ... | ... | ... | ... | ... |
| CBMP-2A | ... | ... | ... | ... | ... | ... | ... | ... | ... |
| CBMP-2B | ... | ... | ... | ... | ... | ... | ... | ... | ... |
| GDF-1 | Leu | ... | ... | ... | Val | Leu | Arg | Ala | ... |
| | 45 | | | | | 50 | | | |
| hOP-1 | Val | His | Phe | Ile | Asn | Pro | Glu | Thr | Val |
| mOP-1 | ... | ... | ... | ... | ... | ... | Asp | ... | ... |
| hOP-2 | ... | His | Leu | Met | Lys | ... | Asn | Ala | ... |
| mOP-2 | ... | His | Leu | Met | Lys | ... | Asp | Val | ... |
| DPP | ... | Asn | Asn | Asn | ... | ... | Gly | Lys | ... |
| Vgl | ... | ... | Ser | ... | Glu | ... | ... | Asp | Ile |
| Vgr-1 | ... | ... | Val | Met | ... | ... | ... | Tyr | ... |
| CBMP-2A | ... | Asn | Ser | Val | ... | Ser | ... | Lys | Ile |
| CBMP-2B | ... | Asn | Ser | Val | ... | Ser | ... | Lys | Ile |
| GDF-1 | Met | ... | Ala | Ala | Ala | ... | Gly | Ala | Ala |
| | | 55 | | | | | 60 | | |
| hOP-1 | Pro | Lys | Pro | Cys | Cys | Ala | Pro | Thr | Gln |
| mOP-1 | ... | ... | ... | ... | ... | ... | ... | ... | ... |
| hOP-2 | ... | ... | Ala | ... | ... | ... | ... | ... | Lys |
| mOP-2 | ... | ... | Ala | ... | ... | ... | ... | ... | Lys |
| DPP | ... | ... | Ala | ... | ... | ... | Val | ... | ... |
| Vgl | ... | Leu | ... | ... | ... | ... | Val | ... | Lys |
| Vgr-1 | ... | ... | ... | ... | ... | ... | ... | ... | Lys |
| CBMP-2A | ... | ... | Ala | ... | Val | ... | ... | ... | Glu |
| CBMP-2B | ... | ... | Ala | ... | Val | ... | ... | ... | Glu |
| GDF-1 | Asp | Leu | ... | ... | ... | Val | ... | Ala | Arg |
| | | | 65 | | | | | 70 | |
| hOP-1 | Leu | Asn | Ala | Ile | Ser | Val | Leu | Tyr | Phe |
| mOP-1 | ... | ... | ... | ... | ... | ... | ... | ... | ... |
| hOP-2 | ... | Ser | ... | Thr | ... | ... | ... | ... | Tyr |
| mOP-2 | ... | Ser | ... | Thr | ... | ... | ... | ... | Tyr |
| Vgl | Met | Ser | Pro | ... | ... | Met | ... | Phe | Tyr |
| Vgr-1 | Val | ... | ... | ... | ... | ... | ... | ... | ... |
| DPP | ... | Asp | Ser | Val | Ala | Met | ... | ... | Leu |
| CBMP-2A | ... | Ser | ... | ... | ... | Met | ... | ... | Leu |
| CBMP-2B | ... | Ser | ... | ... | ... | Met | ... | ... | Leu |
| GDF-1 | ... | Ser | Pro | ... | ... | ... | ... | Phe | ... |
| | | | | 75 | | | | | 80 |
| hOP-1 | Asp | Asp | Ser | Ser | Asn | Val | Ile | Leu | Lys |
| mOP-1 | ... | ... | ... | ... | ... | ... | ... | ... | ... |
| hOP-2 | ... | Ser | ... | Asn | ... | ... | ... | ... | Arg |
| mOP-2 | ... | Ser | ... | Asn | ... | ... | ... | ... | Arg |
| DPP | Asn | ... | Gln | ... | Thr | ... | Val | ... | ... |
| Vgl | ... | Asn | Asn | Asp | ... | ... | Val | ... | Arg |
| Vgr-1 | ... | ... | Asn | ... | ... | ... | ... | ... | ... |
| CBMP-2A | ... | Glu | Asn | Glu | Lys | ... | Val | ... | ... |
| CBMP-2B | ... | Glu | Tyr | Asp | Lys | ... | Val | ... | ... |
| GDF-1 | ... | Asn | ... | Asp | ... | ... | Val | ... | Arg |
| | | | | | 85 | | | | |
| hOP-1 | Lys | Tyr | Arg | Asn | Met | Val | Val | Arg | |
| mOP-1 | ... | ... | ... | ... | ... | ... | ... | ... | |
| hOP-2 | ... | His | ... | ... | ... | ... | ... | Lys | |
| mOP-2 | ... | His | ... | ... | ... | ... | ... | Lys | |
| DPP | Asn | ... | Gln | Glu | ... | Thr | ... | Val | |
| Vgl | His | ... | Glu | ... | ... | Ala | ... | Asp | |
| Vgr-1 | ... | ... | ... | ... | ... | ... | ... | ... | |
| CBMP-2A | Asn | ... | Gln | Asp | ... | ... | ... | Glu | |
| CBMP-2B | Asn | ... | Gln | Glu | ... | ... | ... | Glu | |
| GDF-1 | Gln | ... | Glu | Asp | ... | ... | ... | Asp | |
| | 90 | | | | | 95 | | | |
| hOP-1 | Ala | Cys | Gly | Cys | His | | | | |
| mOP-1 | ... | ... | ... | ... | ... | | | | |
| hOP-2 | ... | ... | ... | ... | ... | | | | |
| mOP-2 | ... | ... | ... | ... | ... | | | | |

TABLE II-continued

| | | | | | |
|---|---|---|---|---|---|
| DPP | Gly | ... | ... | ... | Arg |
| Vgl | Glu | ... | ... | ... | Arg |
| Vgr-1 | ... | ... | ... | ... | ... |
| CBMP-2A | Gly | ... | ... | ... | Arg |
| CBMP-2B | Gly | ... | ... | ... | Arg |
| GDF-1 | Glu | ... | ... | ... | Arg |
| | | | 100 | | |

\*\*Between residues 43 and 44 of GDF-1 lies the amino acid sequence Gly-Gly-Pro-Pro.

As is apparent from the foregoing amino acid sequence comparisons, significant amino acid changes can be made within the generic sequences while retaining the morphogenic activity. For example, while the GDF-1 protein sequence depicted in Table II shares only about 50% amino acid identity with the hOP1 sequence described therein, the GDF-1 sequence shares greater than 70% amino acid sequence homology (or "similarity") with the hOP1 sequence, where "homology" or "similarity" includes allowed conservative amino acid changes within the sequence as defined by Dayoff, et al., *Atlas of Protein Sequence and Structure* vol.5, supp.3, pp.345–362, (M. O. Dayoff, ed., Nat'l BioMed. Res. Fd'n, Washington D.C. 1979.)

The currently most preferred protein sequences useful as morphogens in this invention include those having greater than 60% identity, preferably greater than 65% identity, with the amino acid sequence defining the conserved six cysteine skeleton of hOP1 (e.g., residues 43–139 of Seq. ID No. 5). These most preferred sequences include both allelic and species variants of the OP-1 and OP-2 proteins, including the Drosophila 60A protein. Accordingly, in still another preferred aspect, the invention includes morphogens comprising species of polypeptide chains having the generic amino acid sequence referred to herein as "OPX", which defines the seven cysteine skeleton and accommodates the identities between the various identified mouse and human OP1 and OP2 proteins. OPX is presented in Seq. ID No. 29. As described therein, each Xaa at a given position independently is selected from the residues occurring at the corresponding position in the C-terminal sequence of mouse or human OP1 or OP2 (see Seq. ID Nos. 5–8 and/or Seq. ID Nos. 16–23).

II. Formulations and Methods for Administering Therapeutic Agents

The morphogens or morphogen-stimulating agents may be provided to an individual by any suitable means, preferably by oral, rectal or other direct administration or, alternatively, by systemic administration.

The suitability of systemic administration is demonstrated by the detection of endogenous morphogen in milk and human serum described, for example, in U.S. Ser. No. 07/923,780, filed Jul. 31, 1992, abandoned and continued as U.S. Ser. No. 08/432,883, incorporated herein by reference, and in Example 2, below. Where the morphogen is to be provided parenterally, such as by intravenous, subcutaneous, intramuscular, intraorbital, intraventricular, intracapsular, intraspinal, intracisternal, intraperitoneal or vaginal administration, the morphogen preferably comprises part of an aqueous solution. The solution is physiologically acceptable so that in addition to delivery of the desired morphogen to the patient, the solution does not otherwise adversely affect the patient's electrolyte and volume balance. The aqueous medium for the morphogen thus may comprise normal physiologic saline (0.85% NaCl, 0.15M), pH 7–7.4. The aqueous solution containing the morphogen can be made, for example, by dissolving the protein in 50% ethanol containing acetonitrile in 0.1% trifluoroacetic acid (TFA) or 0.1% HCl, or equivalent solvents. One volume of the resultant solution then is added, for example, to ten volumes of phosphate buffered saline (PBS), which further may include 0.1–0.2% human serum albumin (HSA). The resultant solution preferably is vortexed extensively. If desired, a given morphogen may be made more soluble by association with a suitable molecule. For example, the pro form of the morphogenic protein comprises a species that is soluble in physiological solutions. In fact, the endogenous protein is thought to be transported (e.g., secreted and circulated) in this form. This soluble form of the protein may be obtained from the culture medium of morphogen-secreting cells. Alternatively, a soluble species may be formulated by complexing the mature dimer, (or an active fragment thereof) with part or all of a pro domain. Other components, including various serum proteins, also may be useful.

Useful solutions for parenteral administration may be prepared by any of the methods well known in the pharmaceutical art, described, for example, in *Remington's Pharmaceutical Sciences* (Gennaro, A., ed.), Mack Pub., 1990. Formulations may include, for example, polyalkylene glycols such as polyethylene glycol, oils of vegetable origin, hydrogened naphthalenes, and the like. Other potentially useful parenteral delivery systems for these morphogens include ethylene-vinyl acetate copolymer particles, osmotic pumps, implantable infusion systems, and liposomes. Formulations for parenteral administration may also include cutric acid for vaginal administration.

Preferably, the morphogens described herein are administered directly e.g., topically, for example, by oral or rectal administration, or by directly applying the therapeutic formulation onto the desired tissue. Oral administration of proteins as therapeutics generally is not practiced as most proteins are readily degraded by digestive enzymes and acids in the mammalian digestive system before they can be absorbed into the bloodstream. However, the morphogens described herein typically are acid stable and protease-resistant (see, for example, U.S. Pat. No. 4,968,590). In addition, at least one morphogen, OP-1, has been identified in mammary gland extract, colostrum and 57-day milk. Moreover, the OP-1 purified from mammary gland extract is morphogenically active. Specifically, this protein induces endochondral bone formation in mammals when implanted subcutaneously in association with a suitable matrix material, using a standard in vivo bone assay, such as is disclosed in U.S. Pat. No. 4,968,590. Moreover, as described above, the morphogen also is detected in the bloodstream. These findings indicate that oral administration is a viable means for administering morphogens to an individual. In addition, while the mature forms of certain morphogens described herein typically are sparingly soluble, the morphogen form found in milk (and mammary gland extract and colostrum) is readily soluble, probably by association of the mature, morphogenically active form with part or all of the pro domain of the intact sequence and/or by association with one or more milk components. Accordingly, the compounds provided herein also may be associated with molecules capable of enhancing their solubility in vitro or in vivo.

For oral mucositis treatments the morphogens or morphogen-stimulating agents (herein below referred to collectively as "therapeutic agent") may be formulated into an oral rinse similar to a mouthwash, where the liquid is swished around in the mouth so that the therapeutic agent is brought in contact with the oral mucosa to maximize treatment of lesions. Alternatively, the therapeutic agent may be formulated as part of a slow dissolving troche or lozenge, or dispersed in a gum base suitable for a chewing gum, such that the agent is released with mastication.

Longer contact with the mucosal surface of the mouth cavity or elsewhere in the G.I. tract can be attained by direct topical administration, using a suitable vehicle which is capable of coating mucosa. Typical examples are pectin-containing formulations or sucralfate suspensions, such as are found in "KAOPECTATE" and "MILK OF MAGNESIA." Formulations for direct administration also may include glycerol and other compositions of high viscosity. Tissue adhesives capable of adhering to the mucosal tissue surface and maintaining the therapeutic agent at the tissue locus also may be used. Useful adhesive compositions include hydroxypropyl-cellulose-containing solutions, such as is found in ORABASE® (Colgate-Hoyt Laboratories, Norwood, Mass.), or fibrinogen/thrombin-containing solutions. Another useful adhesive is the bio-adhesive described in U.S. Pat. No. 5,197,973, incorporated herein above by reference. Preferably these formulations are painted onto the tissue surface or formulated as an aerosol and sprayed onto the tissue surface. As for parenteral administration, the therapeutic agent may be associated with a molecule that enhances solubility. For example, addition of 0.2% casein increases solubility of the mature active form of OP-1 by 80%. Another useful molecule is a morphogen pro domain.

For all treatments of the gastrointestinal tract, the therapeutic agent also may be formulated into a solid or liquid to be consumed or as an inhalant. For treatments of the lower bowel, formulations for rectal administration may be preferable, and may include suppositories, creams, gels, lotions and the like. In all applications, biocompatible, preferably bioresorbable, polymers, including, for example, hyaluronic acid, collagen, polybutyrate, tricalcium phosphate, glycolide, lactide and lactide/glycolide copolymers, also may be useful excipients to control the release of the morphogen in vivo. Tablets or capsules may be prepared by employing additives such as pharmaceutically acceptable carriers (e.g., lactose, corn starch, light silicic anhydride, microcrystalline cellulose, sucrose), binders (e.g., alpha-form starch, methylcellulose, carboxymethyicellulose, hydroxypropylcellulose, hydroxypropylmethylcellulose, polyvinylpyrrolidone), disintegrating agents (e.g., carboxymethylcellulose calcium, starch, low substituted hydroxypropylcellulose), surfactants [e.g., Tween 80 Kao-Atlas), Pluronic F68 (Asahi Denka, Japan); polyoxyethylene-polyoxypropylene copolymer)], antioxidants (e.g., L-cysteine, sodium sulfite, sodium ascorbate), lubricants (e-g., magnesium stearate, talc), and the like.

Formulations for inhalation administration may acontain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for rectal administration also may include methoxy salicylate. The formulations for rectal administration also can be a spreadable cream, gel, suppository, foam, lotion or ointment having a pharmaceutically acceptable nontoxic vehicle or carrier. Biocompatible, preferably bioresorbable, polymers, including, for example, hyaluronic acid, collagen, polybutyrate, tricalcium phosphate, lactide and lactide/glycolide copolymers, also may be useful excipients to control the release of the morphogen in vivo.

The compounds provided herein also may be associated with molecules capable of targeting the morphogen or morphogen-stimulating agent to the gastrointestinal barrier tissue. For example, an antibody, antibody fragment, or other binding protein that interacts specifically with a surface molecule on basal epithelial cells, may be used. Useful targeting molecules may be designed, for example, using the single chain binding site technology disclosed, for example, in U.S. Pat. No. 5,091,513.

As described above, the morphogens provided herein share significant sequence homology in the C-terminal active domains. By contrast, the sequences typically diverge significantly in the sequences which define the pro domain. Accordingly, the pro domain is thought to be morphogen-specific. As described above, it is also known that the various morphogens identified to date are differentially expressed in different tissues. Accordingly, without being limited to any given theory, it is likely that, under natural conditions in the body, selected morphogens typically act on a given tissue. Accordingly, part or all of the pro domains which have been identified associated with the active form of the morphogen in solution, may serve as targeting molecules for the morphogens described herein. For example, the pro domains may interact specifically with one or more molecules at the target tissue to direct the morphogen associated with the pro domain to that tissue. Accordingly, another useful targeting molecule for targeting a morphogen to gastrointestinal barrier tissues may include part or all of a morphogen pro domain, particularly part or all of a pro domain normally associated with an endogenous morphogen known to act on GI tract tissue. As described above, morphogen species comprising the pro domain may be obtained from the culture medium of morphogen-secreting mammalian cells. Alternatively, a tissue-targeting species may be formulated by complexing the mature dimer (or an active fragment thereof) with part or all of a pro domain. Example 1 describes a protocol for identifying morphogen-expressing tissue and/or morphogen target tissue.

Finally, the morphogens or morphogen-stimulating agents provided herein may be administered alone or in combination with other molecules known to be beneficial in treating gastrointestinal tract ulcers, particularly symptom-alleviating cofactors. Useful pharmaceutical cofactors include analgesics and anesthetics such as xylocaine, benzocaine and the like; antiseptics such as chlorohexidine; anti-viral and anti-fungal agents; and antibiotics, including aminoglycosides, macrolides, penicillins, and cephalosporins. Other potentially useful cofactors include antisecretory agents such as H2-receptor antagonists (e.g., cimetidine, ranitidine, famotidine, roxatidine acetate), muscarine receptor antagonists (e.g., Pirenzepine), and antacids such as aluminum hydroxide gel, magnesium hydroxide and sodium bicarbonate. Such agents may be administered either separately or as components of the therapeutic composition containing morphogens or morphogen-stimulating agents.

The compositions can be formulated for parenteral or direct administration to humans or other mammals in therapeutically effective amounts, e.g., amounts which provide appropriate concentrations for a time sufficient to protect the patient's gastrointestinal luminal lining from lesion formation, including amounts which limit the proliferation of epithelial cells, particularly the basal epithelial cells of the G.I. tract, amounts which limit the inflammation associated with the ulcerative diseases and disorders described above, and amounts sufficient to stimulate lesion repair and tissue regeneration.

As will be appreciated by those skilled in the art, the concentration of the compounds described in a therapeutic composition will vary depending upon a number of factors, including the dosage of the drug to be administered, the chemical characteristics (e.g., hydrophobicity) of the compounds employed, and the route of administration. The preferred dosage of drug to be administered also is likely to depend on such variables as the type and extent of progression of the ulcerative disease, the overall health status of the particular patient, the relative biological efficacy of the compound selected, the formulation of the compound excipients, and its route of administration. In general terms, the compounds of this invention may be provided in an aqueous physiological buffer solution containing about 0.001 to 10% w/v compound for parenteral administration. Typical dose ranges are from about 10 ng/kg to about 1 g/kg of body weight per day; a preferred dose range is from about 0.1 µg/kg to 100 mg/kg of body weight per day. Optimally, the morphogen dosage given is between 0.1–100 µg of protein per kilogram weight of the patient. Administration may be a single dose per day, or may include multiple doses, such as multiple rinsings with a mouthwash, e.g., a 1 minute rinse three or four times daily. No obvious induced pathological lesions are induced when mature morphogen (e.g., OP-1, 20 µg) is administered daily to normal growing rats for 21 consecutive days. Moreover, 10 µg systemic injections of morphogen (e.g., OP-1) injected daily for 10 days into normal newborn mice does not produce any gross abnormalities.

In administering morphogens systemically in the methods of the present invention, preferably a large volume loading dose is used at the start of the treatment. The treatment then is continued with a maintenance dose. Further administration then can be determined by monitoring at intervals the levels of the morphogen in the blood using, for example, a morphogen-specific antibody and standard immunoassay procedures.

Where injury to the mucosa is induced deliberately or incidentally, as part of, for example, a chemical or radiation therapy, the morphogen preferably is provided just prior to, or concomitant with induction of the treatment. Preferably, the morphogen is administered prophylactically in a clinical setting. Optimally, the morphogen dosage given is between 0.1–100 µg of protein per kilogram weight of the patient. Similarly, the morphogen may be administered prophylactically to individuals at risk for ulcer formation, including xerostomatic or immune-compromised individuals, regardless of etiology.

An effective amount of an agent capable of stimulating endogenous morphogen levels also may be administered by any of the routes described above. For example, an agent capable of stimulating morphogen production in and/or secretion to G.I. tract tissue cells may be provided to a mammal. A method for identifying and testing agents capable of modulating the levels of endogenous morphogens in a given tissue is described generally herein in Example 10, and in detail in U.S. patent application Ser. No. 07/938,336, filed Aug. 28, 1992, abandoned and continued as U.S. patent application Ser. Nos. 08/445,467 and 08/600,352 the disclosures of which are incorporated herein by reference. In addition, Example 1 describes a protocol for determining morphogen-expressing tissue. Briefly, candidate compounds can be identified and tested by incubating the compound in vitro with a test tissue or cells thereof, for a time sufficient to allow the compound to affect the production, i.e., the expression and/or secretion, of a morphogen produced by the cells of that tissue. Here, suitable tissue or cultured cells of a tissue preferably would include cells of the G.I. tract barrier. For example, suitable tissue for testing may include cultured cells isolated from the basal epithelium and mucosa, and the like.

A currently preferred detection means for evaluating the level of the morphogen in culture upon exposure to the candidate compound comprises an immunoassay utilizing an antibody or other suitable binding protein capable of reacting specifically with a morphogen and being detected as part of a complex with the morphogen. Immunoassays may be performed using standard techniques known in the art and antibodies raised against a morphogen and specific for that morphogen. As described herein, morphogens may be isolated from natural-sourced material or they may be recombinantly produced. Agents capable of stimulating endogenous morphogens then may formulated into pharmaceutical preparations and administered as described herein.

III. EXAMPLES

Example 1

Identification of Morphogen-Expressing Tissue

Determining the tissue distribution of morphogens may be used to identify different morphogens expressed in a given tissue, as well as to identify new, related morphogens. Tissue distribution also may be used to identify useful morphogen-producing tissue for use in screening and identifying candidate morphogen-stimulating agents. The morphogens (or their mRNA transcripts) readily are identified in different tissues using standard methodologies and minor modifications thereof in tissues where expression may be low. For example, protein distribution may be determined using standard Western blot analysis or immunofluorescent techniques, and antibodies specific to the morphogen or morphogens of interest. Similarly, the distribution of morphogen transcripts may be determined using standard Northern hybridization protocols and transcript-specific oligonucleotide probes.

Any probe capable of hybridizing specifically to a transcript, and distinguishing the transcript of interest from other, related transcripts may be used. Because the morphogens described herein share such high sequence homology in their active, C-terminal domains, the tissue distribution of a specific morphogen transcript may best be determined using a probe specific for the pro region of the immature protein and/or the N-terminal region of the mature protein. Another useful sequence is the 3' non-coding region flanking and immediately following the stop codon. These portions of the sequence vary substantially among the morphogens of this invention, and accordingly, are specific for each protein. For example, a particularly useful Vgr-1-specific probe sequence is the PvuII-SacI fragment, a 265 bp fragment encoding both a portion of the untranslated pro region and the N-terminus of the mature sequence (see Lyons et al. (1989) PNAS 86:4554–4558 for a description of the cDNA sequence). Similarly, particularly useful mOP-1-specific probe sequences are the BstXI-BglI fragment, a 0.68 Kb sequence that covers approximately two-thirds of the mOP-1 pro region; a StuI-StuI fragment, a 0.2 Kb sequence immediately upstream of the 7-cysteine domain; and the EarI-PstI fragment, an 0.3 Kb fragment containing a portion of the 3' untranslated sequence (See Seq. ID No. 18, where the pro region is defined essentially by residues 30–291.) Similar approaches may be used, for example, with hOP-1 (Seq. ID No. 16) or human or mouse OP-2 (Seq. ID Nos. 20 and 22.)

Using these morphogen-specific probes, which may be synthetically engineered or obtained from cloned sequences, morphogen transcripts can be identified in mammalian tissue, using standard methodologies well known to those having ordinary skill in the art. Briefly, total RNA is prepared from various adult murine tissues (e.g., liver, kidney, testis, heart, brain, thymus and stomach) by a standard methodology such as by the method of Chomczyaski et al. ((1987) *Anal. Biochem* 162:156–159) and described below. Poly (A)+ RNA is prepared by using oligo (dT)-cellulose chromatography (e.g., Type 7, from Pharmacia LKB Biotechnology, Inc.). Poly (A)+ RNA (generally 15 µg) from each tissue is fractionated on a 1% agarose/formaldehyde gel and transferred onto a Nytran membrane (Schleicher & Schuell). Following the transfer, the membrane is baked at 80° C. and the RNA is cross-linked under UV light (generally 30 seconds at 1 mW/cm$^2$). Prior to hybridization, the appropriate probe is denatured by heating. The hybridization is carried out in a lucite cylinder rotating in a roller bottle apparatus at approximately 1 rev/min for approximately 15 hours at 37° C. using a hybridization mix of 40% formamide, 5× Denhardts, 5× SSPE, and 0.1% SDS. Following hybridization, the non-specific counts are washed off the filters in 0.1× SSPE, 0.1% SDS at 50° C.

Examples demonstrating the tissue distribution of various morphogens, including Vgr-1, OP-1, BMP2, BMP3, BMP4, BMP5, GDF-1, and OP-2 in developing and adult tissue are disclosed in U.S. patent application Ser. No. 07/752,764, abandoned and continued as U.S. patent application Ser. Nos. 08/404,113 and 08/396,684, and in Ozkaynak, et al., (1991) *Biochem. Biophys. Res. Commn.* 179:116–123, and Ozkaynak, et al. (1992) *J. Biol. Chem.* 267:25220–25227 the disclosures of which are incorporated herein by reference. Using the general probing methodology described herein, Northern blot hybridizations using probes specific for these morphogens to probe brain, spleen, lung, heart, liver and kidney tissue indicate that kidney-related tissue appears to be the primary expression source for OP-1, with brain, heart and lung tissues being secondary sources. OP-1 mRNA also was identified in salivary glands, specifically rat parotid glands, using this probingmethodology. Lung tissue appears to be the primary tissue expression source for Vgr-1, BMP5, BMP4 and BMP3. Lower levels of Vgr-1 also are seen in kidney and heart tissue, while the liver appears to be a secondary expression source for BMP5, and the spleen appears to be a secondary expression source for BMP4. GDF-1 appears to be expressed primarily in brain tissue. To date, OP-2 appears to be expressed primarily in early embryonic tissue. Specifically, Northern blots of murine embryos and 6-day post-natal animals shows abundant OP2 expression in 8-day embryos. Expression is reduced significantly in 17-day embryos and is not detected in post-natal animals.

Immunolocalization studies using OP-1 specific antibodies also localize the morphogen to both the inner circular and outer longitudinal coats of smooth muscles in the tubular organs of the digestive system during early embryo development (gestation: weeks 5–13), suggesting the endogenous morphogen also plays a role in tissue morphogenesis of the digestive tract.

Moreover, Northern blot analysis on rat tissue (probed with an mOP-1-specific labelled nucleotide fragment, as described above) identifies OP-1 mRNA in the gastrointestinal tract tissues of growing rats, including the stomach, duodenal and intestine tissues. These data demonstrate that morphogens are both expressed in, and act on, tissues of the GI tract.

Example 2

Active Morphogens in Body Fluids

OP-1 expression has been identified in saliva (specifically, the rat parotid gland, see Example 1), human blood serum, and various milk forms, including mammary gland extract, colostrum, and 57-day bovine milk. Moreover, and as described in U.S. patent application Ser. No. 07/923,780, filed Jul. 31, 1992, abandoned and continued as Ser. No. 08/432,883 the disclosure of which is incorporated hereinabove by reference, the body fluid-extracted protein is morphogenically active. The discovery that the morphogen naturally is present in milk and saliva, together with the known observation that mature, active OP-1 is acid-stable and protease-resistant, indicate that oral administration is a useful route for therapeutic administration of morphogen to a mammal. Oral administration typically is the preferred mode of delivery for extended or prophylactic therapies. In addition, the identification of morphogen in all milk forms, including colostrum, suggests that the protein may play a significant role in tissue development, including skeletal development, of juveniles.

2.1 Morphogen Detection in Milk

OP-1 was partially purified from rat mammary gland extract and bovine colostrum and 57 day milk by passing these fluids over a series of chromatography columns: (e.g., cation-exchange, affinity and reverse phase). At each step the eluant was collected in fractions and these were tested for the presence of OP-1 by standard immunoblot. Immunoreactive fractions then were combined and purified further. The final, partially purified product then was examined for the presence of OP-1 by Western blot analysis using OP-1-specific antisera, and tested for in vivo and in vitro activity.

OP-1 purified from the different milk sources were characterized by Western blotting using antibodies raised against OP-1 and BMP2. Antibodies were prepared using standard immunology protocols well known in the art, and as described generally in Example 15, below, using full-length *E. coli*-produced OP-1 and BMP2 as the immunogens. In all cases, the purified OP-1 reacted only with the anti-OP-1 antibody, and not with anti-BMP2 antibody.

The morphogenic activity of OP-1 purified from mammary gland extract was evaluated in vivo essentially following the rat model assay described in U.S. Pat. No. 4,968,590, hereby incorporated by reference. Briefly, a sample was prepared from each OP-1 immunoreactive fraction of the mammary gland extract-derived OP-1 final product by lyophilizing a portion (33%) of the fraction and resuspending the protein in 220 µl of 50% acetonitrile/0.1% TFA. After vortexing, 25 mg of collagen matrix was added. The samples were lyophilized overnight, and implanted in Long Evans rats (Charles River Laboratories, Wilmington, Mass., 28–35 days old). Each fraction was implanted in duplicate. For details of the collagen matrix implantation procedure, see, for example, U.S. Pat. No. 4,968,590, hereby incorporated by reference. After 12 days, the implants were removed and evaluated for new bone formation by histological observation as described in U.S. Pat. No. 4,968,590. In all cases, the immunoreactive fractions were osteogenically active.

2.2 Morphogen Detection in Serum

Morphogen may be detected in serum using morphogen-specific antibodies. The assay may be performed using any standard immunoassay, such as Western blot (immunoblot) and the like. Preferably, the assay is performed using an affinity column to which the morphogen-specific antibody is bound and through which the sample serum then is poured, to selectively extract the morphogen of interest. The morphogen then is eluted. A suitable elution buffer may be determined empirically by determining appropriate binding and elution conditions first with a control (e.g., purified, recombinantly-produced morphogen.) Fractions then are tested for the presence of the morphogen by standard immunoblot, and the results confirmed by N-terminal sequencing. Preferably, the affinity column is prepared using monoclonal antibodies. Morphogen concentrations in serum or other fluid samples then may be determined using standard protein quantification techniques, including by spectrophotometric absorbance or by quantitation of conjugated antibody.

Presented below is a sample protocol for identifying OP-1 in serum. Following this general methodology other morphogens may be detected in body fluids, including serum. The identification of morphogen in serum further indicates that systemic administration is a suitable means for providing therapeutic concentrations of a morphogen to an individual, and that morphogens likely behave systemically as endocrine-like factors. Finally, using this protocol, fluctuations in endogenous morphogen levels can be detected, and these altered levels may be used as an indicator of tissue dysfunction. Alternatively, fluctuations in morphogen levels may be assessed by monitoring morphogen transcription levels, either by standard Northern blot analysis as described in Example 1, or by in situ hybridization, using a labelled probe capable of hybridizing specifically to morphogen mRNA, and standard RNA hybridization protocols well described in the art and described generally in Example 1.

OP-1 was detected in human serum using the following assay. A monoclonal antibody raised against mammalian, recombinantly produced OP-1 using standard immunology techniques well described in the art and described generally in Example 15, was immobilized by passing the antibody over an agarose-activated gel (e.g., Affi-Gel™, from Bio-Rad Laboratories, Richmond, Calif., prepared following manufacturer's instructions) and used to purify OP-1 from serum. Human serum then was passed over the column and eluted with 3M K-thiocyanate. K-thiocyanante fractions then were dialyzed in 6M urea, 20 mM $PO_4$, pH 7.0, applied to a C8 HPLC column, and eluted with a 20 minute, 25–50% acetonitrile/0.1% TFA gradient. Since mature, recombinantly produced OP-1 homodimers elute between 20–22 minutes, these fractions then were collected and tested for the presence of OP-1 by standard immunoblot using an OP-1 specific antibody as for Example 2.A.

Administered or endogenous morphogen levels may be monitored in the therapies described herein by comparing the quantity of morphogen present in a body fluid sample with a predetermined reference value, for example, to evaluate the efficiency of a therapeutic protocol, and the like. In addition, fluctuations in the level of endogenous morphogen antibodies may be detected by this method, most likely in serum, using an antibody or other binding protein capable of interacting specifically with the endogenous morphogen antibody. Detected fluctuations in the levels of the morphogen or endogenous antibody may be used, for example, as indicators of a change in tissue status. For example, as damaged tissue is regenerated and the tissue or organ's function returns to "normal" and, in the absence of additional tissue damage, lower doses of morphogen may be required, and a higher level of circulating morphogen antibody may be measured.

Example 3

Morphogen Treatment of Oral Mucositis

Oral mucositis involves ulcerations of the mouth as a consequence of, e.g., radiation therapy or chemotherapy. The course of ulcerative mucositis may be divided into a destructive phase and a healing phase. Since the cells of the basal layer of the oral epithelium divide at a rapid rate, they are susceptible to the antimitogenic and toxic effects of chemotherapy. As a result, atrophic changes occur which then are followed by ulceration. This constitutes the destructive phase. Following ulcer formation, the lesions slowly resolve during the healing phase.

The example below demonstrates morphogen efficacy in protecting the oral mucosa from oral mucositis in a hamster model, including both inhibiting ulceration and enhancing regeneration of ulcerated tissue. Details of the protocol can be found in Sonis, et al., (1990) *Oral Surg. Oral Med. Oral Pathol* 69: 437–443, the disclosure of which is incorporated herein by reference. Briefly, golden syrian hamsters (6–8 wks old, Charles River Laboratories, Wilmington, Mass.) were divided into 3 test groups: Group 1, a placebo (e.g., saline) control, and a morphogen low dose group (100 ng) and a morphogen high dose group (1 µg), Groups 2 and 3, respectively. Morphogen dosages were provided in 30% ethanol. Each group contained 12 animals.

Beginning on day 0 and continuing through day 5, Groups 2 and 3 received twice daily morphogen applications. On day 3, all groups began the mucositis-induction procedure. 5-fluorouracil was injected intraperitoneally on days 3 (60 mg/kg) and 5 (40 mg/kg). On day 7, the right buccal pouch mucosa was superficially irritated with a calibrated 18 gauge needle. In untreated animals, severe ulcerative mucositis was induced in at least 80% of the animals by day 10.

For each administration of the vehicle control (placebo) or morphogen, administration was performed by first gently drying the cheek pouch mucosa, then providing an even application over the mucosal surface of the vehicle or morphogen material. A hydroxypropylcellulose-based coating was used to maintain contact of the morphogen with the mucosa. This coating provided at least 4 hours of contact time.

On day 12, two animals in each group were sacrificed for histological studies. The right buccal pouch mucosa and underlying connective tissue were dissected and fixed in 10% formalin using standard dissection and histology procedures. The specimens were mounted in paraffin and prepared for histologic examination. Sections then were stained with hematoxylin and eosin and were examined blindly by three oral pathologists with expertise in hamster histology and scored blind against a standard mucositis panel. The extent of atrophy, cellular infiltration, connective tissue breakdown, degree of ulceration and epithelialization were assessed.

The mean mucositis score for each group was determined daily for each experimental group for a period of 21 days by photography and visual examination of the right buccal cheek pouch. Differences between groups were determined using the Students' 't' test. In addition, data was evaluated between groups by comparing the numbers of animals with severe mucositis using Chi Square statistical analysis. The significance of differences in mean daily weights also was determined.

Figure 2A:
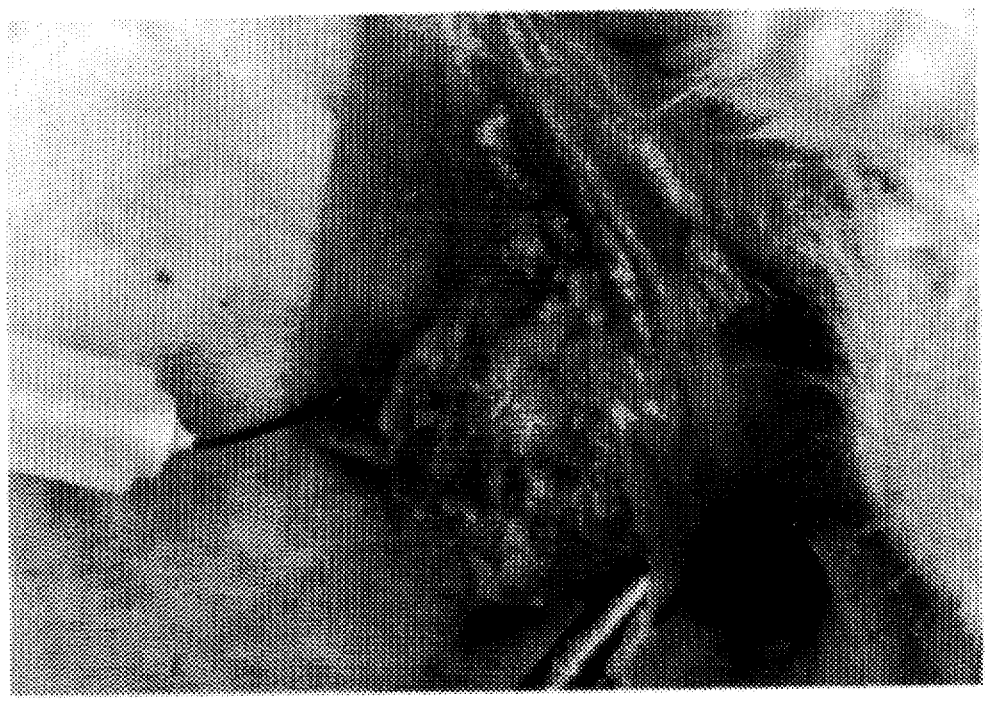
FIG. 2A and 2B are photomicrographs illustrating the ability of morphogens to inhibit lesion formation in an oral mucositis animal model, where 2A shows lesion formation in untreated hamster cheek pouches; and 2B shows the significantly reduced effect on morphogen treated cheek pouches.
Figure 2B:
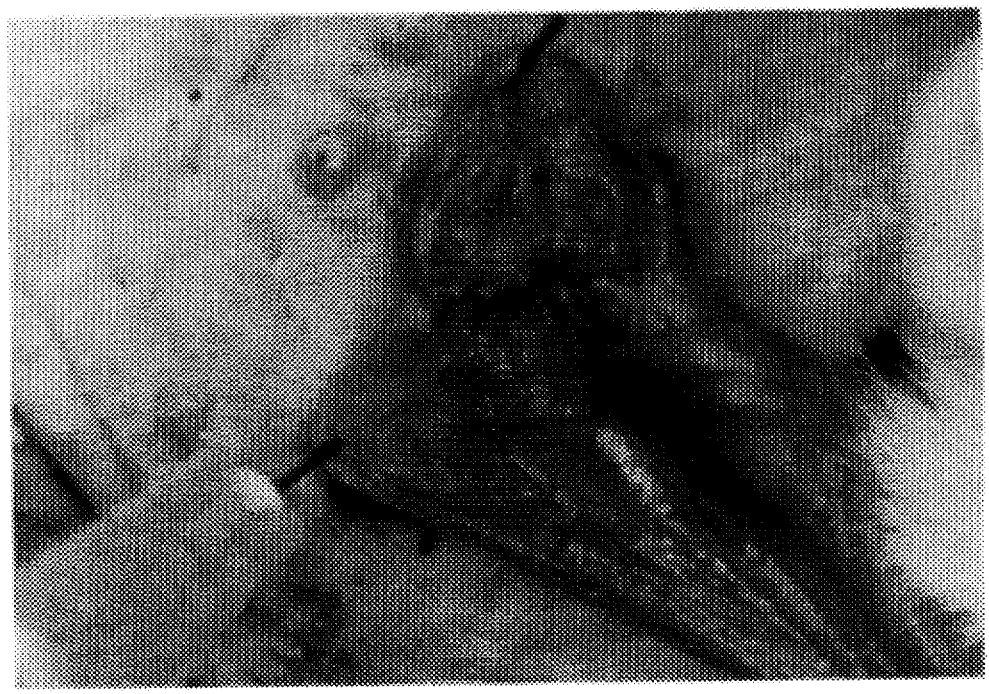

The experimental results are presented in FIGS. 1 and 2. FIG. 1 graphs the effect of morphogen (high dose, squares; low dose, diamonds) and placebo (circles) on mean mucositis scores. Both low and high morphogen doses inhibit lesion formation significantly in a dose-dependent manner. FIG. 2 (A and B) are photomicrographs of a buccal cheek pouch on day 14, pretreated with morphogen, high dose (B) or saline alone (A). Significant tissue necrosis, indicated by the dark regions in the tissue, and ulceration, indicated by the light globular areas in the tissue, is evident in the untreated pouch in FIG. 2A. By contrast, the morphogen-treated tissue in FIG. 2B shows healthy tissue with no necrosis and little or no ulceration. In addition, histology results consistently showed significantly reduced amounts of tissue atrophy, cellular debris, and immune effector cells, including activated macrophages and neutrophils, in the morphogen-treated animals, as compared with the untreated, control animals.

In a variation on this protocol, morphogen also may be administered daily for several days before mucositis-induction and/or for longer periods following 5-fluorouracil treatments.

Example 4

Morphogen Treatment of Duodenal Ulcer Formation

The following example provides a rat model for demonstrating morphogen efficacy in treating duodenal ulcers. A detailed description of the protocol is provided in Pilan et al., (1985) *Digestive Diseases and Sciences* 30: 240–246, the disclosure of which is incorporated herein by reference.

Briefly, Sprague-Dawley female rats (e.g., Charles River Laboratories, 150–200 grams) receive the duodenal ulcerogen cysteamine-HCl at a dose of 25–28 milligrams (mg) per 100 grams (gm) of body weight orally by intragastric gavage 3 times on the same day. Additionally, cortisol is administered subcutaneously to each rat at a single dose of 5mg of cortisol to 100 gm of body weight to decrease the mortality resulting from the administration of the cysteamine-HCl.

Three days after administration of the cysteamine-HCl, rats having penetrating and perforating duodenal ulcers are identified by standard laparotomy and randomized into control and morphogen-treated groups.

The rats of Group 1, all of which have ulcers, receive no morphogen and are treated only with saline. The rats of Group 2 each of which also have ulcers, receive 50–100 ng of morphogen per 100 gm of body weight. Group 3 rats, all of which have ulcers, receive 200–500 ng of morphogen per 100 gm of body weight. All treatments are by gavage twice daily until autopsy on day 21, when the ulcers are measured and histologic sections taken.

Histology of duodenal sections from morphogen-treated animals shows healed ulcers with prominent and dense granulation tissue and partial or complete re-epitheliazation, demonstrating that oral administration of morphogen can significantly accelerate the healing of ulcers of the GI tract. Moreover, treatement with morphogen before or concomitantly with ulceration also inhibits ulcer formation.

Example 5

Gastric acid and Pepsin Secretion of Morphogen-Treated Rats

The following example demonstrates morphogen efficacy as determined by gastric acid and pepsin secretion. A detailed description of the protocol is provided in Pilan et al., disclosed above. Briefly, 18–20 rats are divided into 2 groups, a control group (Group 1) and a morphogen treated group (Group 2).

All rats are fasted for 24 hours and given either saline vehicle alone (Group 1) or morphogen (e.g., 500 ng/ml, Group 2). The stomachs of the rats then are constricted with a pyloric ligature for one hour.

Gastric juice is collected from each rat in groups 1 and 2, centrifuged and aliquots processed for acid titration to calculate gastric acid output and pepsin determination. Gastric acid is measured by the acidity of the gastric juices, and pepsin levels are determined according to standard protease assays well-known in the art. Since pepsin is the most abundant protease in the stomach, the total protease level is a good measurement of the pepsin level. The gastric juice aliquots are spectrophotometrically analyzed using albumin as a a substrate. (Szabo, S. et al. (1977) *Res. Comm. Chem. Pathol. Pharmacol.* 16: 311–323, hereby incorporated by reference).

In both control and morphogen-treated rats normal levels of gastric pepsin output and gastric juice volume can be measured. Thus, morphogen treatment of ulcers of the GI tract does not affect the normal levels of gastric acid or pepsin in the GI tract.

Example 6

Morphogen Treatment of Ulcerative colitis

Ulcerative colitis involves ulcers of the colon. The example provided below demonstrates morphogen efficacy in treating ulcerative colitis using a guinea pig model. A detailed description of the protocol is provided in Onderdonk et al- (1979) *Amer. J. Clin. Nutr.* 32: 258–265, the disclosure of which is incorporated herein by reference.

Briefly, guinea pigs, (e.g., 500–550 gms, Charles River Laboratories) are divided into 3 experimental groups, each group containing multiple animals: a control, Group 1, which receives distilled water to drink; Group 2, which receives distilled water containing 1% degraded carrageenin; and Group 3, which receives distilled water containing 5% degraded carrageenin to drink. Degraded carrageenin is a polysaccharide derived from red seaweeds, (Glaxo Laboratories, Paris, France), and is a known inducer of ulcerative colitis in guinea pigs.

The development of colitis is determined using several criteria: 1) presence of loose and/or bloody feces by visual inspection, 2) detection of occult blood in the feces using Coloscreen III with hemocult developer (Helena Labs, Bumont, Tex.), and 3) weight loss.

At day 25, each animal is anesthetized with Ketamine (3–5 mg/kg) administered intramuscularly and a 3 mm colorectal mucosa biopsy taken using a small nasal scope. All of the specimens are fixed in 15% formaldehyde and examined histologically using hematoxylin and eosin. The pathologic diagnosis of ulcerative colitis is established by the presence of crypt abscesses, lymphocytic infiltration, capillary congestion of the lamina propria and ulceration of the colon mucosa (Onderdonk, (1985) *Digestive Disease Science* 30:40(s), hereby incorporated by reference). The severity of ulcerative colitis is graded on a scale of 0 to 3 and expressed as the pathological index according to the standard scoring system (Onderdonk et al. (1979), *Amer. J. Clin. Nutrition* 32:258.)

At day 30, 25% of the guinea pigs in which ulcerative colitis was demonstrated histologically are treated with morphogen and the remaining 25% receive distilled water as a control. Morphogen is administered both at a low dose (e.g., 100 ng/100 gm) in one half of the guinea pigs; and at a high dose (e.g., 500–1000 ng/100 gm), administered orally through a 3 mmbulbed needle, twice per day for a period of 10 days (days 28–37).

During treatment, the animals are evaluated clinically and improvements in body weight, stool consistency and reduction or absence of blood in stools recorded. At day 37, all animals are sacrificed with an overdose of pentobarbital (>200 mg/kg) and the entire colon removed for histological evaluation. Colon ulcers in morphogen treated animals are signficantly repaired and healed as compared with untreated ulcers, untreated ulcers.

Example 7
Morphogen Inhibition of Epithelial Cell Proliferation

This example demonstrates the ability of morphogens to inhibit epithelial cell proliferation in vitro, as determined by $^3$H-thymidine uptake using culture cells from a mink lung epithelial cell line (ATCC No. CCL 64, Rockville, Md.), and standard mammalian cell culturing procedures. Briefly, cells were grown to confluency in Eagle's minimum essential medium (EMEM) supplemented with 10% fetal bovine serum (FBS), 200 units/ml penicillin, and 200 μg/ml streptomycin, and used to seed a 48-well cell culture plate at a cell density of 200,000 cells per well. When this culture became confluent, the media was replaced with 0.5 ml of EMEM containing 1% FBS and penicillin/streptomycin and the culture incubated for 24 hours at 37 C. Morphogen test samples in EMEM containing 5% FBS then were added to the wells, and the cells incubated for another 18 hours. After incubation, 1.0 μCi of $^3$H-thymidine in 10 μl was added to each well, and the cells incubated for four hours at 37 C. The media then was removed and the cells washed once with ice-cold phosphate-buffer saline and DNA precipitated by adding 0.5 ml of 10% TCA to each well and incubating at room temperature of 15 minutes. The cells then were washed three times with ice-cold distilled water, lysed with 0.5 ml 0.4 M NaOH, and the lysate from each well then transferred to a scintillation vial and the radioactivity recorded using a scintillation counter (Smith-Kline Beckman).

Figure 3A:
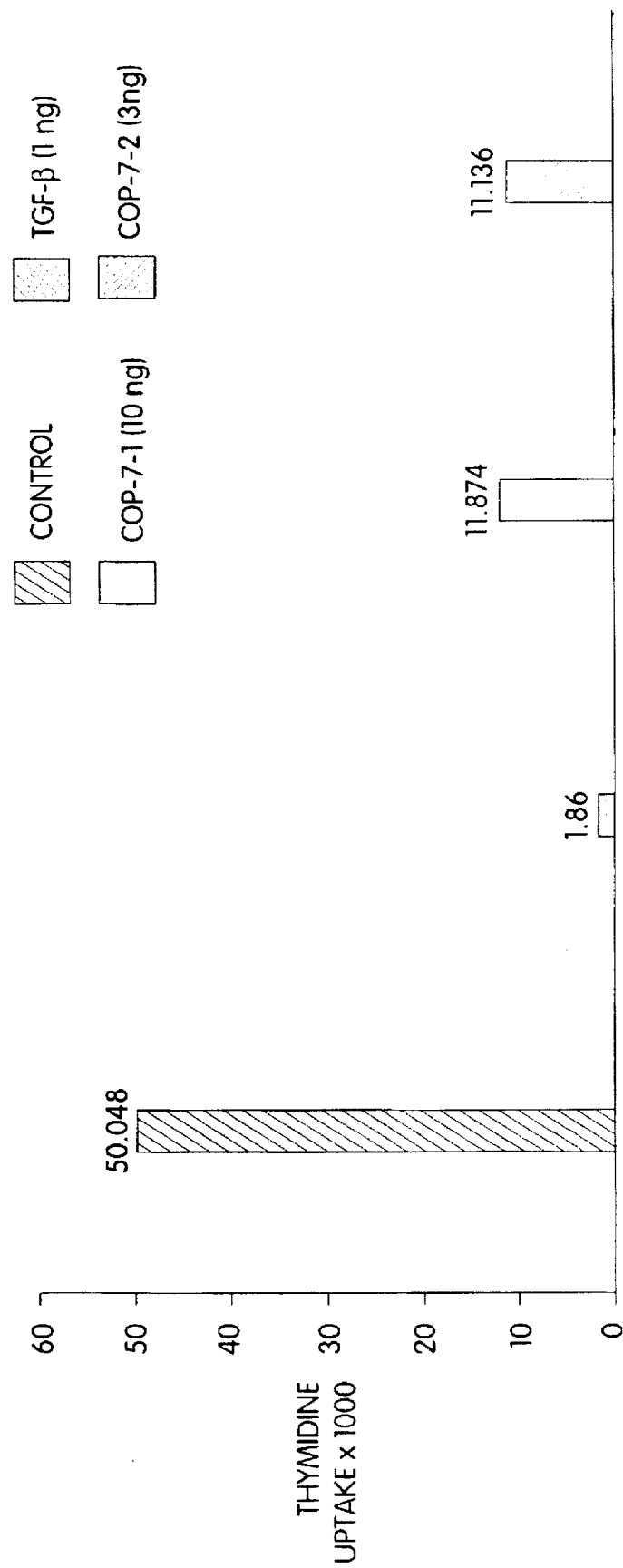
FIG. 3A and 3B graph the antiproliferative effect of morphogens on mink lung cells.
Figure 3B:
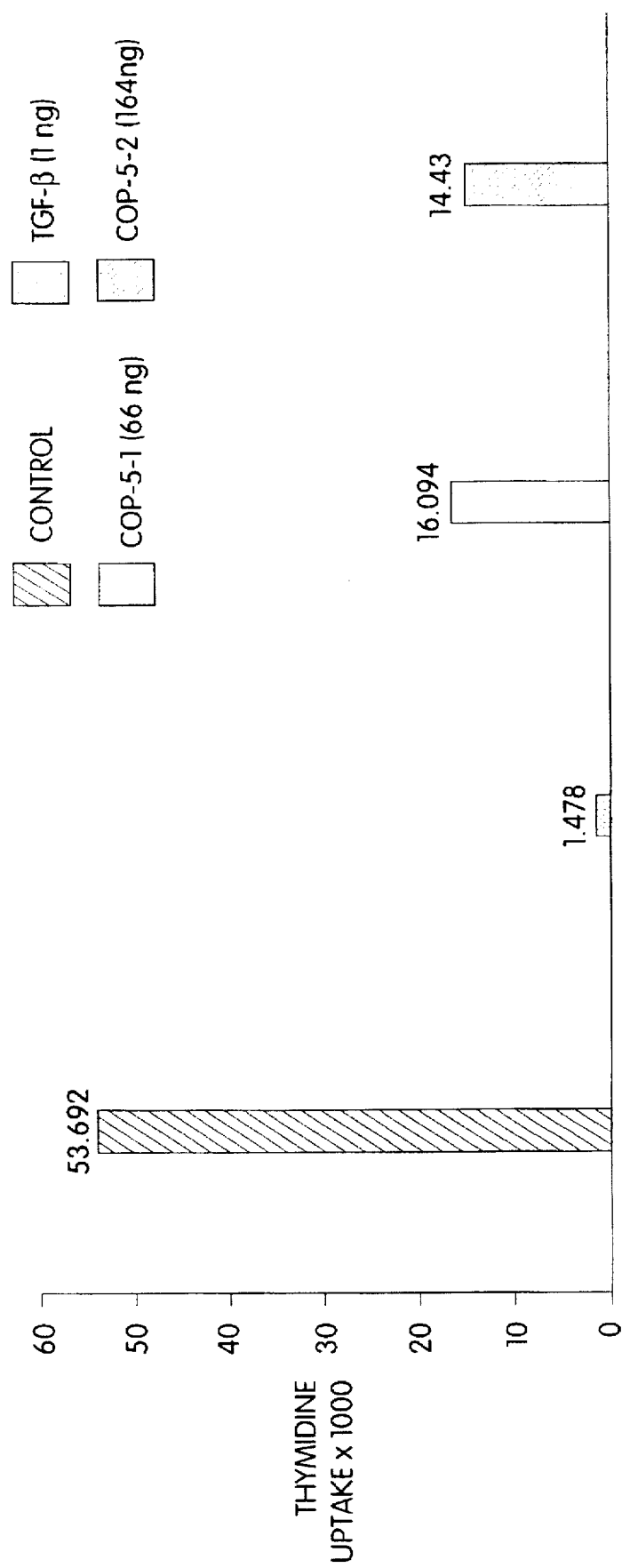
Figure 4A:
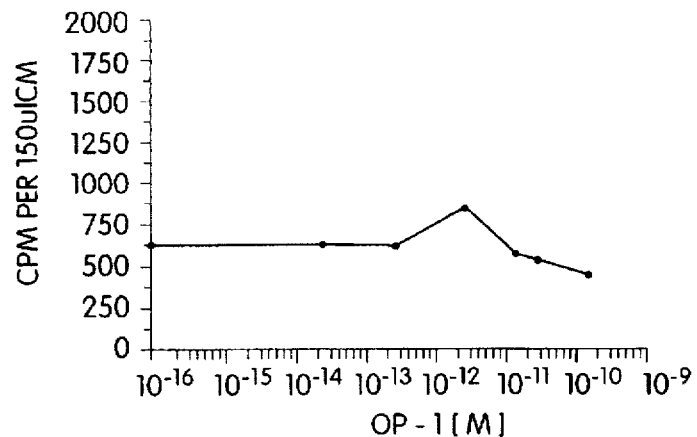
FIG. 4A–4D graphs the effects of a morphogen (e.g., OP-1, FIGS. 4A and 4C) and TGF-β (FIG. 4B and 4D) on collagen (4A and 4B) and hyaluronic acid (4C and 4D) production in primary fibroblast cultures.
Figure 4B:
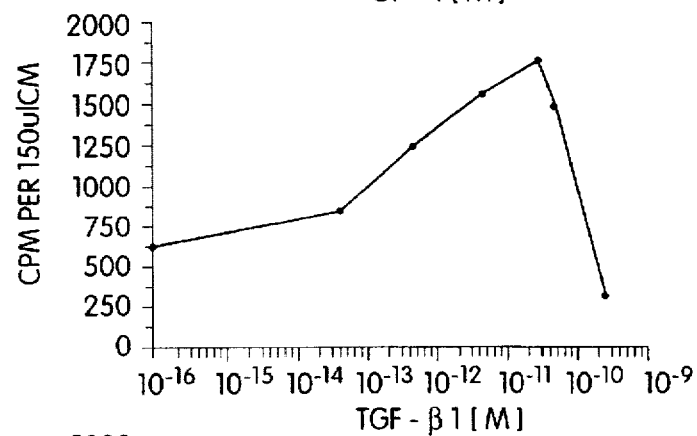
Figure 4C:
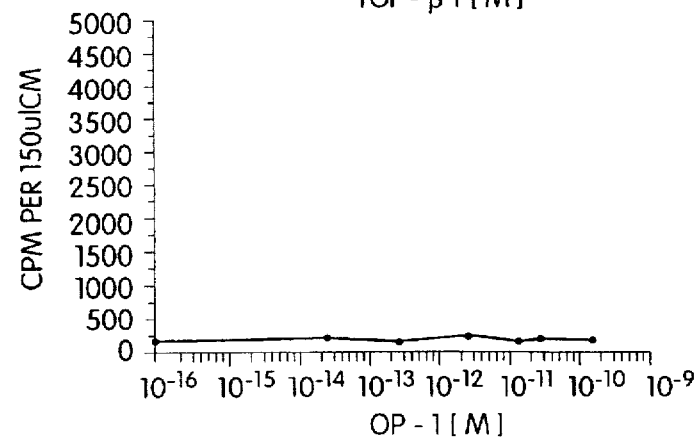
Figure 4D:
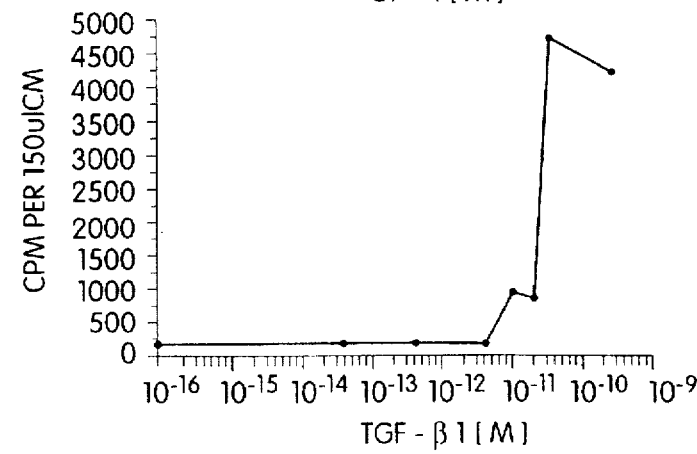

The results are presented in FIG. 3A and 3B. The antiproliferative effect of the various morphogens tested was expressed as the counts of 3H-thymidine (× 1000) integrated into DNA. In this example, the biosynthetic constructs COP-5 and COP-7 were tested in duplicate: COP-7-1 (10 ng) and COP-7-2 (3 ng, FIG. 3A), and COP-5-1 (66 ng) and COP-5-2 (164 ng, FIG. 3B.) Morphogens were compared with untreated cells (negative control) and TGF-β (1 ng), a local-acting factor also known to inhibit epithelial cell proliferation. COP-5 and COP-7 previously have been shown to have osteogenic activity, capable of inducing the complete cascade resulting in endochondral bone formation in a standard rat bone assay (see U.S. Pat. No. 5,011,691.) As is evident in the figure, the morphogens significantly inhibit cell epithelial cell proliferation. Similar experiments, performed with the morphogens COP-16 and bOP (bone-purified osteogenic protein, a dimeric protein comprising CBMP2 and OP-1) and recombinant OP-1 also inhibit cell proliferation. bOP and COP-16 also induce endochondral bone formation (see U.S. Pat. Nos. 4,968,590 and 5,011,691)

Example 8
Morphogen Inhibition of Cellular and Humoral Inflammatory Response Morphogens described herein inhibit multinucleation of mononuclear phagocytic cells under conditions where these cells normally would be activated, e.g., in response to a tissue injury or the presence of a foreign substance. For example, and as described in U.S. patent application Ser. No. 07/938,336, filed Aug. 28, 1992, abandoned and continued as Ser. Nos. 08/445,467 and 08/600,352, in the absence of morphogen, an implanted substrate material (e.g., implanted subcutaneously) composed of, for example, mineralized bone, a ceramic such as titanium oxide or any other substrate that provokes multinucleated giant cell formation, rapidly becomes surrounded by multinucleated giant cells, e.g., activated phagocytes stimulated to respond and destroy the foreign object. In the presence of morphogen however, the recruited cells remain in their mononuclear precursor form and the matrix material is undisturbed. Accordingly, the morphogens' effect in maintaining the integrity of the GI tract luminal lining also may include inhibiting activation of these immune effector cells.

In addition, the morphogens described herein also suppress antibody production stimulated in response to a foreign antigen in a mammal. Specifically, when bovine bone collagen matrix alone was implanted in a bony site in a rat, a standard antibody response to the collagen was stimulated in the rat as determined by standard anti-bovine collagen ELISA experiments performed on blood samples taken at four week intervals following implantation (e.g., between 12 and 20 weeks.) Serum anti-collagen antibody titers, measured by ELISA essentially following the procedure described by Nagler-Anderson et al, (1986) *PNAS* 83:7443–7446, the disclosure of which is incorporated herein by reference, increased consistently throughout the experiment. However, when the matrix was implanted together with a morphogen (e.g., OP-1, dispersed in the matrix and adsorbed thereto, essentially as described in U.S. Pat. No. 4,968,590) anti-bovine collagen antibody production was suppressed significantly. This ability of morphogen to suppress the humoral response is further evidence of morphogen utility in alleviating tissue damage associated with GI tract ulceration.

Example 9
Morphogen Effect on Fibrogenesis and Scar Tissue Formation

The morphogens described herein induce tissue morphogenesis of damaged or lost tissue. The ability of these proteins to regenerate new tissue enhances the anti-inflammatory effect of these proteins. Provided below are a series of in vitro experiments demonstrating the ability of morphogens to induce migration and accumulation of mesenchymal cells. In addition, the experiments demonstrate that morphogens, unlike TGF-β, do not stimulate fibrogenesis or scar tissue formation. Specifically, morphogens do not stimulate production of collagen, hyaluronic acid (HA) or metalloproteinases in primary fibroblasts, all of which are associated with fibrogenesis or scar tissue formation. By contrast, TGF-β, a known inducer of fibrosis, but not of tissue morphogenesis as defined herein, does stimulate production of these markers of fibrosis.

Chemotaxis and migration of mesenchymal progenitor cells were measured in modified Boyden chambers essentially as described by Fava, R. A. et al (1991) *J. Exp. Med.* 173: 1121–1132, the disclosure of which is incorporated herein by reference, using polycarbonate filters of 2, 3 and 8 micron ports to measure migration of progenitor neutrophils, monocytes and fibroblasts. Chemotaxis was measured over a range of morphogen concentrations, e.g., $10^{-20}$M to $10^{-12}$M OP-1. For progenitor neutrophils and monocytes, $10^{-18}$–$10^{-17}$M OP-1 consistently induced maximal migration, and $10^{-14}$ to $10^{-13}$M OP-1 maximally induced migration of progenitor fibroblasts. In all cases the chemotactic activity could be inhibited with anti-OP-1 antibody. Similar migration activities also were measured and observed with TGF-β.

The effect of morphogen on fibrogenesis was determined by evaluating fibroblast production of hyaluronic acid (HA), collagen, collagenase and tissue inhibitor of metalloproteinases (TIMP).

Human fibroblasts were established from explants of infant foreskins and maintained in monolayer culture using standard culturing procedures. (See, for example, (1976) *J. Exp. Med.* 144: 1188–1203.) Briefly, fibroblasts were grown in maintenance medium consisting of Eagle's MEM, supplemented with nonessential amino acids, ascorbic acid (50 µg/ml), NaHCO$_3$ and HEPES buffers (pH 7.2), penicillin (100 U/ml), streptomycin (100 µg/ml), amphotericin B (1 µg/ml) and 9% heat inactivated FCS. Fibroblasts used as target cells to measure chemotaxis were maintained in 150 mm diameter glass petri dishes. Fibroblasts used in assays to measure synthesis of collagen, hyaluronic acid, collagenase and tissue inhibitors of metalloproteinases (TIMP) were grown in 100 mm diameter plastic tissue culture petri dishes.

The effects of morphogen on fibroblast production of hyaluronic acid, collagens, collagenase and TIMP were determined by standard assays (See, for example, Postteth- waite et al. (1989) *J. Clin. Invest.* 83: 629–636, Postteth- waithe (1988) *J./Cell Biol.* 106: 311–318 and Clark et al (1985) *Arch. Bio-chem Biophys.* 241: 36–44, the disclosures of which are incorporated by reference.) For these assays, fibroblasts were transferred to 24-well tissue culture plates at a density of $8 \times 10^4$ cells per well. Fibroblasts were grown confluency in maintenance medium containing 9% FCS for 72 h and then grown in serum-free maintenance medium for 24 h. Medium was then removed from each well and various concentrations of OP-1 (recombinantly produced mature or soluble form) or TGF-β-1 (R&D Systems, Minneapolis) in 50 µl PBS were added to triplicate wells containing the confluent fibroblast monolayers. For experiments that measured production of collagenase and TIMP, maintenance medium (450 µl) containing 5% FCS was added to each well, and culture supernatants were harvested from each well 48 h later and stored at −70° C. until assayed. For experiments that assessed HA production, maintenance medium (450 µl) containing 2.5% FCS was added to each well, and cultures grown for 48 h. For experiments that measured fibroblast production of collagens, serum-free maintenance medium (450 µl) without non-essential amino acids was added to each well and cultures grown for 72 h. Fibroblast production of HA was measured by labeling newly synthesized glycosaminoglycans (GAG) with [$^3$H]-acetate the last 24 h of culture and quantitating released radioactivity after incubation with hyaluronidase from *Streptomyces hyalurolyticus* (ICN Biochemicals, Cleveland, Ohio) which specifically degrades hyaluronic acid. Production of total collagen by fibroblasts was measured using a collagenase-sensitive protein assay that reflects [$^3$H]-proline incorporation the last 24 h of culture into newly synthesized collagens. Collagenase and TIMP protein levels in fibroblast cultures supernatants was measured by specific ELISAs.

As shown in FIG. 4, OP1 does not stimulate significant collagen or HA production, as compared with TGF-β. In the figure, panel A shows OP-1 efect on collagen production, panel B shows TGF-β effect on collagen production, and panels C and D show OP-1 (panel C) and TGF-β (panel D) effect on HA production. The morphogen results were the same whether the soluble or mature form of OP1 was used. By contrast, the latent form of TGF-β (e.g., pro domain-associated form of TGF-β) was not active.

Example 10

Screening Assay for Candidate Compounds which Alter Endogenous Morphogen Levels

Candidate compound(s) which may be administered to affect the level of a given morphogen may be found using the following screening assay, in which the level of morphogen production by a cell type which produces measurable levels of the morphogen is determined with and without incubating the cell in culture with the compound, in order to assess the effects of the compound on the cell. This can be accomplished by detection of the morphogen either at the protein or RNA level. A more detailed description also may be found in U.S. patent application Ser. No. 07/752,861, filed Aug. 30, 1991, abandoned and continued as U.S. patent application Ser. Nos. 08/278/729, 08/451,953 and 08/643, 563 incorporated therefor by reference.

10.1 Growth of Cells in Culture

Cell cultures of kidney, adrenals, urinary bladder, brain, or other organs, may be prepared as described widely in the literature. For example, kidneys may be explanted from neonatal or new born or young or adult rodents (mouse or rat) and used in organ culture as whole or sliced (1–4 mm) tissues. Primary tissue cultures and established cell lines, also derived from kidney, adrenals, urinary, bladder, brain, mammary, or other tissues may be established in multiwell plates (6 well or 24 well) according to conventional cell culture techniques, and are cultured in the absence or presence of serum for a period of time (1–7 days). Cells may be cultured, for example, in Dulbecco's Modified Eagle medium (Gibco, Long Island, N.Y.) containing serum (e.g., fetal calf serum at 1%–10%, Gibco) or in serum-deprived medium, as desired, or in defined medium (e.g., containing insulin, transferrin, glucose, albumin, or other growth factors).

Samples for testing the level of morphogen production includes culture supernatants or cell lysates, collected periodically and evaluated for OP-1 production by immunoblot analysis (Sambrook et al., eds., 1989, Molecular Cloning, Cold Spring Harbor Press, Cold Spring Harbor, N.Y.), or a portion of the cell culture itself, collected periodically and used to prepare polyA+ RNA for RNA analysis. To monitor de novo OP-1 synthesis, some cultures are labeled according to conventional procedures with an $^{35}$S-methionine/$^{35}$S-cysteine mixture for 6–24 hours and then evaluated to OP-1 synthesis by conventional immunoprecipitation methods.

10.2 Determination of Level of Morphogenic Protein

In order to quantitate the production of a morphogenic protein by a cell type, an immunoassay may be performed to detect the morphogen using a polyclonal or monoclonal antibody specific for that protein. For example, OP-1 may be detected using a polyclonal antibody specific for OP-1 in an ELISA, as follows.

1 µg/100 µl of affinity-purified polyclonal rabbit IgG specific for OP-1 is added to each well of a 96-well plate and incubated at 37° C. for an hour. The wells are washed four times with 0.167M sodium borate buffer with 0.15M NaCl (BSB), pH 8.2, containing 0.1% Tween 20. To minimize non-specific binding, the wells are blocked by filling completely with 1% bovine serum albumin (BSA) in BSB and incubating for 1 hour at 37° C. The wells are then washed four times with BSB containing 0.1% Tween 20. A 100 µl aliquot of an appropriate dilution of each of the test samples of cell culture supernatant is added to each well in triplicate and incubated at 37° C. for 30 min. After incubation, 100 μl biotinylated rabbit anti-OP-1 serum (stock solution is about 1 mg/ml and diluted 1:400 in BSB containing 1% BSA before use) is added to each well and incubated at 37° C. for 30 min. The wells are then washed four times with BSB containing 0.1% Tween 20. 100 μl strepavidin-alkaline phosphatase (Southern Biotechnology Associates, Inc. Birmingham, Ala., diluted 1:2000 in BSB containing 0.1% Tween 20 before use) is added to each well and incubated at 37° C. for 30 min. The plates are washed four times with 0.5M Tris buffered Saline (TBS), pH 7.2. 50 μl substrate (ELISA Amplification System Kit; Life Technologies, Inc., Bethesda, Md.) is added to each well incubated at room temperature for 15 min. Then, 50 μl amplifier (from the same amplification system kit) is added and incubated for another 15 min at room temperature. The reaction is stopped by the addition of 50 μl 0.3M sulphuric acid. The OD at 490 nm of the solution in each well is recorded. To quantitate OP-1 in culture media, a OP-1 standard curve is performed in parallel with the test samples.

Polyclonal antibody may be prepared as follows. Each rabbit is given a primary immunization of 100 ug/500 μl *E. coli* produced OP-1 monomer (amino acids 328–431 in SEQ ID NO:5) in 0.1% SDS mixed with 500 μl Complete Freund's Adjuvant. The antigen is injected subcutaneously at multiple sites on the back and flanks of the animal. The rabbit is boosted after a month in the same manner using incomplete Freund's Adjuvant. Test bleeds are taken from the ear vein seven days later. Additional boosts and test bleeds are performed at monthly intervals until antibody against OP-1 is detected in the serum using an ELISA assay.

Then, the rabbit is boosted with 100 μg of antigen and bled (15 ml per bleed) at days seven and ten after boosting.

Monoclonal antibody specific for a given morphogen may be prepared as follows. A mouse is given two injections of *E. coli* produced OP-1 monomer. The first injection contains 100μg of OP-1 in complete Freund's adjuvant and is given subcutaneously. The second injection contains 50 μg of OP-1 in incomplete adjuvant and is given intraperitoneally. The mouse then receives a total of 230 μg of OP-1 (amino acids 307–431 in SEQ ID NO:5) in four intraperitoneal injections at various times over an eight month period. One week prior to fusion, the mouse is boosted intraperitoneally with 100 μg of OP-1 (307–431) and 30 μg of the N-terminal peptide ($Ser_{293}$-$Asn_{309}$-Cys) conjugated through the added cysteine to bovine serum albumin with SMCC crosslinking agent. This boost was repeated five days (IP), four days (IP), three days (IP) and one day (IV) prior to fusion. The mouse spleen cells are then fused to myeloma (e.g., 653) cells at a ratio of 1:1 using PEG 1500 (Boeringer Mannheim), and the cell fusion is plated and screened for OP-1-specific antibodies using OP-1 (307–431) as antigen. The cell fusion and monoclonal screening then are according to standard procedures well described in standard texts widely available in the art.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

---

What is claimed is:

1. A method for protecting the integrity of a gastrointestinal lining in a mammal, comprising administering to said mammal a morphogen comprising a dimeric protein that comprises an amino acid sequence selected from the group consisting of:

(a) a sequence having at least 70% homology with the C-terminal seven cysteine domain of human OP-1, residues 38–139 of Seq. ID No. 5; and (b) a sequence defined by Generic Sequence 6, Seq. ID No. 31 ; and wherein said morphogen induces tissue-specific morphogenesis of gastrointestinal lining or bone in an in vivo assay.

2. The method of claim 1 wherein said mammal is suspected to have xerostomia, oral mucositis, gastric ulcer, duodenal ulcer, ulcerative colitis, proctitis, regional enteritis, necrotizing enterocolitis, or inflammatory bowel disease.

3. The method of claim 1 wherein said mammal is at risk of gastrointestinal ulceration associated with chemotoxicity.

4. The method of claim 1 wherein said mammal has cancer.

5. The method of claim 1 wherein said morphogen has greater than 60% identity with said C-terminal seven-cysteine domain of human OP-1.

6. The method of claim 1 wherein said morphogen comprises a sequence defined by OPX, Seq. ID No. 29.

7. The method of claim 1 wherein the amino acid sequence of said morphogen comprises a sequence selected from the group consisting of the C-terminal seven-cysteine domain of human OP-1, mouse OP-1, human OP-2, mouse OP-2, DPP, Vgl, Vgr-1, CBMP2A, CBMP2B, BMP3, GDF-1, 60A, BMP5 and BMP6 (Seq. ID Nos. 5 (residues 38–139), 6 (residues 38–139), 7 (residues 38–139), 8 (residues 38–139), 9, 10, 11, 12, 13, 14, 25 (residues 354–455), 26, 27 and 28), or a naturally-occurring or biosynthetic variant of any of the foregoing, provided that said variant induces tissue-specific morphogenesis of gastrointestinal lining or bone in an in vivo assay.

8. The method of claim 1 wherein said morphogen is obtained from the milk or serum of a mammal or from the culture supernatant of morphogen-secreting mammalian cells.

9. The method of claim 1 wherein said morphogen further comprises at least one prodomain polypeptide encoded by a nucleic acid encoding the pro form of a morphogen polypeptide selected from the group consisting of human OP-1, mouse OP-1, human OP-2, Mouse OP-2, DPP, Vgl, Vgr-1, CBMP2A, CBMP2B, BMP3, GDF-1, 60A, BMP5 and BMP6 (Seq. ID Nos. 9, 10, 11, 12, 13, 17, 19, 21, 23, 25, 26, 27, 28 and 33), and naturally-occurring or biosynthetic variants thereof, wherein said morphogen induced tissue-specific morphogenesis of gastrointestinal lining or bone in an in vivo assay.

10. The method of claim 1 wherein said mammal is a human.

11. The method of claim 3 wherein said chemotoxicity is produced by a radiotherapeutic agent.

12. The method of claim 3 or 4, comprising the step of administering said morphogen to oral mucosa tissue in said mammal.

13. The method of claim 7 wherein said amino acid sequence comprises the C-terminal seven-cysteine domain human OP-1 or a naturally-occurring or biosynthetic variant thereof.

14. The method of claim 9 wherein said prodomain polypeptide is noncovalently complexed with said dimeric protein.

15. The method of claim 10 wherein said morphogen is administered systemically.

16. The method of claim 10 wherein said morphogen administered orally, rectally or parenterally.

17. The method of claim 10 wherein said morphogen is administered locally.

18. The method of claim 10 wherein said morphogen is administered to said human at a concentration of less than about 100 µg morphogen/kg body weight.

19. The method of claim 16 wherein said morphogen is administered orally in an ingestible controlled-release delivery vehicle.

20. The method of claim 17 wherein said morphogen is administered in a mouthwash solution.

21. The method of claim 17 wherein said morphogen is administered topically.

22. The method of claim 18 wherein said concentration is less than about 30 µg morphogen/kg body weight.

23. The method of claim 21 wherein said morphogen is dispersed in a tissue adhesive composition.

24. The method of claim 22 wherein said concentration is less than about 10 µg morphogen/kg body weight.

* * * * *

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
        ( A ) LENGTH: 97 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..97
        ( D ) OTHER INFORMATION: /label=GENERIC-SEQ-1
        / note= "EACH XAA INDICATES ONE OF THE 20 NATURALLY
        OCCURRING L- ISOMER, ALPHA-AMINO ACIDS, OR A DERIVATIVE
        THEREOF"

( x i ) SEQUENCE DESCRIPTION: SEQ ID NO:1:

```
Xaa Xaa Xaa Xaa Xaa Xaa Xaa Xaa Xaa Xaa Xaa Xaa Xaa Xaa Xaa Xaa
 1               5                   1 0                 1 5

Xaa Xaa Xaa Xaa Xaa Xaa Xaa Xaa Cys Xaa Xaa Xaa Cys Xaa Xaa Xaa
                 2 0                 2 5                 3 0

Xaa Xaa Xaa Xaa Xaa Xaa Xaa Xaa Xaa Xaa Xaa Xaa Xaa Xaa Xaa Xaa
             3 5                 4 0                 4 5

Xaa Xaa Xaa Xaa Xaa Xaa Xaa Xaa Xaa Xaa Xaa Xaa Cys Cys Xaa Xaa
```

5,739,107

-continued

```
                      50                      55                      60
Xaa Xaa Xaa Xaa Xaa Xaa Xaa Xaa Xaa Xaa Xaa Xaa Xaa Xaa Xaa Xaa
 65                  70                              75                  80

Xaa Xaa Xaa Xaa Xaa Xaa Xaa Xaa Xaa Xaa Xaa Xaa Xaa Cys Xaa Cys
                 85                          90                  95

Xaa
```

( 2 ) INFORMATION FOR SEQ ID NO:2:

( i ) SEQUENCE CHARACTERISTICS:
        ( A ) LENGTH: 97 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..97
        ( D ) OTHER INFORMATION: /label=GENERIC-SEQ-2
           / note= "EACH XAA INDICATES ONE OF THE 20 NATURALLY
           OCCURING L- ISOMER, ALPHA-AMINO ACIDS, OR A DERIVATIVE
           THEREOF"

( x i ) SEQUENCE DESCRIPTION: SEQ ID NO:2:

```
Xaa Xaa Xaa Xaa Xaa Xaa Xaa Xaa Xaa Xaa Xaa Xaa Xaa Xaa Xaa Xaa
 1                   5                          10                  15

Xaa Xaa Xaa Xaa Xaa Xaa Xaa Xaa Cys Xaa Xaa Xaa Cys Xaa Xaa Xaa
                 20                          25                  30

Xaa Xaa Xaa Cys Xaa Xaa Xaa Xaa Xaa Xaa Xaa Xaa Xaa Xaa Xaa Xaa
         35                          40                  45

Xaa Xaa Xaa Xaa Xaa Xaa Xaa Xaa Xaa Xaa Xaa Cys Cys Xaa Xaa Xaa
 50                          55                  60

Xaa Xaa Xaa Xaa Xaa Xaa Xaa Xaa Xaa Xaa Xaa Xaa Xaa Xaa Xaa Xaa
 65                  70                              75                  80

Xaa Xaa Xaa Xaa Xaa Xaa Xaa Xaa Xaa Xaa Xaa Xaa Xaa Cys Xaa Cys
                 85                          90                  95

Xaa
```

( 2 ) INFORMATION FOR SEQ ID NO:3:

( i ) SEQUENCE CHARACTERISTICS:
        ( A ) LENGTH: 97 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..97
        ( D ) OTHER INFORMATION: /label=GENERIC-SEQ-3
           / note= "WHEREIN EACH XAA IS INDEPENDENTLY SELECTED FROM
           A GROUP OF ONE OR MORE SPECIFIED AMINO ACIDS AS DEFINED
           IN THE SPECIFICATION "

( x i ) SEQUENCE DESCRIPTION: SEQ ID NO:3:

```
Leu Tyr Val Xaa Phe Xaa Xaa Xaa Gly Trp Xaa Xaa Trp Xaa Xaa Ala
 1                   5                          10                  15

Pro Xaa Gly Xaa Xaa Ala Xaa Tyr Cys Xaa Gly Xaa Cys Xaa Xaa Pro
                 20                          25                  30

Xaa Xaa Xaa Xaa Xaa Xaa Xaa Xaa Asn His Ala Xaa Xaa Xaa Xaa Leu
         35                          40                  45
```

Xaa Xaa Xaa Xaa Xaa Xaa Xaa Xaa Xaa Xaa Xaa Xaa Cys Cys Xaa Pro
            50                          55                      60

Xaa Xaa Xaa Xaa Xaa Xaa Xaa Xaa Leu Xaa Xaa Xaa Xaa Xaa Xaa Xaa
65                       70                      75                              80

Val Xaa Leu Xaa Xaa Xaa Xaa Xaa Met Xaa Val Xaa Xaa Cys Gly Cys
                    85                      90                          95

Xaa (2) INFORMATION FOR SEQ ID NO:4:

(i) SEQUENCE CHARACTERISTICS:
      (A) LENGTH: 102 amino acids
      (B) TYPE: amino acid
      (C) STRANDEDNESS: single
      (D) TOPOLOGY: linear (ii) MOLECULE TYPE: protein (ix) FEATURE:
      (A) NAME/KEY: Protein
      (B) LOCATION: 1..102
      (D) OTHER INFORMATION: /label=GENERIC-SEQ-4
        / note= "WHEREIN EACH XAA IS INDEPENDENTLY SELECTED FROM
        A GROUP OF ONE OR MORE SPECIFIED AMINO ACIDS AS DEFINED
        IN THE SPECIFICATION"

(xi) SEQUENCE DESCRIPTION: SEQ ID NO:4:

Cys Xaa Xaa Xaa Xaa Leu Tyr Val Xaa Phe Xaa Xaa Xaa Gly Trp Xaa
1                   5                       10                          15

Xaa Trp Xaa Xaa Ala Pro Xaa Gly Xaa Xaa Ala Xaa Tyr Cys Xaa Gly
            20                      25                      30

Xaa Cys Xaa Xaa Pro Xaa Xaa Xaa Xaa Xaa Xaa Xaa Xaa Asn His Ala
        35                      40                      45

Xaa Xaa Xaa Xaa Leu Xaa Xaa Xaa Xaa Xaa Xaa Xaa Xaa Xaa Xaa Xaa
            50                      55                      60

Xaa Cys Cys Xaa Pro Xaa Xaa Xaa Xaa Xaa Xaa Xaa Leu Xaa Xaa
65                      70                      75                              80

Xaa Xaa Xaa Xaa Xaa Val Xaa Leu Xaa Xaa Xaa Xaa Xaa Met Xaa Val
                    85                      90                          95

Xaa Xaa Cys Gly Cys Xaa
                100

(2) INFORMATION FOR SEQ ID NO:5:

(i) SEQUENCE CHARACTERISTICS:
      (A) LENGTH: 139 amino acids
      (B) TYPE: amino acid
      (C) STRANDEDNESS: single
      (D) TOPOLOGY: linear (ii) MOLECULE TYPE: protein (ix) FEATURE:
      (A) NAME/KEY: Protein
      (B) LOCATION: 1..139
      (D) OTHER INFORMATION: /note= "HOP-1 (MATURE FORM)"

(xi) SEQUENCE DESCRIPTION: SEQ ID NO:5:

Ser Thr Gly Ser Lys Gln Arg Ser Gln Asn Arg Ser Lys Thr Pro Lys
1                   5                       10                          15

Asn Gln Glu Ala Leu Arg Met Ala Asn Val Ala Glu Asn Ser Ser Ser
            20                      25                      30

Asp Gln Arg Gln Ala Cys Lys Lys His Glu Leu Tyr Val Ser Phe Arg
            35                      40                      45

```
Asp Leu Gly Trp Gln Asp Trp Ile Ile Ala Pro Glu Gly Tyr Ala Ala
    50              55                  60

Tyr Tyr Cys Glu Gly Glu Cys Ala Phe Pro Leu Asn Ser Tyr Met Asn
65              70                  75                      80

Ala Thr Asn His Ala Ile Val Gln Thr Leu Val His Phe Ile Asn Pro
                85                  90                      95

Glu Thr Val Pro Lys Pro Cys Cys Ala Pro Thr Gln Leu Asn Ala Ile
            100             105                     110

Ser Val Leu Tyr Phe Asp Asp Ser Ser Asn Val Ile Leu Lys Lys Tyr
        115             120                     125

Arg Asn Met Val Val Arg Ala Cys Gly Cys His
    130             135
```

(2) INFORMATION FOR SEQ ID NO:6:

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..139
        (D) OTHER INFORMATION: /note= "MOP-1 (MATURE FORM)"

(xi) SEQUENCE DESCRIPTION: SEQ ID NO:6:

```
Ser Thr Gly Gly Lys Gln Arg Ser Gln Asn Arg Ser Lys Thr Pro Lys
1           5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50              55                  60

Tyr Tyr Cys Glu Gly Glu Cys Ala Phe Pro Leu Asn Ser Tyr Met Asn
65              70                  75                      80

Ala Thr Asn His Ala Ile Val Gln Thr Leu Val His Phe Ile Asn Pro
                85                  90                      95

Asp Thr Val Pro Lys Pro Cys Cys Ala Pro Thr Gln Leu Asn Ala Ile
            100             105                     110

Ser Val Leu Tyr Phe Asp Asp Ser Ser Asn Val Ile Leu Lys Lys Tyr
        115             120                     125

Arg Asn Met Val Val Arg Ala Cys Gly Cys His
    130             135
```

(2) INFORMATION FOR SEQ ID NO:7:

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..139
        (D) OTHER INFORMATION: /note= "HOP-2 (MATURE FORM)"

( x i ) SEQUENCE DESCRIPTION: SEQ ID NO:7:

```
Ala Val Arg Pro Leu Arg Arg Gln Pro Lys Lys Ser Asn Glu Leu
1               5                   10                  15

Pro Gln Ala Asn Arg Leu Pro Gly Ile Phe Asp Asp Val His Gly Ser
                20                  25                  30

His Gly Arg Gln Val Cys Arg Arg His Glu Leu Tyr Val Ser Phe Gln
            35                  40                  45

Asp Leu Gly Trp Leu Asp Trp Val Ile Ala Pro Gln Gly Tyr Ser Ala
        50                  55                  60

Tyr Tyr Cys Glu Gly Glu Cys Ser Phe Pro Leu Asp Ser Cys Met Asn
65                      70                  75                  80

Ala Thr Asn His Ala Ile Leu Gln Ser Leu Val His Leu Met Lys Pro
                85                      90                  95

Asn Ala Val Pro Lys Ala Cys Cys Ala Pro Thr Lys Leu Ser Ala Thr
            100                 105                 110

Ser Val Leu Tyr Tyr Asp Ser Ser Asn Asn Val Ile Leu Arg Lys His
        115                 120                 125

Arg Asn Met Val Val Lys Ala Cys Gly Cys His
        130                 135
```

( 2 ) INFORMATION FOR SEQ ID NO:8:

( i ) SEQUENCE CHARACTERISTICS:
    ( A ) LENGTH: 139 amino acids
    ( B ) TYPE: amino acid
    ( C ) STRANDEDNESS: single
    ( D ) TOPOLOGY: linear ( i i ) MOLECULE TYPE: protein ( i x ) FEATURE:
    ( A ) NAME/KEY: Protein
    ( B ) LOCATION: 1..139
    ( D ) OTHER INFORMATION: /note= "MOP-2 (MATURE FORM)"

( x i ) SEQUENCE DESCRIPTION: SEQ ID NO:8:

```
Ala Ala Arg Pro Leu Lys Arg Arg Gln Pro Lys Lys Thr Asn Glu Leu
1               5                   10                  15

Pro His Pro Asn Lys Leu Pro Gly Ile Phe Asp Asp Gly His Gly Ser
                20                  25                  30

Arg Gly Arg Glu Val Cys Arg Arg His Glu Leu Tyr Val Ser Phe Arg
            35                  40                  45

Asp Leu Gly Trp Leu Asp Trp Val Ile Ala Pro Gln Gly Tyr Ser Ala
        50                  55                  60

Tyr Tyr Cys Glu Gly Glu Cys Ala Phe Pro Leu Asp Ser Cys Met Asn
65                      70                  75                  80

Ala Thr Asn His Ala Ile Leu Gln Ser Leu Val His Leu Met Lys Pro
                85                      90                  95

Asp Val Val Pro Lys Ala Cys Cys Ala Pro Thr Lys Leu Ser Ala Thr
            100                 105                 110

Ser Val Leu Tyr Tyr Asp Ser Ser Asn Asn Val Ile Leu Arg Lys His
        115                 120                 125

Arg Asn Met Val Val Lys Ala Cys Gly Cys His
        130                 135
```

( 2 ) INFORMATION FOR SEQ ID NO:9:

( i ) SEQUENCE CHARACTERISTICS:
    ( A ) LENGTH: 101 amino acids
    ( B ) TYPE: amino acid (C) STRANDEDNESS: single
(D) TOPOLOGY: linear (ii) MOLECULE TYPE: protein (ix) FEATURE:
 (A) NAME/KEY: Protein
 (B) LOCATION: 1..101
 (D) OTHER INFORMATION: /note= "CBMP-2A(FX)"

(xi) SEQUENCE DESCRIPTION: SEQ ID NO:9:

```
Cys Lys Arg His Pro Leu Tyr Val Asp Phe Ser Asp Val Gly Trp Asn
1               5                   10                  15

Asp Trp Ile Val Ala Pro Pro Gly Tyr His Ala Phe Tyr Cys His Gly
            20                  25                  30

Glu Cys Pro Phe Pro Leu Ala Asp His Leu Asn Ser Thr Asn His Ala
        35                  40                  45

Ile Val Gln Thr Leu Val Asn Ser Val Asn Ser Lys Ile Pro Lys Ala
    50                  55                  60

Cys Cys Val Pro Thr Glu Leu Ser Ala Ile Ser Met Leu Tyr Leu Asp
65                  70                  75                  80

Glu Asn Glu Lys Val Val Leu Lys Asn Tyr Gln Asp Met Val Val Glu
                85                  90                  95

Gly Cys Gly Cys Arg
                100
```

(2) INFORMATION FOR SEQ ID NO:10:

(i) SEQUENCE CHARACTERISTICS:
 (A) LENGTH: 101 amino acids
 (B) TYPE: amino acid
 (C) STRANDEDNESS: single
 (D) TOPOLOGY: linear (ii) MOLECULE TYPE: protein (ix) FEATURE:
 (A) NAME/KEY: Protein
 (B) LOCATION: 1..101
 (D) OTHER INFORMATION: /note= "CBMP-2B(FX)"

(xi) SEQUENCE DESCRIPTION: SEQ ID NO:10:

```
Cys Arg Arg His Ser Leu Tyr Val Asp Phe Ser Asp Val Gly Trp Asn
1               5                   10                  15

Asp Trp Ile Val Ala Pro Pro Gly Tyr Gln Ala Phe Tyr Cys His Gly
            20                  25                  30

Asp Cys Pro Phe Pro Leu Ala Asp His Leu Asn Ser Thr Asn His Ala
        35                  40                  45

Ile Val Gln Thr Leu Val Asn Ser Val Asn Ser Ser Ile Pro Lys Ala
    50                  55                  60

Cys Cys Val Pro Thr Glu Leu Ser Ala Ile Ser Met Leu Tyr Leu Asp
65                  70                  75                  80

Glu Tyr Asp Lys Val Val Leu Lys Asn Tyr Gln Glu Met Val Val Glu
                85                  90                  95

Gly Cys Gly Cys Arg
                100
```

(2) INFORMATION FOR SEQ ID NO:11:

(i) SEQUENCE CHARACTERISTICS:
 (A) LENGTH: 102 amino acids
 (B) TYPE: amino acid
 (C) STRANDEDNESS: single
 (D) TOPOLOGY: linear ( i i ) MOLECULE TYPE: protein ( i x ) FEATURE:
    ( A ) NAME/KEY: Protein
    ( B ) LOCATION: 1..102
    ( D ) OTHER INFORMATION: /note= "DPP(FX)"

( x i ) SEQUENCE DESCRIPTION: SEQ ID NO:11:

```
Cys Arg Arg His Ser Leu Tyr Val Asp Phe Ser Asp Val Gly Trp Asp
  1               5                  10                  15

Asp Trp Ile Val Ala Pro Leu Gly Tyr Asp Ala Tyr Tyr Cys His Gly
             20                  25                  30

Lys Cys Pro Phe Pro Leu Ala Asp His Phe Asn Ser Thr Asn His Ala
         35                  40                  45

Val Val Gln Thr Leu Val Asn Asn Asn Pro Gly Lys Val Pro Lys
 50                      55                  60

Ala Cys Cys Val Pro Thr Gln Leu Asp Ser Val Ala Met Leu Tyr Leu
 65                  70                      75                  80

Asn Asp Gln Ser Thr Val Val Leu Lys Asn Tyr Gln Glu Met Thr Val
                 85                  90                  95

Val Gly Cys Gly Cys Arg
             100
```

( 2 ) INFORMATION FOR SEQ ID NO:12:

( i ) SEQUENCE CHARACTERISTICS:
        ( A ) LENGTH: 102 amino acids
        ( B ) TYPE: amino acid
        ( C ) STRANDEDNESS: single
        ( D ) TOPOLOGY: linear ( i i ) MOLECULE TYPE: protein ( i x ) FEATURE:
    ( A ) NAME/KEY: Protein
    ( B ) LOCATION: 1..102
    ( D ) OTHER INFORMATION: /note= "VGL(FX)"

( x i ) SEQUENCE DESCRIPTION: SEQ ID NO:12:

```
Cys Lys Lys Arg His Leu Tyr Val Glu Phe Lys Asp Val Gly Trp Gln
  1               5                  10                  15

Asn Trp Val Ile Ala Pro Gln Gly Tyr Met Ala Asn Tyr Cys Tyr Gly
             20                  25                  30

Glu Cys Pro Tyr Pro Leu Thr Glu Ile Leu Asn Gly Ser Asn His Ala
         35                  40                  45

Ile Leu Gln Thr Leu Val His Ser Ile Glu Pro Glu Asp Ile Pro Leu
 50                      55                  60

Pro Cys Cys Val Pro Thr Lys Met Ser Pro Ile Ser Met Leu Phe Tyr
 65                  70                      75                  80

Asp Asn Asn Asp Asn Val Val Leu Arg His Tyr Glu Asn Met Ala Val
                 85                  90                  95

Asp Glu Cys Gly Cys Arg
             100
```

( 2 ) INFORMATION FOR SEQ ID NO:13:

( i ) SEQUENCE CHARACTERISTICS:
        ( A ) LENGTH: 102 amino acids
        ( B ) TYPE: amino acid
        ( C ) STRANDEDNESS: single
        ( D ) TOPOLOGY: linear ( i i ) MOLECULE TYPE: protein ( i x ) FEATURE:
  ( A ) NAME/KEY: Protein
  ( B ) LOCATION: 1..102
  ( D ) OTHER INFORMATION: /note= "VGR-1(FX)"

( x i ) SEQUENCE DESCRIPTION: SEQ ID NO:13:

```
Cys Lys Lys His Glu Leu Tyr Val Ser Phe Gln Asp Val Gly Trp Gln
 1               5                  10                  15

Asp Trp Ile Ile Ala Pro Lys Gly Tyr Ala Ala Asn Tyr Cys Asp Gly
            20                  25                  30

Glu Cys Ser Phe Pro Leu Asn Ala His Met Asn Ala Thr Asn His Ala
         35                  40                  45

Ile Val Gln Thr Leu Val His Val Met Asn Pro Glu Tyr Val Pro Lys
 50                      55                  60

Pro Cys Cys Ala Pro Thr Lys Val Asn Ala Ile Ser Val Leu Tyr Phe
 65              70                  75                  80

Asp Asp Asn Ser Asn Val Ile Leu Lys Lys Tyr Arg Asn Met Val Val
                 85                  90                  95

Arg Ala Cys Gly Cys His
            100
```

( 2 ) INFORMATION FOR SEQ ID NO:14:

( i ) SEQUENCE CHARACTERISTICS:
    ( A ) LENGTH: 106 amino acids
    ( B ) TYPE: amino acid
    ( C ) STRANDEDNESS: single
    ( D ) TOPOLOGY: linear ( i i ) MOLECULE TYPE: protein ( i x ) FEATURE:
    ( A ) NAME/KEY: Protein
    ( B ) LOCATION: 1..106
    ( D ) OTHER INFORMATION: /note= "GDF-1 (FX)"

( x i ) SEQUENCE DESCRIPTION: SEQ ID NO:14:

```
Cys Arg Ala Arg Arg Leu Tyr Val Ser Phe Arg Glu Val Gly Trp His
 1               5                  10                  15

Arg Trp Val Ile Ala Pro Arg Gly Phe Leu Ala Asn Tyr Cys Gln Gly
            20                  25                  30

Gln Cys Ala Leu Pro Val Ala Leu Ser Gly Ser Gly Gly Pro Pro Ala
         35                  40                  45

Leu Asn His Ala Val Leu Arg Ala Leu Met His Ala Ala Ala Pro Gly
 50                      55                  60

Ala Ala Asp Leu Pro Cys Cys Val Pro Ala Arg Leu Ser Pro Ile Ser
 65              70                  75                  80

Val Leu Phe Phe Asp Asn Ser Asp Asn Val Val Leu Arg Gln Tyr Glu
                 85                  90                  95

Asp Met Val Val Asp Glu Cys Gly Cys Arg
             100                 105
```

( 2 ) INFORMATION FOR SEQ ID NO:15:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:15:

```
Cys Xaa Xaa Xaa Xaa
 1           5
```

( 2 ) INFORMATION FOR SEQ ID NO:16:

( i ) SEQUENCE CHARACTERISTICS:
    ( A ) LENGTH: 1822 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 49..1341
    ( D ) OTHER INFORMATION: /product="HOP-1"

( x i ) SEQUENCE DESCRIPTION: SEQ ID NO:16:

```
GGTGCGGGCC CGGAGCCCGG AGCCCGGGTA GCGCGTAGAG CCGGCGCG ATG CAC GTG        57
                                                      Met His Val
                                                        1

CGC TCA CTG CGA GCT GCG GCG CCG CAC AGC TTC GTG GCG CTC TGG GCA        105
Arg Ser Leu Arg Ala Ala Ala Pro His Ser Phe Val Ala Leu Trp Ala
      5              10                 15

CCC CTG TTC CTG CTG CGC TCC GCC CTG GCC GAC TTC AGC CTG GAC AAC        153
Pro Leu Phe Leu Leu Arg Ser Ala Leu Ala Asp Phe Ser Leu Asp Asn
 20                 25                 30                 35

GAG GTG CAC TCG AGC TTC ATC CAC CGG CGC CTC CGC AGC CAG GAG CGG        201
Glu Val His Ser Ser Phe Ile His Arg Arg Leu Arg Ser Gln Glu Arg
                 40                 45                 50

CGG GAG ATG CAG CGC GAG ATC CTC TCC ATT TTG GGC TTG CCC CAC CGC        249
Arg Glu Met Gln Arg Glu Ile Leu Ser Ile Leu Gly Leu Pro His Arg
             55                 60                 65

CCG CGC CCG CAC CTC CAG GGC AAG CAC AAC TCG GCA CCC ATG TTC ATG        297
Pro Arg Pro His Leu Gln Gly Lys His Asn Ser Ala Pro Met Phe Met
         70                 75                 80

CTG GAC CTG TAC AAC GCC ATG GCG GTG GAG GAG GGC GGC GGG CCC GGC        345
Leu Asp Leu Tyr Asn Ala Met Ala Val Glu Glu Gly Gly Gly Pro Gly
     85                 90                 95

GGC CAG GGC TTC TCC TAC CCC TAC AAG GCC GTC TTC AGT ACC CAG GGC        393
Gly Gln Gly Phe Ser Tyr Pro Tyr Lys Ala Val Phe Ser Thr Gln Gly
100                105                110                115

CCC CCT CTG GCC AGC CTG CAA GAT AGC CAT TTC CTC ACC GAC GCC GAC        441
Pro Pro Leu Ala Ser Leu Gln Asp Ser His Phe Leu Thr Asp Ala Asp
                120                125                130

ATG GTC ATG AGC TTC GTC AAC CTC GTG GAA CAT GAC AAG GAA TTC TTC        489
Met Val Met Ser Phe Val Asn Leu Val Glu His Asp Lys Glu Phe Phe
            135                140                145

CAC CCA CGC TAC CAC CAT CGA GAG TTC CGG TTT GAT CTT TCC AAG ATC        537
His Pro Arg Tyr His His Arg Glu Phe Arg Phe Asp Leu Ser Lys Ile
        150                155                160

CCA GAA GGG GAA GCT GTC ACG GCA GCC GAA TTC CGG ATC TAC AAG GAC        585
Pro Glu Gly Glu Ala Val Thr Ala Ala Glu Phe Arg Ile Tyr Lys Asp
    165                170                175

TAC ATC CGG GAA CGC TTC GAC AAT GAG ACG TTC CGG ATC AGC GTT TAT        633
Tyr Ile Arg Glu Arg Phe Asp Asn Glu Thr Phe Arg Ile Ser Val Tyr
180                185                190                195

CAG GTG CTC CAG GAG CAC TTG GGC AGG GAA TCG GAT CTC TTC CTG CTC        681
Gln Val Leu Gln Glu His Leu Gly Arg Glu Ser Asp Leu Phe Leu Leu
                200                205                210

GAC AGC CGT ACC CTC TGG GCC TCG GAG GAG GGC TGG CTG GTG TTT GAC        729
Asp Ser Arg Thr Leu Trp Ala Ser Glu Glu Gly Trp Leu Val Phe Asp
```

```
                                215                                  220                                 225
ATC  ACA  GCC  ACC  AGC  AAC  CAC  TGG  GTG  GTC  AAT  CCG  CGG  CAC  AAC  CTG       777
Ile  Thr  Ala  Thr  Ser  Asn  His  Trp  Val  Val  Asn  Pro  Arg  His  Asn  Leu
          230                            235                      240

GGC  CTG  CAG  CTC  TCG  GTG  GAG  ACG  CTG  GAT  GGG  CAG  AGC  ATC  AAC  CCC       825
Gly  Leu  Gln  Leu  Ser  Val  Glu  Thr  Leu  Asp  Gly  Gln  Ser  Ile  Asn  Pro
     245                           250                           255

AAG  TTG  GCG  GGC  CTG  ATT  GGG  CGG  CAC  GGG  CCC  CAG  AAC  AAG  CAG  CCC       873
Lys  Leu  Ala  Gly  Leu  Ile  Gly  Arg  His  Gly  Pro  Gln  Asn  Lys  Gln  Pro
260                           265                           270                      275

TTC  ATG  GTG  GCT  TTC  TTC  AAG  GCC  ACG  GAG  GTC  CAC  TTC  CGC  AGC  ATC       921
Phe  Met  Val  Ala  Phe  Phe  Lys  Ala  Thr  Glu  Val  His  Phe  Arg  Ser  Ile
                    280                           285                      290

CGG  TCC  ACG  GGG  AGC  AAA  CAG  CGC  AGC  CAG  AAC  CGC  TCC  AAG  ACG  CCC       969
Arg  Ser  Thr  Gly  Ser  Lys  Gln  Arg  Ser  Gln  Asn  Arg  Ser  Lys  Thr  Pro
               295                            300                      305

AAG  AAC  CAG  GAA  GCC  CTG  CGG  ATG  GCC  AAC  GTG  GCA  GAG  AAC  AGC  AGC      1017
Lys  Asn  Gln  Glu  Ala  Leu  Arg  Met  Ala  Asn  Val  Ala  Glu  Asn  Ser  Ser
          310                           315                      320

AGC  GAC  CAG  AGG  CAG  GCC  TGT  AAG  AAG  CAC  GAG  CTG  TAT  GTC  AGC  TTC      1065
Ser  Asp  Gln  Arg  Gln  Ala  Cys  Lys  Lys  His  Glu  Leu  Tyr  Val  Ser  Phe
     325                           330                           335

CGA  GAC  CTG  GGC  TGG  CAG  GAC  TGG  ATC  ATC  GCG  CCT  GAA  GGC  TAC  GCC      1113
Arg  Asp  Leu  Gly  Trp  Gln  Asp  Trp  Ile  Ile  Ala  Pro  Glu  Gly  Tyr  Ala
340                           345                           350                     355

GCC  TAC  TAC  TGT  GAG  GGG  GAG  TGT  GCC  TTC  CCT  CTG  AAC  TCC  TAC  ATG      1161
Ala  Tyr  Tyr  Cys  Glu  Gly  Glu  Cys  Ala  Phe  Pro  Leu  Asn  Ser  Tyr  Met
                    360                           365                      370

AAC  GCC  ACC  AAC  CAC  GCC  ATC  GTG  CAG  ACG  CTG  GTC  CAC  TTC  ATC  AAC      1209
Asn  Ala  Thr  Asn  His  Ala  Ile  Val  Gln  Thr  Leu  Val  His  Phe  Ile  Asn
               375                            380                      385

CCG  GAA  ACG  GTG  CCC  AAG  CCC  TGC  TGT  GCG  CCC  ACG  CAG  CTC  AAT  GCC      1257
Pro  Glu  Thr  Val  Pro  Lys  Pro  Cys  Cys  Ala  Pro  Thr  Gln  Leu  Asn  Ala
          390                           395                      400

ATC  TCC  GTC  CTC  TAC  TTC  GAT  GAC  AGC  TCC  AAC  GTC  ATC  CTG  AAG  AAA      1305
Ile  Ser  Val  Leu  Tyr  Phe  Asp  Asp  Ser  Ser  Asn  Val  Ile  Leu  Lys  Lys
405                           410                           415

TAC  AGA  AAC  ATG  GTG  GTC  CGG  GCC  TGT  GGC  TGC  CAC  TAGCTCCTCC              1351
Tyr  Arg  Asn  Met  Val  Val  Arg  Ala  Cys  Gly  Cys  His
420                      425                           430

GAGAATTCAG  ACCCTTTGGG  GCCAAGTTTT  TCTGGATCCT  CCATTGCTCG  CCTTGGCCAG              1411

GAACCAGCAG  ACCAACTGCC  TTTTGTGAGA  CCTTCCCCTC  CCTATCCCCA  ACTTTAAAGG              1471

TGTGAGAGTA  TTAGGAAACA  TGAGCAGCAT  ATGGCTTTTG  ATCAGTTTTT  CAGTGGCAGC              1531

ATCCAATGAA  CAAGATCCTA  CAAGCTGTGC  AGGCAAAACC  TAGCAGGAAA  AAAAAACAAC              1591

GCATAAAGAA  AAATGGCCGG  GCCAGGTCAT  TGGCTGGGAA  GTCTCAGCCA  TGCACGGACT              1651

CGTTTCCAGA  GGTAATTATG  AGCGCCTACC  AGCCAGGCCA  CCCAGCCGTG  GGAGGAAGGG              1711

GGCGTGGCAA  GGGGTGGGCA  CATTGGTGTC  TGTGCGAAAG  GAAAATTGAC  CCGGAAGTTC              1771

CTGTAATAAA  TGTCACAATA  AACGAATGA   ATGAAAAAAA  AAAAAAAAA   A                       1822
```

( 2 ) INFORMATION FOR SEQ ID NO:17:

( i ) SEQUENCE CHARACTERISTICS:
        ( A ) LENGTH: 431 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

| Met 1   | His      | Val      | Arg      | Ser 5    | Leu      | Arg      | Ala      | Ala      | Pro 10   | His      | Ser      | Phe      | Val 15   | Ala      |
|---------|----------|----------|----------|----------|----------|----------|----------|----------|----------|----------|----------|----------|----------|----------|
| Leu     | Trp      | Ala      | Pro 20   | Leu      | Phe      | Leu      | Leu      | Arg 25   | Ser      | Ala      | Leu      | Ala 30   | Asp      | Phe Ser  |
| Leu     | Asp      | Asn 35   | Glu      | Val      | His      | Ser      | Ser 40   | Phe      | Ile      | His      | Arg      | Arg 45   | Leu      | Arg Ser  |
| Gln     | Glu 50   | Arg      | Arg      | Glu      | Met      | Gln 55   | Arg      | Glu      | Ile      | Leu      | Ser 60   | Ile      | Leu      | Gly Leu  |
| Pro 65  | His      | Arg      | Pro      | Arg 70   | Pro      | His      | Leu      | Gln      | Gly 75   | Lys      | His      | Asn      | Ser      | Ala Pro 80 |
| Met     | Phe      | Met      | Leu      | Asp 85   | Leu      | Tyr      | Asn      | Ala      | Met 90   | Ala      | Val      | Glu      | Glu 95   | Gly Gly  |
| Gly     | Pro      | Gly      | Gly 100  | Gln      | Gly      | Phe      | Ser      | Tyr 105  | Pro      | Tyr      | Lys      | Ala      | Val 110  | Phe Ser  |
| Thr     | Gln      | Gly 115  | Pro      | Pro      | Leu      | Ala      | Ser 120  | Leu      | Gln      | Asp      | Ser      | His 125  | Phe      | Leu Thr  |
| Asp     | Ala 130  | Asp      | Met      | Val      | Met      | Ser 135  | Phe      | Val      | Asn      | Leu      | Val 140  | Glu      | His      | Asp Lys  |
| Glu 145 | Phe      | Phe      | His      | Pro      | Arg 150  | Tyr      | His      | His      | Arg      | Glu 155  | Phe      | Arg      | Phe      | Asp Leu 160 |
| Ser     | Lys      | Ile      | Pro      | Glu 165  | Gly      | Glu      | Ala      | Val      | Thr 170  | Ala      | Ala      | Glu      | Phe      | Arg 175  Ile |
| Tyr     | Lys      | Asp      | Tyr 180  | Ile      | Arg      | Glu      | Arg      | Phe 185  | Asp      | Asn      | Glu      | Thr      | Phe 190  | Arg Ile  |
| Ser     | Val      | Tyr 195  | Gln      | Val      | Leu      | Gln      | Glu 200  | His      | Leu      | Gly      | Arg      | Glu 205  | Ser      | Asp Leu  |
| Phe     | Leu 210  | Leu      | Asp      | Ser      | Arg      | Thr 215  | Leu      | Trp      | Ala      | Ser      | Glu 220  | Glu      | Gly      | Trp Leu  |
| Val 225 | Phe      | Asp      | Ile      | Thr      | Ala 230  | Thr      | Ser      | Asn      | His      | Trp 235  | Val      | Val      | Asn      | Pro Arg 240 |
| His     | Asn      | Leu      | Gly      | Leu 245  | Gln      | Leu      | Ser      | Val      | Glu 250  | Thr      | Leu      | Asp      | Gly      | Gln Ser 255 |
| Ile     | Asn      | Pro      | Lys 260  | Leu      | Ala      | Gly      | Leu      | Ile 265  | Gly      | Arg      | His      | Gly      | Pro 270  | Gln Asn  |
| Lys     | Gln      | Pro 275  | Phe      | Met      | Val      | Ala      | Phe 280  | Phe      | Lys      | Ala      | Thr      | Glu 285  | Val      | His Phe  |
| Arg     | Ser 290  | Ile      | Arg      | Ser      | Thr      | Gly 295  | Ser      | Lys      | Gln      | Arg      | Ser 300  | Gln      | Asn      | Arg Ser  |
| Lys 305 | Thr      | Pro      | Lys      | Asn      | Gln 310  | Glu      | Ala      | Leu      | Arg      | Met 315  | Ala      | Asn      | Val      | Ala Glu 320 |
| Asn     | Ser      | Ser      | Ser      | Asp 325  | Gln      | Arg      | Gln      | Ala      | Cys 330  | Lys      | Lys      | His      | Glu      | Leu Tyr 335 |
| Val     | Ser      | Phe      | Arg 340  | Asp      | Leu      | Gly      | Trp      | Gln 345  | Asp      | Trp      | Ile      | Ile      | Ala 350  | Pro Glu  |
| Gly     | Tyr      | Ala 355  | Ala      | Tyr      | Tyr      | Cys      | Glu 360  | Gly      | Glu      | Cys      | Ala      | Phe 365  | Pro      | Leu Asn  |
| Ser     | Tyr 370  | Met      | Asn      | Ala      | Thr      | Asn 375  | His      | Ala      | Ile      | Val      | Gln 380  | Thr      | Leu      | Val His  |
| Phe 385 | Ile      | Asn      | Pro      | Glu      | Thr 390  | Val      | Pro      | Lys      | Pro      | Cys 395  | Cys      | Ala      | Pro      | Thr Gln 400 |
| Leu     | Asn      | Ala      | Ile      | Ser 405  | Val      | Leu      | Tyr      | Phe      | Asp 410  | Asp      | Ser      | Ser      | Asn      | Val Ile 415 |

```
Leu Lys Lys Tyr Arg Asn Met Val Val Arg Ala Cys Gly Cys His
        420                 425                 430
```

( 2 ) INFORMATION FOR SEQ ID NO:18:

( i ) SEQUENCE CHARACTERISTICS:
        ( A ) LENGTH: 1873 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 104..1393
        ( D ) OTHER INFORMATION: /product="MOP1 (CDNA)"

( x i ) SEQUENCE DESCRIPTION: SEQ ID NO:18:

```
CTGCAGCAAG TGACCTCGGG TCGTGGACCG CTGCCCTGCC CCCTCCGCTG CCACCTGGGG          60

CGGCGCGGGC CCGGTGCCCC GGATCGCGCG TAGAGCCGGC GCG ATG CAC GTG CGC          115
                                              Met His Val Arg
                                               1

TCG CTG CGC GCT GCG GCG CCA CAC AGC TTC GTG GCG CTC TGG GCG CCT          163
Ser Leu Arg Ala Ala Ala Pro His Ser Phe Val Ala Leu Trp Ala Pro
  5              10                  15                  20

CTG TTC TTG CTG CGC TCC GCC CTG GCC GAT TTC AGC CTG GAC AAC GAG          211
Leu Phe Leu Leu Arg Ser Ala Leu Ala Asp Phe Ser Leu Asp Asn Glu
                 25                  30                  35

GTG CAC TCC AGC TTC ATC CAC CGG CGC CTC CGC AGC CAG GAG CGG CGG          259
Val His Ser Ser Phe Ile His Arg Arg Leu Arg Ser Gln Glu Arg Arg
             40                  45                  50

GAG ATG CAG CGG GAG ATC CTG TCC ATC TTA GGG TTG CCC CAT CGC CCG          307
Glu Met Gln Arg Glu Ile Leu Ser Ile Leu Gly Leu Pro His Arg Pro
         55                  60                  65

CGC CCG CAC CTC CAG GGA AAG CAT AAT TCG GCG CCC ATG TTC ATG TTG          355
Arg Pro His Leu Gln Gly Lys His Asn Ser Ala Pro Met Phe Met Leu
     70                  75                  80

GAC CTG TAC AAC GCC ATG GCG GTG GAG GAG AGC GGG CCG GAC GGA CAG          403
Asp Leu Tyr Asn Ala Met Ala Val Glu Glu Ser Gly Pro Asp Gly Gln
 85                  90                  95                 100

GGC TTC TCC TAC CCC TAC AAG GCC GTC TTC AGT ACC CAG GGC CCC CCT          451
Gly Phe Ser Tyr Pro Tyr Lys Ala Val Phe Ser Thr Gln Gly Pro Pro
                105                 110                 115

TTA GCC AGC CTG CAG GAC AGC CAT TTC CTC ACT GAC GCC GAC ATG GTC          499
Leu Ala Ser Leu Gln Asp Ser His Phe Leu Thr Asp Ala Asp Met Val
            120                 125                 130

ATG AGC TTC GTC AAC CTA GTG GAA CAT GAC AAA GAA TTC TTC CAC CCT          547
Met Ser Phe Val Asn Leu Val Glu His Asp Lys Glu Phe Phe His Pro
        135                 140                 145

CGA TAC CAC CAT CGG GAG TTC CGG TTT GAT CTT TCC AAG ATC CCC GAG          595
Arg Tyr His His Arg Glu Phe Arg Phe Asp Leu Ser Lys Ile Pro Glu
    150                 155                 160

GGC GAA CGG GTG ACC GCA GCC GAA TTC AGG ATC TAT AAG GAC TAC ATC          643
Gly Glu Arg Val Thr Ala Ala Glu Phe Arg Ile Tyr Lys Asp Tyr Ile
165                 170                 175                 180

CGG GAG CGA TTT GAC AAC GAG ACC TTC CAG ATC ACA GTC TAT CAG GTG          691
Arg Glu Arg Phe Asp Asn Glu Thr Phe Gln Ile Thr Val Tyr Gln Val
                185                 190                 195

CTC CAG GAG CAC TCA GGC AGG GAG TCG GAC CTC TTC TTG CTG GAC AGC          739
Leu Gln Glu His Ser Gly Arg Glu Ser Asp Leu Phe Leu Leu Asp Ser
            200                 205                 210

CGC ACC ATC TGG GCT TCT GAG GAG GGC TGG TTG GTG TTT GAT ATC ACA          787
```

```
            Arg Thr Ile Trp Ala Ser Glu Glu Gly Trp Leu Val Phe Asp Ile Thr
                    215             220                 225

GCC ACC AGC AAC CAC TGG GTG GTC AAC CCT CGG CAC AAC CTG GGC TTA            835
Ala Thr Ser Asn His Trp Val Val Asn Pro Arg His Asn Leu Gly Leu
        230             235                 240

CAG CTC TCT GTG GAG ACC CTG GAT GGG CAG AGC ATC AAC CCC AAG TTG            883
Gln Leu Ser Val Glu Thr Leu Asp Gly Gln Ser Ile Asn Pro Lys Leu
245             250                 255                 260

GCA GGC CTG ATT GGA CGG CAT GGA CCC CAG AAC AAG CAA CCC TTC ATG            931
Ala Gly Leu Ile Gly Arg His Gly Pro Gln Asn Lys Gln Pro Phe Met
                265                 270                 275

GTG GCC TTC TTC AAG GCC ACG GAA GTC CAT CTC CGT AGT ATC CGG TCC            979
Val Ala Phe Phe Lys Ala Thr Glu Val His Leu Arg Ser Ile Arg Ser
            280             285                 290

ACG GGG GGC AAG CAG CGC AGC CAG AAT CGC TCC AAG ACG CCA AAG AAC           1027
Thr Gly Gly Lys Gln Arg Ser Gln Asn Arg Ser Lys Thr Pro Lys Asn
            295             300                 305

CAA GAG GCC CTG AGG ATG GCC AGT GTG GCA GAA AAC AGC AGC AGT GAC           1075
Gln Glu Ala Leu Arg Met Ala Ser Val Ala Glu Asn Ser Ser Ser Asp
        310             315                 320

CAG AGG CAG GCC TGC AAG AAA CAT GAG CTG TAC GTC AGC TTC CGA GAC           1123
Gln Arg Gln Ala Cys Lys Lys His Glu Leu Tyr Val Ser Phe Arg Asp
325             330                 335                 340

CTT GGC TGG CAG GAC TGG ATC ATT GCA CCT GAA GGC TAT GCT GCC TAC           1171
Leu Gly Trp Gln Asp Trp Ile Ile Ala Pro Glu Gly Tyr Ala Ala Tyr
                345                 350                 355

TAC TGT GAG GGA GAG TGC GCC TTC CCT CTG AAC TCC TAC ATG AAC GCC           1219
Tyr Cys Glu Gly Glu Cys Ala Phe Pro Leu Asn Ser Tyr Met Asn Ala
            360                 365                 370

ACC AAC CAC GCC ATC GTC CAG ACA CTG GTT CAC TTC ATC AAC CCA GAC           1267
Thr Asn His Ala Ile Val Gln Thr Leu Val His Phe Ile Asn Pro Asp
            375                 380                 385

ACA GTA CCC AAG CCC TGC TGT GCG CCC ACC CAG CTC AAC GCC ATC TCT           1315
Thr Val Pro Lys Pro Cys Cys Ala Pro Thr Gln Leu Asn Ala Ile Ser
    390                 395                 400

GTC CTC TAC TTC GAC GAC AGC TCT AAT GTC ATC CTG AAG AAG TAC AGA           1363
Val Leu Tyr Phe Asp Asp Ser Ser Asn Val Ile Leu Lys Lys Tyr Arg
405                 410                 415                 420

AAC ATG GTG GTC CGG GCC TGT GGC TGC CAC TAGCTCTTCC TGAGACCCTG             1413
Asn Met Val Val Arg Ala Cys Gly Cys His
                425                 430

ACCTTTGCGG GGCCACACCT TTCCAAATCT TCGATGTCTC ACCATCTAAG TCTCTCACTG         1473

CCCACCTTGG CGAGGAGAAC AGACCAACCT CTCCTGAGCC TTCCCTCACC TCCCAACCGG         1533

AAGCATGTAA GGGTTCCAGA AACCTGAGCG TGCAGCAGCT GATGAGCGCC CTTTCCTTCT         1593

GGCACGTGAC GGACAAGATC CTACCAGCTA CCACAGCAAA CGCCTAAGAG CAGGAAAAAT         1653

GTCTGCCAGG AAAGTGTCCA GTGTCCACAT GGCCCCTGGC GCTCTGAGTC TTTGAGGAGT         1713

AATCGCAAGC CTCGTTCAGC TGCAGCAGAA GGAAGGGCTT AGCCAGGGTG GGCGCTGGCG         1773

TCTGTGTTGA AGGGAAACCA AGCAGAAGCC ACTGTAATGA TATGTCACAA TAAAACCCAT         1833

GAATGAAAAA AAAAAAAAA AAAAAAAAA AAAAGAATTC                                 1873
```

( 2 ) INFORMATION FOR SEQ ID NO:19:

( i ) SEQUENCE CHARACTERISTICS:
        ( A ) LENGTH: 430 amino acids
        ( B ) TYPE: amino acid
        ( D ) TOPOLOGY: linear ( i i ) MOLECULE TYPE: protein (xi) SEQUENCE DESCRIPTION: SEQ ID NO:19:

```
Met His Val Arg Ser Leu Arg Ala Ala Ala Pro His Ser Phe Val Ala
  1               5                  10                  15
Leu Trp Ala Pro Leu Phe Leu Leu Arg Ser Ala Leu Ala Asp Phe Ser
                 20                  25                  30
Leu Asp Asn Glu Val His Ser Ser Phe Ile His Arg Arg Leu Arg Ser
             35                  40                  45
Gln Glu Arg Arg Glu Met Gln Arg Glu Ile Leu Ser Ile Leu Gly Leu
 50                      55                  60
Pro His Arg Pro Arg Pro His Leu Gln Gly Lys His Asn Ser Ala Pro
 65                  70                  75                  80
Met Phe Met Leu Asp Leu Tyr Asn Ala Met Ala Val Glu Glu Ser Gly
                 85                  90                  95
Pro Asp Gly Gln Gly Phe Ser Tyr Pro Tyr Lys Ala Val Phe Ser Thr
                100                 105                 110
Gln Gly Pro Pro Leu Ala Ser Leu Gln Asp Ser His Phe Leu Thr Asp
        115                 120                 125
Ala Asp Met Val Met Ser Phe Val Asn Leu Val Glu His Asp Lys Glu
130                 135                 140
Phe Phe His Pro Arg Tyr His His Arg Glu Phe Arg Phe Asp Leu Ser
145                 150                 155                 160
Lys Ile Pro Glu Gly Glu Arg Val Thr Ala Ala Glu Phe Arg Ile Tyr
                165                 170                 175
Lys Asp Tyr Ile Arg Glu Arg Phe Asp Asn Glu Thr Phe Gln Ile Thr
            180                 185                 190
Val Tyr Gln Val Leu Gln Glu His Ser Gly Arg Glu Ser Asp Leu Phe
        195                 200                 205
Leu Leu Asp Ser Arg Thr Ile Trp Ala Ser Glu Glu Gly Trp Leu Val
210                 215                 220
Phe Asp Ile Thr Ala Thr Ser Asn His Trp Val Val Asn Pro Arg His
225                 230                 235                 240
Asn Leu Gly Leu Gln Leu Ser Val Glu Thr Leu Asp Gly Gln Ser Ile
                245                 250                 255
Asn Pro Lys Leu Ala Gly Leu Ile Gly Arg His Gly Pro Gln Asn Lys
            260                 265                 270
Gln Pro Phe Met Val Ala Phe Phe Lys Ala Thr Glu Val His Leu Arg
        275                 280                 285
Ser Ile Arg Ser Thr Gly Gly Lys Gln Arg Ser Gln Asn Arg Ser Lys
290                 295                 300
Thr Pro Lys Asn Gln Glu Ala Leu Arg Met Ala Ser Val Ala Glu Asn
305                 310                 315                 320
Ser Ser Ser Asp Gln Arg Gln Ala Cys Lys Lys His Glu Leu Tyr Val
                325                 330                 335
Ser Phe Arg Asp Leu Gly Trp Gln Asp Trp Ile Ile Ala Pro Glu Gly
            340                 345                 350
Tyr Ala Ala Tyr Tyr Cys Glu Gly Glu Cys Ala Phe Pro Leu Asn Ser
        355                 360                 365
Tyr Met Asn Ala Thr Asn His Ala Ile Val Gln Thr Leu Val His Phe
370                 375                 380
Ile Asn Pro Asp Thr Val Pro Lys Pro Cys Cys Ala Pro Thr Gln Leu
385                 390                 395                 400
Asn Ala Ile Ser Val Leu Tyr Phe Asp Asp Ser Ser Asn Val Ile Leu
                405                 410                 415
```

Lys Lys Tyr Arg Asn Met Val Val Arg Ala Cys Gly Cys His
             420                 425                 430

( 2 ) INFORMATION FOR SEQ ID NO:20:

( i ) SEQUENCE CHARACTERISTICS:
        ( A ) LENGTH: 1723 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 490..1695

( x i ) SEQUENCE DESCRIPTION: SEQ ID NO:20:

```
GGCGCCGGCA GAGCAGGAGT GGCTGGAGGA GCTGTGGTTG GAGCAGGAGG TGGCACGGCA        60

GGGCTGGAGG GCTCCCTATG AGTGGCGGAG ACGGCCCAGG AGGCGCTGGA GCAACAGCTC       120

CCACACCGCA CCAAGCGGTG GCTGCAGGAG CTCGCCCATC GCCCCTGCGC TGCTCGGACC       180

GCGGCCACAG CCGGACTGGC GGGTACGGCG GCGACAGAGG CATTGGCCGA GAGTCCCAGT       240

CCGCAGAGTA GCCCCGGCCT CGAGGCGGTG GCGTCCCGGT CCTCTCCGTC CAGGAGCCAG       300

GACAGGTGTC GCGCGGCGGG GCTCCAGGGA CCGCGCCTGA GGCCGGCTGC CCGCCCGTCC       360

CGCCCCGCCC CGCCGCCCGC CGCCCGCCGA GCCCAGCCTC CTTGCCGTCG GGGCGTCCCC       420

AGGCCCTGGG TCGGCCGCGG AGCCGATGCG CGCCCGCTGA GCGCCCAGC  TGAGCGCCCC       480

CGGCCTGCC ATG ACC GCG CTC CCC GGC CCG CTC TGG CTC CTG GGC CTG           528
           Met Thr Ala Leu Pro Gly Pro Leu Trp Leu Leu Gly Leu
            1               5                   10
```

| | | | | | | | | | | | | | | | |
|---|---|---|---|---|---|---|---|---|---|---|---|---|---|---|---|
| GCG | CTA | TGC | GCG | CTG | GGC | GGG | GGC | GGC | CCC | GGC | CTG | CGA | CCC | CCG | CCC | 576 |
| Ala | Leu | Cys | Ala | Leu | Gly | Gly | Gly | Gly | Pro | Gly | Leu | Arg | Pro | Pro | Pro | |
| | 15 | | | | 20 | | | | | 25 | | | | | | |

| GGC | TGT | CCC | CAG | CGA | CGT | CTG | GGC | GCG | CGC | GAG | CGC | GGG | ACG | TG | CAG | 624 |
|---|---|---|---|---|---|---|---|---|---|---|---|---|---|---|---|---|
| Gly | Cys | Pro | Gln | Arg | Arg | Leu | Gly | Ala | Arg | Glu | Arg | Arg | Asp | Val | Gln | |
| 30 | | | | 35 | | | | | 40 | | | | | | 45 | |

| CGC | GAG | ATC | CTG | GCG | GTG | CTC | GGG | CTG | CCT | GGG | CGG | CCC | CGG | CCC | CGC | 672 |
|---|---|---|---|---|---|---|---|---|---|---|---|---|---|---|---|---|
| Arg | Glu | Ile | Leu | Ala | Val | Leu | Gly | Leu | Pro | Gly | Arg | Pro | Arg | Pro | Arg | |
| | | | | 50 | | | | | 55 | | | | | 60 | | |

| GCG | CCA | CCC | GCC | GCC | TCC | CGG | CTG | CCC | GCG | TCC | GCG | CCG | CTC | TTC | ATG | 720 |
|---|---|---|---|---|---|---|---|---|---|---|---|---|---|---|---|---|
| Ala | Pro | Pro | Ala | Ala | Ser | Arg | Leu | Pro | Ala | Ser | Ala | Pro | Leu | Phe | Met | |
| | | | | 65 | | | | | 70 | | | | | 75 | | |

| CTG | GAC | CTG | TAC | CAC | GCC | ATG | GCC | GGC | GAC | GAC | GAC | GAG | GAC | GGC | GCG | 768 |
|---|---|---|---|---|---|---|---|---|---|---|---|---|---|---|---|---|
| Leu | Asp | Leu | Tyr | His | Ala | Met | Ala | Gly | Asp | Asp | Asp | Glu | Asp | Gly | Ala | |
| | | | 80 | | | | 85 | | | | | 90 | | | | |

| CCC | GCG | GAG | CGG | CGC | CTG | GGC | CGC | GCC | GAC | CTG | GTC | ATG | AGC | TTC | GTT | 816 |
|---|---|---|---|---|---|---|---|---|---|---|---|---|---|---|---|---|
| Pro | Ala | Glu | Arg | Arg | Leu | Gly | Arg | Ala | Asp | Leu | Val | Met | Ser | Phe | Val | |
| | 95 | | | | 100 | | | | | 105 | | | | | | |

| AAC | ATG | GTG | GAG | CGA | GAC | CGT | GCC | CTG | GGC | CAC | CAG | GAG | CCC | CAT | TGG | 864 |
|---|---|---|---|---|---|---|---|---|---|---|---|---|---|---|---|---|
| Asn | Met | Val | Glu | Arg | Asp | Arg | Ala | Leu | Gly | His | Gln | Glu | Pro | His | Trp | |
| 110 | | | | 115 | | | | | 120 | | | | | | 125 | |

| AAG | GAG | TTC | CGC | TTT | GAC | CTG | ACC | CAG | ATC | CCG | GCT | GGG | GAG | GCG | GTC | 912 |
|---|---|---|---|---|---|---|---|---|---|---|---|---|---|---|---|---|
| Lys | Glu | Phe | Arg | Phe | Asp | Leu | Thr | Gln | Ile | Pro | Ala | Gly | Glu | Ala | Val | |
| | | | 130 | | | | 135 | | | | | 140 | | | | |

| ACA | GCT | GCG | GAG | TTC | CGG | ATT | TAC | AAG | GTG | CCC | AGC | ATC | CAC | CTG | CTC | 960 |
|---|---|---|---|---|---|---|---|---|---|---|---|---|---|---|---|---|
| Thr | Ala | Ala | Glu | Phe | Arg | Ile | Tyr | Lys | Val | Pro | Ser | Ile | His | Leu | Leu | |
| | | | 145 | | | | 150 | | | | | 155 | | | | |

| AAC | AGG | ACC | CTC | CAC | GTC | AGC | ATG | TTC | CAG | GTG | GTC | CAG | GAG | CAG | TCC | 1008 |
|---|---|---|---|---|---|---|---|---|---|---|---|---|---|---|---|---|
| Asn | Arg | Thr | Leu | His | Val | Ser | Met | Phe | Gln | Val | Val | Gln | Glu | Gln | Ser | |
| | 160 | | | | 165 | | | | | 170 | | | | | | |

```
AAC  AGG  GAG  TCT  GAC  TTG  TTC  TTT  TTG  GAT  CTT  CAG  ACG  CTC  CGA  GCT      1056
Asn  Arg  Glu  Ser  Asp  Leu  Phe  Phe  Leu  Asp  Leu  Gln  Thr  Leu  Arg  Ala
     175                 180                      185

GGA  GAC  GAG  GGC  TGG  CTG  GTG  CTG  GAT  GTC  ACA  GCA  GCC  AGT  GAC  TGC      1104
Gly  Asp  Glu  Gly  Trp  Leu  Val  Leu  Asp  Val  Thr  Ala  Ala  Ser  Asp  Cys
190                      195                      200                      205

TGG  TTG  CTG  AAG  CGT  CAC  AAG  GAC  CTG  GGA  CTC  CGC  CTC  TAT  GTG  GAG      1152
Trp  Leu  Leu  Lys  Arg  His  Lys  Asp  Leu  Gly  Leu  Arg  Leu  Tyr  Val  Glu
                    210                      215                      220

ACT  GAG  GAC  GGG  CAC  AGC  GTG  GAT  CCT  GGC  CTG  GCC  GGC  CTG  CTG  GGT      1200
Thr  Glu  Asp  Gly  His  Ser  Val  Asp  Pro  Gly  Leu  Ala  Gly  Leu  Leu  Gly
               225                      230                      235

CAA  CGG  GCC  CCA  CGC  TCC  CAA  CAG  CCT  TTC  GTG  GTC  ACT  TTC  TTC  AGG      1248
Gln  Arg  Ala  Pro  Arg  Ser  Gln  Gln  Pro  Phe  Val  Val  Thr  Phe  Phe  Arg
          240                      245                      250

GCC  AGT  CCG  AGT  CCC  ATC  CGC  ACC  CCT  CGG  GCA  GTG  AGG  CCA  CTG  AGG      1296
Ala  Ser  Pro  Ser  Pro  Ile  Arg  Thr  Pro  Arg  Ala  Val  Arg  Pro  Leu  Arg
     255                      260                      265

AGG  AGG  CAG  CCG  AAG  AAA  AGC  AAC  GAG  CTG  CCG  CAG  GCC  AAC  CGA  CTC      1344
Arg  Arg  Gln  Pro  Lys  Lys  Ser  Asn  Glu  Leu  Pro  Gln  Ala  Asn  Arg  Leu
270                      275                      280                      285

CCA  GGG  ATC  TTT  GAT  GAC  GTC  CAC  GGC  TCC  CAC  GGC  CGG  CAG  GTC  TGC      1392
Pro  Gly  Ile  Phe  Asp  Asp  Val  His  Gly  Ser  His  Gly  Arg  Gln  Val  Cys
               290                      295                      300

CGT  CGG  CAC  GAG  CTC  TAC  GTC  AGC  TTC  CAG  GAC  CTC  GGC  TGG  CTG  GAC      1440
Arg  Arg  His  Glu  Leu  Tyr  Val  Ser  Phe  Gln  Asp  Leu  Gly  Trp  Leu  Asp
          305                      310                      315

TGG  GTC  ATC  GCT  CCC  CAA  GGC  TAC  TCG  GCC  TAT  TAC  TGT  GAG  GGG  GAG      1488
Trp  Val  Ile  Ala  Pro  Gln  Gly  Tyr  Ser  Ala  Tyr  Tyr  Cys  Glu  Gly  Glu
     320                      325                      330

TGC  TCC  TTC  CCA  CTG  GAC  TCC  TGC  ATG  AAT  GCC  ACC  AAC  CAC  GCC  ATC      1536
Cys  Ser  Phe  Pro  Leu  Asp  Ser  Cys  Met  Asn  Ala  Thr  Asn  His  Ala  Ile
335                      340                      345

CTG  CAG  TCC  CTG  GTG  CAC  CTG  ATG  AAG  CCA  AAC  GCA  GTC  CCC  AAG  GCG      1584
Leu  Gln  Ser  Leu  Val  His  Leu  Met  Lys  Pro  Asn  Ala  Val  Pro  Lys  Ala
350                      355                      360                      365

TGC  TGT  GCA  CCC  ACC  AAG  CTG  AGC  GCC  ACC  TCT  GTG  CTC  TAC  TAT  GAC      1632
Cys  Cys  Ala  Pro  Thr  Lys  Leu  Ser  Ala  Thr  Ser  Val  Leu  Tyr  Tyr  Asp
               370                      375                      380

AGC  AGC  AAC  AAC  GTC  ATC  CTG  CGC  AAA  CAC  CGC  AAC  ATG  GTG  GTC  AAG      1680
Ser  Ser  Asn  Asn  Val  Ile  Leu  Arg  Lys  His  Arg  Asn  Met  Val  Val  Lys
               385                      390                      395

GCC  TGC  GGC  TGC  CAC  TGAGTCAGCC  CGCCCAGCCC  TACTGCAG                           1723
Ala  Cys  Gly  Cys  His
               400
```

( 2 ) INFORMATION FOR SEQ ID NO:21:

( i ) SEQUENCE CHARACTERISTICS:
        ( A ) LENGTH: 402 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

```
Met  Thr  Ala  Leu  Pro  Gly  Pro  Leu  Trp  Leu  Leu  Gly  Leu  Ala  Leu  Cys
1                   5                   10                      15

Ala  Leu  Gly  Gly  Gly  Gly  Pro  Gly  Leu  Arg  Pro  Pro  Pro  Gly  Cys  Pro
               20                      25                      30

Gln  Arg  Arg  Leu  Gly  Ala  Arg  Glu  Arg  Arg  Asp  Val  Gln  Arg  Glu  Ile
```

|     |     |     | 35  |     |     |     | 40  |     |     |     | 45  |     |     |     |
|-----|-----|-----|-----|-----|-----|-----|-----|-----|-----|-----|-----|-----|-----|-----|
| Leu | Ala | Val | Leu | Gly | Leu | Pro | Gly | Arg | Pro | Arg | Pro | Arg | Ala | Pro | Pro |
|     | 50  |     |     |     | 55  |     |     |     | 60  |     |     |     |     |     |
| Ala | Ala | Ser | Arg | Leu | Pro | Ala | Ser | Ala | Pro | Leu | Phe | Met | Leu | Asp | Leu |
| 65  |     |     |     | 70  |     |     |     | 75  |     |     |     |     |     | 80  |
| Tyr | His | Ala | Met | Ala | Gly | Asp | Asp | Asp | Glu | Asp | Gly | Ala | Pro | Ala | Glu |
|     |     |     |     | 85  |     |     |     |     | 90  |     |     |     |     | 95  |
| Arg | Arg | Leu | Gly | Arg | Ala | Asp | Leu | Val | Met | Ser | Phe | Val | Asn | Met | Val |
|     |     |     | 100 |     |     |     | 105 |     |     |     |     | 110 |     |     |
| Glu | Arg | Asp | Arg | Ala | Leu | Gly | His | Gln | Glu | Pro | His | Trp | Lys | Glu | Phe |
|     |     | 115 |     |     |     |     | 120 |     |     |     |     | 125 |     |     |
| Arg | Phe | Asp | Leu | Thr | Gln | Ile | Pro | Ala | Gly | Glu | Ala | Val | Thr | Ala | Ala |
|     | 130 |     |     |     | 135 |     |     |     |     | 140 |     |     |     |     |
| Glu | Phe | Arg | Ile | Tyr | Lys | Val | Pro | Ser | Ile | His | Leu | Leu | Asn | Arg | Thr |
| 145 |     |     |     | 150 |     |     |     |     | 155 |     |     |     |     | 160 |
| Leu | His | Val | Ser | Met | Phe | Gln | Val | Val | Gln | Glu | Gln | Ser | Asn | Arg | Glu |
|     |     |     |     | 165 |     |     |     |     | 170 |     |     |     | 175 |     |
| Ser | Asp | Leu | Phe | Phe | Leu | Asp | Leu | Gln | Thr | Leu | Arg | Ala | Gly | Asp | Glu |
|     |     |     | 180 |     |     |     |     | 185 |     |     |     | 190 |     |     |
| Gly | Trp | Leu | Val | Leu | Asp | Val | Thr | Ala | Ala | Ser | Asp | Cys | Trp | Leu | Leu |
|     |     | 195 |     |     |     |     | 200 |     |     |     | 205 |     |     |     |
| Lys | Arg | His | Lys | Asp | Leu | Gly | Leu | Arg | Leu | Tyr | Val | Glu | Thr | Glu | Asp |
|     | 210 |     |     |     |     | 215 |     |     |     |     | 220 |     |     |     |
| Gly | His | Ser | Val | Asp | Pro | Gly | Leu | Ala | Gly | Leu | Leu | Gly | Gln | Arg | Ala |
| 225 |     |     |     |     | 230 |     |     |     | 235 |     |     |     |     | 240 |
| Pro | Arg | Ser | Gln | Gln | Pro | Phe | Val | Val | Thr | Phe | Phe | Arg | Ala | Ser | Pro |
|     |     |     |     | 245 |     |     |     |     | 250 |     |     |     |     | 255 |
| Ser | Pro | Ile | Arg | Thr | Pro | Arg | Ala | Val | Arg | Pro | Leu | Arg | Arg | Arg | Gln |
|     |     |     | 260 |     |     |     |     | 265 |     |     |     | 270 |     |     |
| Pro | Lys | Lys | Ser | Asn | Glu | Leu | Pro | Gln | Ala | Asn | Arg | Leu | Pro | Gly | Ile |
|     |     | 275 |     |     |     |     | 280 |     |     |     |     | 285 |     |     |
| Phe | Asp | Asp | Val | His | Gly | Ser | His | Gly | Arg | Gln | Val | Cys | Arg | Arg | His |
|     | 290 |     |     |     |     | 295 |     |     |     |     | 300 |     |     |     |
| Glu | Leu | Tyr | Val | Ser | Phe | Gln | Asp | Leu | Gly | Trp | Leu | Asp | Trp | Val | Ile |
| 305 |     |     |     |     | 310 |     |     |     |     | 315 |     |     |     |     | 320 |
| Ala | Pro | Gln | Gly | Tyr | Ser | Ala | Tyr | Tyr | Cys | Glu | Gly | Glu | Cys | Ser | Phe |
|     |     |     |     | 325 |     |     |     |     | 330 |     |     |     |     | 335 |
| Pro | Leu | Asp | Ser | Cys | Met | Asn | Ala | Thr | Asn | His | Ala | Ile | Leu | Gln | Ser |
|     |     |     | 340 |     |     |     |     | 345 |     |     |     |     | 350 |     |
| Leu | Val | His | Leu | Met | Lys | Pro | Asn | Ala | Val | Pro | Lys | Ala | Cys | Cys | Ala |
|     |     | 355 |     |     |     |     | 360 |     |     |     |     | 365 |     |     |
| Pro | Thr | Lys | Leu | Ser | Ala | Thr | Ser | Val | Leu | Tyr | Tyr | Asp | Ser | Ser | Asn |
|     | 370 |     |     |     |     | 375 |     |     |     |     | 380 |     |     |     |
| Asn | Val | Ile | Leu | Arg | Lys | His | Arg | Asn | Met | Val | Val | Lys | Ala | Cys | Gly |
| 385 |     |     |     |     | 390 |     |     |     |     | 395 |     |     |     |     | 400 |
| Cys | His |     |     |     |     |     |     |     |     |     |     |     |     |     |     |

( 2 ) INFORMATION FOR SEQ ID NO:22:

( i ) SEQUENCE CHARACTERISTICS:
        ( A ) LENGTH: 1926 base pairs
        ( B ) TYPE: nucleic acid
        ( C ) STRANDEDNESS: single
        ( D ) TOPOLOGY: linear ( i i ) MOLECULE TYPE: cDNA (ix) FEATURE:
    (A) NAME/KEY: CDS
    (B) LOCATION: 93..1289
    (D) OTHER INFORMATION: /product="MOP2 CDNA"

(xi) SEQUENCE DESCRIPTION: SEQ ID NO:22:

```
GCCAGGCACA GGTGCGCCGT CTGGTCCTCC CCGTCTGGCG TCAGCCGAGC CCGACCAGCT      60

ACCAGTGGAT GCGCGCCGGC TGAAAGTCCG AG ATG GCT ATG CGT CCC GGG CCA       113
                                   Met Ala Met Arg Pro Gly Pro
                                    1               5

CTC TGG CTA TTG GGC CTT GCT CTG TGC GCG CTG GGA GGC GGC CAC GGT       161
Leu Trp Leu Leu Gly Leu Ala Leu Cys Ala Leu Gly Gly Gly His Gly
         10                  15                  20

CCG CGT CCC CCG CAC ACC TGT CCC CAG CGT CGC CTG GGA GCG CGC GAG       209
Pro Arg Pro Pro His Thr Cys Pro Gln Arg Arg Leu Gly Ala Arg Glu
     25                  30                  35

CGC CGC GAC ATG CAG CGT GAA ATC CTG GCG GTG CTC GGG CTA CCG GGA       257
Arg Arg Asp Met Gln Arg Glu Ile Leu Ala Val Leu Gly Leu Pro Gly
 40                  45                  50                  55

CGG CCC CGA CCC CGT GCA CAA CCC GCG GCT GCC CGG CAG CCA GCG TCC       305
Arg Pro Arg Pro Arg Ala Gln Pro Ala Ala Ala Arg Gln Pro Ala Ser
                 60                  65                  70

GCG CCC CTC TTC ATG TTG GAC CTA TAC CAC GCC ATG ACC GAT GAC GAC       353
Ala Pro Leu Phe Met Leu Asp Leu Tyr His Ala Met Thr Asp Asp Asp
             75                  80                  85

GAC GGC GGG CCA CCA CAG GCT CAC TTA GGC CGT GCC GAC CTG GTC ATG       401
Asp Gly Gly Pro Pro Gln Ala His Leu Gly Arg Ala Asp Leu Val Met
         90                  95                 100

AGC TTC GTC AAC ATG GTG GAA CGC GAC CGT ACC CTG GGC TAC CAG GAG       449
Ser Phe Val Asn Met Val Glu Arg Asp Arg Thr Leu Gly Tyr Gln Glu
     105                 110                 115

CCA CAC TGG AAG GAA TTC CAC TTT GAC CTA ACC CAG ATC CCT GCT GGG       497
Pro His Trp Lys Glu Phe His Phe Asp Leu Thr Gln Ile Pro Ala Gly
 120                 125                 130                 135

GAG GCT GTC ACA GCT GCT GAG TTC CGG ATC TAC AAA GAA CCC AGC ACC       545
Glu Ala Val Thr Ala Ala Glu Phe Arg Ile Tyr Lys Glu Pro Ser Thr
                 140                 145                 150

CAC CCG CTC AAC ACA ACC CTC CAC ATC AGC ATG TTC GAA GTG GTC CAA       593
His Pro Leu Asn Thr Thr Leu His Ile Ser Met Phe Glu Val Val Gln
             155                 160                 165

GAG CAC TCC AAC AGG GAG TCT GAC TTG TTC TTT TTG GAT CTT CAG ACG       641
Glu His Ser Asn Arg Glu Ser Asp Leu Phe Phe Leu Asp Leu Gln Thr
         170                 175                 180

CTC CGA TCT GGG GAC GAG GGC TGG CTG GTG CTG GAC ATC ACA GCA GCC       689
Leu Arg Ser Gly Asp Glu Gly Trp Leu Val Leu Asp Ile Thr Ala Ala
     185                 190                 195

AGT GAC CGA TGG CTG CTG AAC CAT CAC AAG GAC CTG GGA CTC CGC CTC       737
Ser Asp Arg Trp Leu Leu Asn His His Lys Asp Leu Gly Leu Arg Leu
 200                 205                 210                 215

TAT GTG GAA ACC GCG GAT GGG CAC AGC ATG GAT CCT GGC CTG GCT GGT       785
Tyr Val Glu Thr Ala Asp Gly His Ser Met Asp Pro Gly Leu Ala Gly
                 220                 225                 230

CTG CTT GGA CGA CAA GCA CCA CGC TCC AGA CAG CCT TTC ATG GTA ACC       833
Leu Leu Gly Arg Gln Ala Pro Arg Ser Arg Gln Pro Phe Met Val Thr
             235                 240                 245

TTC TTC AGG GCC AGC CAG AGT CCT GTG CGG GCC CCT CGG GCA GCG AGA       881
Phe Phe Arg Ala Ser Gln Ser Pro Val Arg Ala Pro Arg Ala Ala Arg
         250                 255                 260

CCA CTG AAG AGG AGG CAG CCA AAG AAA ACG AAC GAG CTT CCG CAC CCC       929
Pro Leu Lys Arg Arg Gln Pro Lys Lys Thr Asn Glu Leu Pro His Pro
```

| | | | | | | | | | | | | | | | | |
|---|---|---|---|---|---|---|---|---|---|---|---|---|---|---|---|---|
| | | | 265 | | | | 270 | | | | | 275 | | | | |
| AAC | AAA | CTC | CCA | GGG | ATC | TTT | GAT | GAT | GGC | CAC | GGT | TCC | CGC | GGC | AGA | 977 |
| Asn | Lys | Leu | Pro | Gly | Ile | Phe | Asp | Asp | Gly | His | Gly | Ser | Arg | Gly | Arg | |
| 280 | | | | 285 | | | | | 290 | | | | | | 295 | |
| GAG | GTT | TGC | CGC | AGG | CAT | GAG | CTC | TAC | GTC | AGC | TTC | CGT | GAC | CTT | GGC | 1025 |
| Glu | Val | Cys | Arg | Arg | His | Glu | Leu | Tyr | Val | Ser | Phe | Arg | Asp | Leu | Gly | |
| | | | | 300 | | | | | 305 | | | | | 310 | | |
| TGG | CTG | GAC | TGG | GTC | ATC | GCC | CCC | CAG | GGC | TAC | TCT | GCC | TAT | TAC | TGT | 1073 |
| Trp | Leu | Asp | Trp | Val | Ile | Ala | Pro | Gln | Gly | Tyr | Ser | Ala | Tyr | Tyr | Cys | |
| | | | | 315 | | | | | 320 | | | | 325 | | | |
| GAG | GGG | GAG | TGT | GCT | TTC | CCA | CTG | GAC | TCC | TGT | ATG | AAC | GCC | ACC | AAC | 1121 |
| Glu | Gly | Glu | Cys | Ala | Phe | Pro | Leu | Asp | Ser | Cys | Met | Asn | Ala | Thr | Asn | |
| | | 330 | | | | | 335 | | | | | 340 | | | | |
| CAT | GCC | ATC | TTG | CAG | TCT | CTG | GTG | CAC | CTG | ATG | AAG | CCA | GAT | GTT | GTC | 1169 |
| His | Ala | Ile | Leu | Gln | Ser | Leu | Val | His | Leu | Met | Lys | Pro | Asp | Val | Val | |
| | | 345 | | | | | 350 | | | | | 355 | | | | |
| CCC | AAG | GCA | TGC | TGT | GCA | CCC | ACC | AAA | CTG | AGT | GCC | ACC | TCT | GTG | CTG | 1217 |
| Pro | Lys | Ala | Cys | Cys | Ala | Pro | Thr | Lys | Leu | Ser | Ala | Thr | Ser | Val | Leu | |
| 360 | | | | | 365 | | | | | 370 | | | | | 375 | |
| TAC | TAT | GAC | AGC | AGC | AAC | AAT | GTC | ATC | CTG | CGT | AAA | CAC | CGT | AAC | ATG | 1265 |
| Tyr | Tyr | Asp | Ser | Ser | Asn | Asn | Val | Ile | Leu | Arg | Lys | His | Arg | Asn | Met | |
| | | | | 380 | | | | | | 385 | | | | | 390 | |
| GTG | GTC | AAG | GCC | TGT | GGC | TGC | CAC | TGAGGCCCCG | | | CCCAGCATCC | | TGCTTCTACT | | | 1319 |
| Val | Val | Lys | Ala | Cys | Gly | Cys | His | | | | | | | | | |
| | | | | 395 | | | | | | | | | | | | |

```
ACCTTACCAT  CTGGCCGGGC  CCCTCTCCAG  AGGCAGAAAC  CCTTCTATGT  TATCATAGCT        1379

CAGACAGGGG  CAATGGGAGG  CCCTTCACTT  CCCCTGGCCA  CTTCCTGCTA  AAATTCTGGT        1439

CTTTCCCAGT  TCCTCTGTCC  TTCATGGGGT  TTCGGGGCTA  TCACCCCGCC  CTCTCCATCC        1499

TCCTACCCCA  AGCATAGACT  GAATGCACAC  AGCATCCCAG  AGCTATGCTA  ACTGAGAGGT        1559

CTGGGGTCAG  CACTGAAGGC  CCACATGAGG  AAGACTGATC  CTTGGCCATC  CTCAGCCCAC        1619

AATGGCAAAT  TCTGGATGGT  CTAAGAAGGC  CCTGGAATTC  TAAACTAGAT  GATCTGGGCT        1679

CTCTGCACCA  TTCATTGTGG  CAGTTGGGAC  ATTTTTAGGT  ATAACAGACA  CATACACTTA        1739

GATCAATGCA  TCGCTGTACT  CCTTGAAATC  AGAGCTAGCT  TGTTAGAAAA  AGAATCAGAG        1799

CCAGGTATAG  CGGTGCATGT  CATTAATCCC  AGCGCTAAAG  AGACAGAGAC  AGGAGAATCT        1859

CTGTGAGTTC  AAGGCCACAT  AGAAAGAGCC  TGTCTCGGGA  GCAGGAAAAA  AAAAAAAAAC        1919

GGAATTC                                                                      1926
```

( 2 ) INFORMATION FOR SEQ ID NO:23:

( i ) SEQUENCE CHARACTERISTICS:
        ( A ) LENGTH: 399 amino acids
        ( B ) TYPE: amino acid
        ( D ) TOPOLOGY: linear ( i i ) MOLECULE TYPE: protein ( x i ) SEQUENCE DESCRIPTION: SEQ ID NO:23:

| | | | | | | | | | | | | | | |
|---|---|---|---|---|---|---|---|---|---|---|---|---|---|---|
| Met | Ala | Met | Arg | Pro | Gly | Pro | Leu | Trp | Leu | Leu | Gly | Leu | Ala | Leu | Cys |
| 1 | | | | 5 | | | | | 10 | | | | | 15 | |
| Ala | Leu | Gly | Gly | Gly | His | Gly | Pro | Arg | Pro | Pro | His | Thr | Cys | Pro | Gln |
| | | | 20 | | | | | 25 | | | | | 30 | | |
| Arg | Arg | Leu | Gly | Ala | Arg | Glu | Arg | Arg | Asp | Met | Gln | Arg | Glu | Ile | Leu |
| | | 35 | | | | | 40 | | | | | 45 | | | |
| Ala | Val | Leu | Gly | Leu | Pro | Gly | Arg | Pro | Arg | Pro | Arg | Ala | Gln | Pro | Ala |
| | 50 | | | | | 55 | | | | | 60 | | | | |

Ala Ala Arg Gln Pro Ala Ser Ala Pro Leu Phe Met Leu Asp Leu Tyr
65                  70              75              80

His Ala Met Thr Asp Asp Asp Gly Gly Pro Pro Gln Ala His Leu
                85              90              95

Gly Arg Ala Asp Leu Val Met Ser Phe Val Asn Met Val Glu Arg Asp
            100             105             110

Arg Thr Leu Gly Tyr Gln Glu Pro His Trp Lys Glu Phe His Phe Asp
        115             120             125

Leu Thr Gln Ile Pro Ala Gly Glu Ala Val Thr Ala Ala Glu Phe Arg
    130             135             140

Ile Tyr Lys Glu Pro Ser Thr His Pro Leu Asn Thr Thr Leu His Ile
145             150             155             160

Ser Met Phe Glu Val Val Gln Glu His Ser Asn Arg Glu Ser Asp Leu
                165             170             175

Phe Phe Leu Asp Leu Gln Thr Leu Arg Ser Gly Asp Glu Gly Trp Leu
            180             185             190

Val Leu Asp Ile Thr Ala Ala Ser Asp Arg Trp Leu Leu Asn His His
        195             200             205

Lys Asp Leu Gly Leu Arg Leu Tyr Val Glu Thr Ala Asp Gly His Ser
    210             215             220

Met Asp Pro Gly Leu Ala Gly Leu Leu Gly Arg Gln Ala Pro Arg Ser
225             230             235             240

Arg Gln Pro Phe Met Val Thr Phe Phe Arg Ala Ser Gln Ser Pro Val
                245             250             255

Arg Ala Pro Arg Ala Ala Arg Pro Leu Lys Arg Arg Gln Pro Lys Lys
            260             265             270

Thr Asn Glu Leu Pro His Pro Asn Lys Leu Pro Gly Ile Phe Asp Asp
        275             280             285

Gly His Gly Ser Arg Gly Arg Glu Val Cys Arg Arg His Glu Leu Tyr
    290             295             300

Val Ser Phe Arg Asp Leu Gly Trp Leu Asp Trp Val Ile Ala Pro Gln
305             310             315             320

Gly Tyr Ser Ala Tyr Tyr Cys Glu Gly Glu Cys Ala Phe Pro Leu Asp
                325             330             335

Ser Cys Met Asn Ala Thr Asn His Ala Ile Leu Gln Ser Leu Val His
            340             345             350

Leu Met Lys Pro Asp Val Val Pro Lys Ala Cys Cys Ala Pro Thr Lys
        355             360             365

Leu Ser Ala Thr Ser Val Leu Tyr Tyr Asp Ser Ser Asn Asn Val Ile
    370             375             380

Leu Arg Lys His Arg Asn Met Val Val Lys Ala Cys Gly Cys His
385             390             395

(2) INFORMATION FOR SEQ ID NO:24:

(i) SEQUENCE CHARACTERISTICS:
        (A) LENGTH: 1368 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1365

(xi) SEQUENCE DESCRIPTION: SEQ ID NO:24:

```
ATG TCG GGA CTG CGA AAC ACC TCG GAG GCC GTT GCA GTG CTC GCC TCC                48
Met Ser Gly Leu Arg Asn Thr Ser Glu Ala Val Ala Val Leu Ala Ser
 1           5                  10                  15

CTG GGA CTC GGA ATG GTT CTG CTC ATG TTC GTG GCG ACC ACG CCG CCG                96
Leu Gly Leu Gly Met Val Leu Leu Met Phe Val Ala Thr Thr Pro Pro
            20                  25                  30

GCC GTT GAG GCC ACC CAG TCG GGG ATT TAC ATA GAC AAC GGC AAG GAC               144
Ala Val Glu Ala Thr Gln Ser Gly Ile Tyr Ile Asp Asn Gly Lys Asp
         35                  40                  45

CAG ACG ATC ATG CAC AGA GTG CTG AGC GAG GAC GAC AAG CTG GAC GTC               192
Gln Thr Ile Met His Arg Val Leu Ser Glu Asp Asp Lys Leu Asp Val
     50                  55                  60

TCG TAC GAG ATC CTC GAG TTC CTG GGC ATC GCC GAA CGG CCG ACG CAC               240
Ser Tyr Glu Ile Leu Glu Phe Leu Gly Ile Ala Glu Arg Pro Thr His
 65                  70                  75                  80

CTG AGC AGC CAC CAG TTG TCG CTG AGG AAG TCG GCT CCC AAG TTC CTG               288
Leu Ser Ser His Gln Leu Ser Leu Arg Lys Ser Ala Pro Lys Phe Leu
             85                  90                  95

CTG GAC GTC TAC CAC CGC ATC ACG GCG GAG GAG GGT CTC AGC GAT CAG               336
Leu Asp Val Tyr His Arg Ile Thr Ala Glu Glu Gly Leu Ser Asp Gln
            100                 105                 110

GAT GAG GAC GAC GAC TAC GAA CGC GGC CAT CGG TCC AGG AGG AGC GCC               384
Asp Glu Asp Asp Asp Tyr Glu Arg Gly His Arg Ser Arg Arg Ser Ala
        115                 120                 125

GAC CTC GAG GAG GAT GAG GGC GAG CAG CAG AAG AAC TTC ATC ACC GAC               432
Asp Leu Glu Glu Asp Glu Gly Glu Gln Gln Lys Asn Phe Ile Thr Asp
    130                 135                 140

CTG GAC AAG CGG GCC ATC GAC GAG AGC GAC ATC ATC ATG ACC TTC CTG               480
Leu Asp Lys Arg Ala Ile Asp Glu Ser Asp Ile Ile Met Thr Phe Leu
145                 150                 155                 160

AAC AAG CGC CAC CAC AAT GTG GAC GAA CTG CGT CAC GAG CAC GGC CGT               528
Asn Lys Arg His His Asn Val Asp Glu Leu Arg His Glu His Gly Arg
                165                 170                 175

CGC CTG TGG TTC GAC GTC TCC AAC GTG CCC AAC GAC AAC TAC CTG GTG               576
Arg Leu Trp Phe Asp Val Ser Asn Val Pro Asn Asp Asn Tyr Leu Val
            180                 185                 190

ATG GCC GAG CTG CGC ATC TAT CAG AAC GCC AAC GAG GGC AAG TGG CTG               624
Met Ala Glu Leu Arg Ile Tyr Gln Asn Ala Asn Glu Gly Lys Trp Leu
        195                 200                 205

ACC GCC AAC AGG GAG TTC ACC ATC ACG GTA TAC GCC ATT GGC ACC GGC               672
Thr Ala Asn Arg Glu Phe Thr Ile Thr Val Tyr Ala Ile Gly Thr Gly
    210                 215                 220

ACG CTG GGC CAG CAC ACC ATG GAG CCG CTG TCC TCG GTG AAC ACC ACC               720
Thr Leu Gly Gln His Thr Met Glu Pro Leu Ser Ser Val Asn Thr Thr
225                 230                 235                 240

GGG GAC TAC GTG GGC TGG TTG GAG CTC AAC GTG ACC GAG GGC CTG CAC               768
Gly Asp Tyr Val Gly Trp Leu Glu Leu Asn Val Thr Glu Gly Leu His
                245                 250                 255

GAG TGG CTG GTC AAG TCG AAG GAC AAT CAT GGC ATC TAC ATT GGA GCA               816
Glu Trp Leu Val Lys Ser Lys Asp Asn His Gly Ile Tyr Ile Gly Ala
            260                 265                 270

CAC GCT GTC AAC CGA CCC GAC CGC GAG GTG AAG CTG GAC GAC ATT GGA               864
His Ala Val Asn Arg Pro Asp Arg Glu Val Lys Leu Asp Asp Ile Gly
        275                 280                 285

CTG ATC CAC CGC AAG GTG GAC GAC GAG TTC CAG CCC TTC ATG ATC GGC               912
Leu Ile His Arg Lys Val Asp Asp Glu Phe Gln Pro Phe Met Ile Gly
    290                 295                 300

TTC TTC CGC GGA CCG GAG CTG ATC AAG GCG ACG GCC CAC AGC AGC CAC               960
Phe Phe Arg Gly Pro Glu Leu Ile Lys Ala Thr Ala His Ser Ser His
305                 310                 315                 320
```

| | | | | | | | | | | | | | | | | |
|---|---|---|---|---|---|---|---|---|---|---|---|---|---|---|---|---|
| CAC | AGG | AGC | AAG | CGA | AGC | GCC | AGC | CAT | CCA | CGC | AAG | CGC | AAG | AAG | TCG | 1008 |
| His | Arg | Ser | Lys | Arg | Ser | Ala | Ser | His | Pro | Arg | Lys | Arg | Lys | Lys | Ser | |
| | | | | 325 | | | | | 330 | | | | | 335 | | |
| GTG | TCG | CCC | AAC | AAC | GTG | CCG | CTG | CTG | GAA | CCG | ATG | GAG | AGC | ACG | CGC | 1056 |
| Val | Ser | Pro | Asn | Asn | Val | Pro | Leu | Leu | Glu | Pro | Met | Glu | Ser | Thr | Arg | |
| | | | 340 | | | | | 345 | | | | | 350 | | | |
| AGC | TGC | CAG | ATG | CAG | ACC | CTG | TAC | ATA | GAC | TTC | AAG | GAT | CTG | GGC | TGG | 1104 |
| Ser | Cys | Gln | Met | Gln | Thr | Leu | Tyr | Ile | Asp | Phe | Lys | Asp | Leu | Gly | Trp | |
| | | | 355 | | | | | 360 | | | | | 365 | | | |
| CAT | GAC | TGG | ATC | ATC | GCA | CCA | GAG | GGC | TAT | GGC | GCC | TTC | TAC | TGC | AGC | 1152 |
| His | Asp | Trp | Ile | Ile | Ala | Pro | Glu | Gly | Tyr | Gly | Ala | Phe | Tyr | Cys | Ser | |
| | | 370 | | | | 375 | | | | | 380 | | | | | |
| GGC | GAG | TGC | AAT | TTC | CCG | CTC | AAT | GCG | CAC | ATG | AAC | GCC | ACG | AAC | CAT | 1200 |
| Gly | Glu | Cys | Asn | Phe | Pro | Leu | Asn | Ala | His | Met | Asn | Ala | Thr | Asn | His | |
| 385 | | | | | 390 | | | | | 395 | | | | | 400 | |
| GCG | ATC | GTC | CAG | ACC | CTG | GTC | CAC | CTG | CTG | GAG | CCC | AAG | AAG | GTG | CCC | 1248 |
| Ala | Ile | Val | Gln | Thr | Leu | Val | His | Leu | Leu | Glu | Pro | Lys | Lys | Val | Pro | |
| | | | | 405 | | | | | 410 | | | | | 415 | | |
| AAG | CCC | TGC | TGC | GCT | CCG | ACC | AGG | CTG | GGA | GCA | CTA | CCC | GTT | CTG | TAC | 1296 |
| Lys | Pro | Cys | Cys | Ala | Pro | Thr | Arg | Leu | Gly | Ala | Leu | Pro | Val | Leu | Tyr | |
| | | | 420 | | | | 425 | | | | | 430 | | | | |
| CAC | CTG | AAC | GAC | GAG | AAT | GTG | AAC | CTG | AAA | AAG | TAT | AGA | AAC | ATG | ATT | 1344 |
| His | Leu | Asn | Asp | Glu | Asn | Val | Asn | Leu | Lys | Lys | Tyr | Arg | Asn | Met | Ile | |
| | | | 435 | | | | 440 | | | | | 445 | | | | |
| GTG | AAA | TCC | TGC | GGG | TGC | CAT | TGA | | | | | | | | | 1368 |
| Val | Lys | Ser | Cys | Gly | Cys | His | | | | | | | | | | |
| | 450 | | | | | 455 | | | | | | | | | | |

( 2 ) INFORMATION FOR SEQ ID NO:25:

( i ) SEQUENCE CHARACTERISTICS:
        ( A ) LENGTH: 455 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

| | | | | | | | | | | | | | | |
|---|---|---|---|---|---|---|---|---|---|---|---|---|---|---|
| Met | Ser | Gly | Leu | Arg | Asn | Thr | Ser | Glu | Ala | Val | Ala | Val | Leu | Ala | Ser |
| 1 | | | | 5 | | | | | 10 | | | | | 15 | |
| Leu | Gly | Leu | Gly | Met | Val | Leu | Leu | Met | Phe | Val | Ala | Thr | Thr | Pro | Pro |
| | | | 20 | | | | | 25 | | | | | 30 | | |
| Ala | Val | Glu | Ala | Thr | Gln | Ser | Gly | Ile | Tyr | Ile | Asp | Asn | Gly | Lys | Asp |
| | | | 35 | | | | 40 | | | | | 45 | | | |
| Gln | Thr | Ile | Met | His | Arg | Val | Leu | Ser | Glu | Asp | Lys | Leu | Asp | Val | |
| | 50 | | | | | 55 | | | | | 60 | | | | |
| Ser | Tyr | Glu | Ile | Leu | Glu | Phe | Leu | Gly | Ile | Ala | Glu | Arg | Pro | Thr | His |
| 65 | | | | | 70 | | | | | 75 | | | | | 80 |
| Leu | Ser | Ser | His | Gln | Leu | Ser | Leu | Arg | Lys | Ser | Ala | Pro | Lys | Phe | Leu |
| | | | | 85 | | | | | 90 | | | | | 95 | |
| Leu | Asp | Val | Tyr | His | Arg | Ile | Thr | Ala | Glu | Glu | Gly | Leu | Ser | Asp | Gln |
| | | | | 100 | | | | | 105 | | | | | 110 | |
| Asp | Glu | Asp | Asp | Asp | Tyr | Glu | Arg | Gly | His | Arg | Ser | Arg | Arg | Ser | Ala |
| | | | 115 | | | | | 120 | | | | | 125 | | |
| Asp | Leu | Glu | Glu | Asp | Glu | Gly | Gln | Gln | Lys | Asn | Phe | Ile | Thr | Asp | |
| | 130 | | | | | 135 | | | | | 140 | | | | |
| Leu | Asp | Lys | Arg | Ala | Ile | Asp | Glu | Ser | Asp | Ile | Ile | Met | Thr | Phe | Leu |
| 145 | | | | | 150 | | | | | 155 | | | | | 160 |
| Asn | Lys | Arg | His | His | Asn | Val | Asp | Glu | Leu | Arg | His | Glu | His | Gly | Arg |
| | | | | 165 | | | | | 170 | | | | | 175 | |

```
Arg Leu Trp Phe Asp Val Ser Asn Val Pro Asn Asp Asn Tyr Leu Val
            180                 185                 190

Met Ala Glu Leu Arg Ile Tyr Gln Asn Ala Asn Glu Gly Lys Trp Leu
            195                 200                 205

Thr Ala Asn Arg Glu Phe Thr Ile Thr Val Tyr Ala Ile Gly Thr Gly
            210                 215                 220

Thr Leu Gly Gln His Thr Met Glu Pro Leu Ser Ser Val Asn Thr Thr
225                     230                 235                 240

Gly Asp Tyr Val Gly Trp Leu Glu Leu Asn Val Thr Glu Gly Leu His
                245                 250                 255

Glu Trp Leu Val Lys Ser Lys Asp Asn His Gly Ile Tyr Ile Gly Ala
            260                 265                 270

His Ala Val Asn Arg Pro Asp Arg Glu Val Lys Leu Asp Asp Ile Gly
            275                 280                 285

Leu Ile His Arg Lys Val Asp Asp Glu Phe Gln Pro Phe Met Ile Gly
            290                 295                 300

Phe Phe Arg Gly Pro Glu Leu Ile Lys Ala Thr Ala His Ser Ser His
305                     310                 315                 320

His Arg Ser Lys Arg Ser Ala Ser His Pro Arg Lys Arg Lys Lys Ser
                325                 330                 335

Val Ser Pro Asn Asn Val Pro Leu Leu Glu Pro Met Glu Ser Thr Arg
            340                 345                 350

Ser Cys Gln Met Gln Thr Leu Tyr Ile Asp Phe Lys Asp Leu Gly Trp
            355                 360                 365

His Asp Trp Ile Ile Ala Pro Glu Gly Tyr Gly Ala Phe Tyr Cys Ser
            370                 375                 380

Gly Glu Cys Asn Phe Pro Leu Asn Ala His Met Asn Ala Thr Asn His
385                     390                 395                 400

Ala Ile Val Gln Thr Leu Val His Leu Leu Glu Pro Lys Lys Val Pro
                405                 410                 415

Lys Pro Cys Cys Ala Pro Thr Arg Leu Gly Ala Leu Pro Val Leu Tyr
            420                 425                 430

His Leu Asn Asp Glu Asn Val Asn Leu Lys Lys Tyr Arg Asn Met Ile
            435                 440                 445

Val Lys Ser Cys Gly Cys His
450                     455
```

(2) INFORMATION FOR SEQ ID NO:26:

(i) SEQUENCE CHARACTERISTICS:
        (A) LENGTH: 104 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..104
        (D) OTHER INFORMATION: /label=BMP3

(xi) SEQUENCE DESCRIPTION: SEQ ID NO:26:

```
Cys Ala Arg Arg Tyr Leu Lys Val Asp Phe Ala Asp Ile Gly Trp Ser
1               5                   10                  15

Glu Trp Ile Ile Ser Pro Lys Ser Phe Asp Ala Tyr Tyr Cys Ser Gly
            20                  25                  30

Ala Cys Gln Phe Pro Met Pro Lys Ser Leu Lys Pro Ser Asn His Ala
```

|       |     |     |     |     | 35  |     |     |     |     | 40  |     |     |     |     | 45  |     |
|-------|-----|-----|-----|-----|-----|-----|-----|-----|-----|-----|-----|-----|-----|-----|-----|-----|

Thr Ile Gln Ser Ile Val Ala Arg Ala Val Gly Val Val Pro Gly Ile
        50                  55                  60

Pro Glu Pro Cys Cys Val Pro Glu Lys Met Ser Ser Leu Ser Ile Leu
65                      70                  75                  80

Phe Phe Asp Glu Asn Lys Asn Val Val Leu Lys Val Tyr Pro Asn Met
                85                  90                  95

Thr Val Glu Ser Cys Ala Cys Arg
              100

( 2 ) INFORMATION FOR SEQ ID NO:27:

( i ) SEQUENCE CHARACTERISTICS:
      ( A ) LENGTH: 102 amino acids
      ( B ) TYPE: amino acid
      ( C ) STRANDEDNESS: single
      ( D ) TOPOLOGY: linear ( i i ) MOLECULE TYPE: protein ( i x ) FEATURE:
      ( A ) NAME/KEY: Protein
      ( B ) LOCATION: 1..102
      ( D ) OTHER INFORMATION: /label=BMP5

( x i ) SEQUENCE DESCRIPTION: SEQ ID NO:27:

Cys Lys Lys His Glu Leu Tyr Val Ser Phe Arg Asp Leu Gly Trp Gln
1               5                   10                  15

Asp Trp Ile Ile Ala Pro Glu Gly Tyr Ala Ala Phe Tyr Cys Asp Gly
                20                  25                  30

Glu Cys Ser Phe Pro Leu Asn Ala His Met Asn Ala Thr Asn His Ala
              35                  40                  45

Ile Val Gln Thr Leu Val His Leu Met Phe Pro Asp His Val Pro Lys
        50                  55                  60

Pro Cys Cys Ala Pro Thr Lys Leu Asn Ala Ile Ser Val Leu Tyr Phe
65                      70                  75                  80

Asp Asp Ser Ser Asn Val Ile Leu Lys Lys Tyr Arg Asn Met Val Val
                85                  90                  95

Arg Ser Cys Gly Cys His
              100

( 2 ) INFORMATION FOR SEQ ID NO:28:

( i ) SEQUENCE CHARACTERISTICS:
      ( A ) LENGTH: 102 amino acids
      ( B ) TYPE: amino acid
      ( C ) STRANDEDNESS: single
      ( D ) TOPOLOGY: linear ( i i ) MOLECULE TYPE: protein ( i x ) FEATURE:
      ( A ) NAME/KEY: Protein
      ( B ) LOCATION: 1..102
      ( D ) OTHER INFORMATION: /label=BMP6

( x i ) SEQUENCE DESCRIPTION: SEQ ID NO:28:

Cys Arg Lys His Glu Leu Tyr Val Ser Phe Gln Asp Leu Gly Trp Gln
1               5                   10                  15

Asp Trp Ile Ile Ala Pro Lys Gly Tyr Ala Ala Asn Tyr Cys Asp Gly
                20                  25                  30

Glu Cys Ser Phe Pro Leu Asn Ala His Met Asn Ala Thr Asn His Ala
              35                  40                  45

```
Ile  Val  Gln  Thr  Leu  Val  His  Leu  Met  Asn  Pro  Glu  Tyr  Val  Pro  Lys
     50                  55                      60

Pro  Cys  Cys  Ala  Pro  Thr  Lys  Leu  Asn  Ala  Ile  Ser  Val  Leu  Tyr  Phe
65                       70                       75                        80

Asp  Asp  Asn  Ser  Asn  Val  Ile  Leu  Lys  Lys  Tyr  Arg  Trp  Met  Val  Val
               85                       90                             95

Arg  Ala  Cys  Gly  Cys  His
               100
```

( 2 ) INFORMATION FOR SEQ ID NO:29:

( i ) SEQUENCE CHARACTERISTICS:
        ( A ) LENGTH: 102 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..102
        ( D ) OTHER INFORMATION: /label=OPX
            / note= "WHEREIN XAA AT EACH POS'N IS INDEPENDENTLY
            SELECTED FROM THE RESIDUES OCCURING AT THE CORRESPONDING
            POS'N IN THE C-TERMINAL SEQUENCE OF MOUSE OR HUMAN OP1
            OR OP2 (SEQ. ID NOS. 5,6,7&8 OR 16,18, 20&22"

( x i ) SEQUENCE DESCRIPTION: SEQ ID NO:29:

```
Cys  Xaa  Xaa  His  Glu  Leu  Tyr  Val  Xaa  Phe  Xaa  Asp  Leu  Gly  Trp  Xaa
1                        5                        10                       15

Asp  Trp  Xaa  Ile  Ala  Pro  Xaa  Gly  Tyr  Xaa  Ala  Tyr  Tyr  Cys  Glu  Gly
               20                  25                            30

Glu  Cys  Xaa  Phe  Pro  Leu  Xaa  Ser  Xaa  Met  Asn  Ala  Thr  Asn  His  Ala
               35                  40                       45

Ile  Xaa  Gln  Xaa  Leu  Val  His  Xaa  Xaa  Xaa  Pro  Xaa  Xaa  Val  Pro  Lys
     50                       55                       60

Xaa  Cys  Cys  Ala  Pro  Thr  Xaa  Leu  Xaa  Ala  Xaa  Ser  Val  Leu  Tyr  Xaa
65                       70                       75                        80

Asp  Xaa  Ser  Xaa  Asn  Val  Xaa  Leu  Xaa  Lys  Xaa  Arg  Asn  Met  Val  Val
               85                       90                             95

Xaa  Ala  Cys  Gly  Cys  His
               100
```

( 2 ) INFORMATION FOR SEQ ID NO:30:

( i ) SEQUENCE CHARACTERISTICS:
        ( A ) LENGTH: 97 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..97
        ( D ) OTHER INFORMATION: /label=GENERIC-SEQ-5
            / note= "WHEREIN EACH XAA IS INDEPENDENTLY SELECTED FROM
            A GROUP OF ONE OR MORE SPECIFIED AMINO ACIDS AS DEFINED
            IN THE SPECIFICATION"

( x i ) SEQUENCE DESCRIPTION: SEQ ID NO:30:

```
Leu  Xaa  Xaa  Xaa  Phe  Xaa  Xaa  Xaa  Gly  Trp  Xaa  Xaa  Trp  Xaa  Xaa  Xaa
1                        5                        10                       15

Pro  Xaa  Xaa  Xaa  Xaa  Ala  Xaa  Tyr  Cys  Xaa  Gly  Xaa  Cys  Xaa  Xaa  Pro
```

```
                            20                     25                       30
        Xaa  Xaa  Xaa  Xaa  Xaa  Xaa  Xaa  Xaa  Asn  His  Ala  Xaa  Xaa  Xaa  Xaa  Xaa
                      35                     40                    45

Xaa  Xaa  Xaa  Xaa  Xaa  Xaa  Xaa  Xaa  Xaa  Xaa  Xaa  Xaa  Cys  Cys  Xaa  Pro
             50                          55                   60

Xaa  Xaa  Xaa  Xaa  Xaa  Xaa  Xaa  Xaa  Leu  Xaa  Xaa  Xaa  Xaa  Xaa  Xaa  Xaa
        65                        70                      75                         80

Val  Xaa  Leu  Xaa  Xaa  Xaa  Xaa  Xaa  Met  Xaa  Val  Xaa  Xaa  Cys  Xaa  Cys
                            85                   90                          95

Xaa
```

(2) INFORMATION FOR SEQ ID NO:31:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /label=GENERIC-SEQ-6
        / note= "WHEREIN EACH XAA IS INDEPENDENTLY SELECTED FROM
        A GROUP OF ONE OR MORE SPECIFIED AMINO ACIDS AS DEFINED
        IN THE SPECIFICATION"

(xi) SEQUENCE DESCRIPTION: SEQ ID NO:31:

```
        Cys  Xaa  Xaa  Xaa  Xaa  Leu  Xaa  Xaa  Xaa  Phe  Xaa  Xaa  Xaa  Gly  Trp  Xaa
        1                   5                        10                      15

Xaa  Trp  Xaa  Xaa  Xaa  Pro  Xaa  Xaa  Xaa  Xaa  Ala  Xaa  Tyr  Cys  Xaa  Gly
                       20                       25                    30

Xaa  Cys  Xaa  Xaa  Pro  Xaa  Xaa  Xaa  Xaa  Xaa  Xaa  Xaa  Xaa  Asn  His  Ala
                  35                       40                     45

Xaa  Xaa  Xaa  Xaa  Xaa  Xaa  Xaa  Xaa  Xaa  Xaa  Xaa  Xaa  Xaa  Xaa  Xaa  Xaa
             50                       55                        60

Xaa  Cys  Cys  Xaa  Pro  Xaa  Xaa  Xaa  Xaa  Xaa  Xaa  Xaa  Xaa  Leu  Xaa  Xaa
        65                       70                      75                          80

Xaa  Xaa  Xaa  Xaa  Xaa  Val  Xaa  Leu  Xaa  Xaa  Xaa  Xaa  Xaa  Met  Xaa  Val
                            85                   90                         95

Xaa  Xaa  Cys  Xaa  Cys  Xaa
                       100
```

(2) INFORMATION FOR SEQ ID NO:32:

(i) SEQUENCE CHARACTERISTICS:
        (A) LENGTH: 1247 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 84..1199
        (D) OTHER INFORMATION: /product="GDF-1"

(xi) SEQUENCE DESCRIPTION: SEQ ID NO:32:

```
GGGGACACCG  GCCCCGCCCT  CAGCCCACTG  GTCCCGGGCC  GCCGCGGACC  CTGCGCACTC        60

TCTGGTCATC  GCCTGGGAGG  AAG ATG CCA  CCG CCG CAG  CAA GGT CCC  TGC            110
                           Met Pro Pro  Pro Gln  Gln Gly Pro  Cys
```

```
GGC CAC CAC CTC CTC CTC CTC CTG GCC CTG CTG CTG CCC TCG CTG CCC      158
Gly His His Leu Leu Leu Leu Leu Ala Leu Leu Leu Pro Ser Leu Pro
 10              15                  20                  25

CTG ACC CGC GCC CCC GTG CCC CCA GGC CCA GCC GCC GCC CTG CTC CAG      206
Leu Thr Arg Ala Pro Val Pro Pro Gly Pro Ala Ala Ala Leu Leu Gln
                 30                  35                  40

GCT CTA GGA CTG CGC GAT GAG CCC CAG GGT GCC CCC AGG CTC CGG CCG      254
Ala Leu Gly Leu Arg Asp Glu Pro Gln Gly Ala Pro Arg Leu Arg Pro
             45                  50                  55

GTT CCC CCG GTC ATG TGG CGC CTG TTT CGA CGC CGG GAC CCC CAG GAG      302
Val Pro Pro Val Met Trp Arg Leu Phe Arg Arg Arg Asp Pro Gln Glu
         60                  65                  70

ACC AGG TCT GGC TCG CGG CGG ACG TCC CCA GGG GTC ACC CTG CAA CCG      350
Thr Arg Ser Gly Ser Arg Arg Thr Ser Pro Gly Val Thr Leu Gln Pro
     75                  80                  85

TGC CAC GTG GAG GAG CTG GGG GTC GCC GGA AAC ATC GTG CGC CAC ATC      398
Cys His Val Glu Glu Leu Gly Val Ala Gly Asn Ile Val Arg His Ile
 90                  95                 100                 105

CCG GAC CGC GGT GCG CCC ACC CGG GCC TCG GAG CCT GTC TCG GCC GCG      446
Pro Asp Arg Gly Ala Pro Thr Arg Ala Ser Glu Pro Val Ser Ala Ala
                110                 115                 120

GGG CAT TGC CCT GAG TGG ACA GTC GTC TTC GAC CTG TCG GCT GTG GAA      494
Gly His Cys Pro Glu Trp Thr Val Val Phe Asp Leu Ser Ala Val Glu
            125                 130                 135

CCC GCT GAG CGC CCG AGC CGG GCC CGC CTG GAG CTG CGT TTC GCG GCG      542
Pro Ala Glu Arg Pro Ser Arg Ala Arg Leu Glu Leu Arg Phe Ala Ala
        140                 145                 150

GCG GCG GCG GCA GCC CCG GAG GGC GGC TGG GAG CTG AGC GTG GCG CAA      590
Ala Ala Ala Ala Ala Pro Glu Gly Gly Trp Glu Leu Ser Val Ala Gln
    155                 160                 165

GCG GGC CAG GGC GCG GGC GCG GAC CCC GGG CCG GTG CTG CTC CGC CAG      638
Ala Gly Gln Gly Ala Gly Ala Asp Pro Gly Pro Val Leu Leu Arg Gln
170                 175                 180                 185

TTG GTG CCC GCC CTG GGG CCG CCA GTG CGC GCG GAG CTG CTG GGC GCC      686
Leu Val Pro Ala Leu Gly Pro Pro Val Arg Ala Glu Leu Leu Gly Ala
                190                 195                 200

GCT TGG GCT CGC AAC GCC TCA TGG CCG CGC AGC CTC CGC CTG GCG CTG      734
Ala Trp Ala Arg Asn Ala Ser Trp Pro Arg Ser Leu Arg Leu Ala Leu
            205                 210                 215

GCG CTA CGC CCC CGG GCC CCT GCC GCC TGC GCG CGC CTG GCC GAG GCC      782
Ala Leu Arg Pro Arg Ala Pro Ala Ala Cys Ala Arg Leu Ala Glu Ala
        220                 225                 230

TCG CTG CTG CTG GTG ACC CTC GAC CCG CGC CTG TGC CAC CCC CTG GCC      830
Ser Leu Leu Leu Val Thr Leu Asp Pro Arg Leu Cys His Pro Leu Ala
    235                 240                 245

CGG CCG CGG CGC GAC GCC GAA CCC GTG TTG GGC GGC GGC CCC GGG GGC      878
Arg Pro Arg Arg Asp Ala Glu Pro Val Leu Gly Gly Gly Pro Gly Gly
250                 255                 260                 265

GCT TGT CGC GCG CGG CGG CTG TAC GTG AGC TTC CGC GAG GTG GGC TGG      926
Ala Cys Arg Ala Arg Arg Leu Tyr Val Ser Phe Arg Glu Val Gly Trp
                270                 275                 280

CAC CGC TGG GTC ATC GCG CCG CGC GGC TTC CTG GCC AAC TAC TGC CAG      974
His Arg Trp Val Ile Ala Pro Arg Gly Phe Leu Ala Asn Tyr Cys Gln
            285                 290                 295

GGT CAG TGC GCG CTG CCC GTC GCG CTG TCG GGG TCC GGG GGG CCG CCG     1022
Gly Gln Cys Ala Leu Pro Val Ala Leu Ser Gly Ser Gly Gly Pro Pro
        300                 305                 310

GCG CTC AAC CAC GCT GTG CTG CGC GCG CTC ATG CAC GCG GCC GCC CCG     1070
Ala Leu Asn His Ala Val Leu Arg Ala Leu Met His Ala Ala Ala Pro
```

|     |     |     |     |     | 315 |     |     |     | 320 |     |     |     |     | 325 |     |      |
|-----|-----|-----|-----|-----|-----|-----|-----|-----|-----|-----|-----|-----|-----|-----|-----|------|
| GGA | GCC | GCC | GAC | CTG | CCC | TGC | TGC | GTG | CCC | GCG | CGC | CTG | TCG | CCC | ATC | 1118 |
| Gly | Ala | Ala | Asp | Leu | Pro | Cys | Cys | Val | Pro | Ala | Arg | Leu | Ser | Pro | Ile |      |
| 330 |     |     |     |     | 335 |     |     |     | 340 |     |     |     |     | 345 |     |      |
| TCC | GTG | CTC | TTC | TTT | GAC | AAC | AGC | GAC | AAC | GTG | GTG | CTG | CGG | CAG | TAT | 1166 |
| Ser | Val | Leu | Phe | Phe | Asp | Asn | Ser | Asp | Asn | Val | Val | Leu | Arg | Gln | Tyr |      |
|     |     |     |     | 350 |     |     |     | 355 |     |     |     |     |     | 360 |     |      |
| GAG | GAC | ATG | GTG | GTG | GAC | GAG | TGC | GGC | TGC | CGC | TAACCCGGGG | CGGGCAGGGA | | | | 1219 |
| Glu | Asp | Met | Val | Val | Asp | Glu | Cys | Gly | Cys | Arg |     |     |     |     |     |      |
|     |     |     | 365 |     |     |     |     | 370 |     |     |     |     |     |     |     |      |

CCCGGGCCCA ACAATAAATG CCGCGTGG                                                                          1247

( 2 ) INFORMATION FOR SEQ ID NO:33:

( i ) SEQUENCE CHARACTERISTICS:
        ( A ) LENGTH: 372 amino acids
        ( B ) TYPE: amino acid
        ( D ) TOPOLOGY: linear ( i i ) MOLECULE TYPE: protein ( x i ) SEQUENCE DESCRIPTION: SEQ ID NO:33:

| Met | Pro | Pro | Pro | Gln | Gly | Pro | Cys | Gly | His | His | Leu | Leu | Leu | Leu |
|-----|-----|-----|-----|-----|-----|-----|-----|-----|-----|-----|-----|-----|-----|-----|
| 1   |     |     |     | 5   |     |     |     | 10  |     |     |     |     | 15  |     |
| Leu | Ala | Leu | Leu | Leu | Pro | Ser | Leu | Pro | Leu | Thr | Arg | Ala | Pro | Val | Pro |
|     |     |     | 20  |     |     |     | 25  |     |     |     |     | 30  |     |     |     |
| Pro | Gly | Pro | Ala | Ala | Ala | Leu | Leu | Gln | Ala | Leu | Gly | Leu | Arg | Asp | Glu |
|     |     | 35  |     |     |     | 40  |     |     |     |     | 45  |     |     |     |     |
| Pro | Gln | Gly | Ala | Pro | Arg | Leu | Arg | Pro | Val | Pro | Pro | Val | Met | Trp | Arg |
|     | 50  |     |     |     | 55  |     |     |     |     | 60  |     |     |     |     |     |
| Leu | Phe | Arg | Arg | Arg | Asp | Pro | Gln | Glu | Thr | Arg | Ser | Gly | Ser | Arg | Arg |
| 65  |     |     |     | 70  |     |     |     |     | 75  |     |     |     |     | 80  |     |
| Thr | Ser | Pro | Gly | Val | Thr | Leu | Gln | Pro | Cys | His | Val | Glu | Glu | Leu | Gly |
|     |     |     |     | 85  |     |     |     |     | 90  |     |     |     |     | 95  |     |
| Val | Ala | Gly | Asn | Ile | Val | Arg | His | Ile | Pro | Asp | Arg | Gly | Ala | Pro | Thr |
|     |     |     | 100 |     |     |     | 105 |     |     |     |     | 110 |     |     |     |
| Arg | Ala | Ser | Glu | Pro | Val | Ser | Ala | Ala | Gly | His | Cys | Pro | Glu | Trp | Thr |
|     |     | 115 |     |     |     | 120 |     |     |     |     | 125 |     |     |     |     |
| Val | Val | Phe | Asp | Leu | Ser | Ala | Val | Glu | Pro | Ala | Glu | Arg | Pro | Ser | Arg |
|     | 130 |     |     |     | 135 |     |     |     |     | 140 |     |     |     |     |     |
| Ala | Arg | Leu | Glu | Leu | Arg | Phe | Ala | Ala | Ala | Ala | Ala | Ala | Pro | Glu |
| 145 |     |     |     | 150 |     |     |     |     | 155 |     |     |     |     | 160 |
| Gly | Gly | Trp | Glu | Leu | Ser | Val | Ala | Gln | Ala | Gly | Gln | Gly | Ala | Gly | Ala |
|     |     |     |     | 165 |     |     |     | 170 |     |     |     |     | 175 |     |     |
| Asp | Pro | Gly | Pro | Val | Leu | Leu | Arg | Gln | Leu | Val | Pro | Ala | Leu | Gly | Pro |
|     |     |     | 180 |     |     |     |     | 185 |     |     |     |     | 190 |     |     |
| Pro | Val | Arg | Ala | Glu | Leu | Leu | Gly | Ala | Ala | Trp | Ala | Arg | Asn | Ala | Ser |
|     |     | 195 |     |     |     |     | 200 |     |     |     | 205 |     |     |     |     |
| Trp | Pro | Arg | Ser | Leu | Arg | Leu | Ala | Leu | Ala | Leu | Arg | Pro | Arg | Ala | Pro |
|     | 210 |     |     |     | 215 |     |     |     |     | 220 |     |     |     |     |     |
| Ala | Ala | Cys | Ala | Arg | Leu | Ala | Glu | Ala | Ser | Leu | Leu | Leu | Val | Thr | Leu |
| 225 |     |     |     | 230 |     |     |     |     | 235 |     |     |     |     | 240 |
| Asp | Pro | Arg | Leu | Cys | His | Pro | Leu | Ala | Arg | Pro | Arg | Arg | Asp | Ala | Glu |
|     |     |     |     | 245 |     |     |     |     | 250 |     |     |     |     | 255 |     |
| Pro | Val | Leu | Gly | Gly | Gly | Pro | Gly | Gly | Ala | Cys | Arg | Ala | Arg | Arg | Leu |
|     |     |     |     | 260 |     |     |     |     | 265 |     |     |     |     | 270 |     |
| Tyr | Val | Ser | Phe | Arg | Glu | Val | Gly | Trp | His | Arg | Trp | Val | Ile | Ala | Pro |

|     |     |     | 275 |     |     |     | 280 |     |     |     | 285 |     |     |     |
| --- | --- | --- | --- | --- | --- | --- | --- | --- | --- | --- | --- | --- | --- | --- |
| Arg | Gly | Phe | Leu | Ala | Asn | Tyr | Cys | Gln | Gly | Gln | Cys | Ala | Leu | Pro | Val |
|     | 290 |     |     |     |     | 295 |     |     |     |     | 300 |     |     |     |
| Ala | Leu | Ser | Gly | Ser | Gly | Gly | Pro | Pro | Ala | Leu | Asn | His | Ala | Val | Leu |
| 305 |     |     |     |     | 310 |     |     |     |     | 315 |     |     |     |     | 320 |
| Arg | Ala | Leu | Met | His | Ala | Ala | Ala | Pro | Gly | Ala | Ala | Asp | Leu | Pro | Cys |
|     |     |     |     | 325 |     |     |     |     | 330 |     |     |     |     | 335 |     |
| Cys | Val | Pro | Ala | Arg | Leu | Ser | Pro | Ile | Ser | Val | Leu | Phe | Phe | Asp | Asn |
|     |     |     | 340 |     |     |     |     | 345 |     |     |     |     | 350 |     |     |
| Ser | Asp | Asn | Val | Val | Leu | Arg | Gln | Tyr | Glu | Asp | Met | Val | Val | Asp | Glu |
|     |     | 355 |     |     |     |     | 360 |     |     |     |     | 365 |     |     |     |
| Cys | Gly | Cys | Arg |
|     | 370 |     |     |